(12) United States Patent
Tebbs et al.

(10) Patent No.: US 8,954,337 B2
(45) Date of Patent: *Feb. 10, 2015

(54) INTERACTIVE GENOME BROWSER

(75) Inventors: Brice Tebbs, Spokane, WA (US); Blake C. Ballif, Greenacres, WA (US); Bassem A. Bejjani, Spokane, WA (US); Lisa G. Shaffer, Colbert, WA (US)

(73) Assignee: Signature Genomic, Spokane, WA (US)

( * ) Notice: Subject to any disclaimer, the term of this patent is extended or adjusted under 35 U.S.C. 154(b) by 369 days.

This patent is subject to a terminal disclaimer.

(21) Appl. No.: 12/614,009

(22) Filed: Nov. 6, 2009

(65) Prior Publication Data

US 2010/0286994 A1 Nov. 11, 2010

Related U.S. Application Data

(60) Provisional application No. 61/113,131, filed on Nov. 10, 2008.

(51) Int. Cl.
| G06Q 50/00 | (2012.01) |
| G06Q 50/22 | (2012.01) |
| G06F 19/00 | (2011.01) |
| G06F 19/28 | (2011.01) |
| G06F 19/26 | (2011.01) |
| G06F 19/18 | (2011.01) |

(52) U.S. Cl.
CPC ............... *G06F 19/28* (2013.01); *G06F 19/26* (2013.01); *G06Q 50/22* (2013.01); *G06F 19/18* (2013.01); *G06F 19/00* (2013.01)
USPC ............................................................ 705/2

(58) Field of Classification Search
CPC ............................... G06Q 50/22; G06Q 50/24
USPC ........................................................ 705/2–3
See application file for complete search history.

(56) References Cited

U.S. PATENT DOCUMENTS

| 2002/0048763 | A1 | 4/2002 | Penn et al. |
| 2002/0052761 | A1* | 5/2002 | Fey et al. ........................... 705/2 |
| 2002/0177137 | A1* | 11/2002 | Hodge .............................. 435/6 |
| 2002/0183936 | A1 | 12/2002 | Kulp et al. |
| 2003/0003478 | A1 | 1/2003 | Depinho et al. |
| 2003/0009295 | A1* | 1/2003 | Markowitz et al. ............. 702/20 |
| 2003/0119035 | A1 | 6/2003 | Presnell et al. |
| 2003/0220820 | A1* | 11/2003 | Sears et al. ........................ 705/3 |
| 2004/0142371 | A1* | 7/2004 | Milosavljevic et al. .......... 435/6 |

(Continued)

OTHER PUBLICATIONS

Voight, Benjamin F. "Approaching Human Genetics from a Population-Based Paradigm." Order No. 3219598 The University of Chicago, 2006. Ann Arbor: ProQuest. Web. Mar. 17, 2014.*

(Continued)

*Primary Examiner* — Sheetal R Rangrej
(74) *Attorney, Agent, or Firm* — Lee & Hayes, PLLC

(57) ABSTRACT

Disclosed is an interactive genome browser executing within a web browser application, configured to display patient genetic data and additional genetic data tracks which are aligned by base pair. Additional tracks may include public data, community data, private data, sequence gaps, and additional genetic tests or probes which are available. Tests or probes may be ordered by selecting them from a test or probe track. Data in a genetic information database may also be searched using the interactive genome browser. Analyzed patient data may be published and made available to a community of users, which may communicate with one another.

28 Claims, 50 Drawing Sheets

(56) References Cited

U.S. PATENT DOCUMENTS

| | | | |
|---|---|---|---|
| 2005/0066276 | A1 | 3/2005 | Moore et al. |
| 2005/0074795 | A1* | 4/2005 | Hoffman et al. .................. 435/6 |
| 2006/0218182 | A1 | 9/2006 | Giffard et al. |
| 2008/0270041 | A1* | 10/2008 | Sproles et al. .................. 702/20 |
| 2009/0125248 | A1 | 5/2009 | Shams et al. |
| 2010/0094562 | A1* | 4/2010 | Shohat .......................... 702/19 |

OTHER PUBLICATIONS

CytoSure—lab set up "CytoSure", <<http://www.ogt.co.uk/products_cytosure-dt4.htm>>, retrieved on Jun. 30, 2009, 1 page.

Ensembl Genome Browser "e!Ensembl", <<http://www.ensembl.org/index.html>> retrived on Jun. 30, 2009, 2 pages.

NCBI "NCBI Map Viewer", <<http://www.ncbi.nlm.nih.gov/projects/mapview/map_search.cgi?taxid=9606>> retrieved on Jun. 30, 2009, 2 pages.

UCSC Geonome Browser Home "UCSC Genome Bioinformatics", <<http://genome.ucsc.edu/>> retrieved on Jun. 30, 2009, 3 pages.

Edgar, Robert C., "Muscle: Multiple Sequence Alignment with High Accuracy and High Throughput", Nucleic Acids Research, Mar. 19, 2004, vol. 32, No. 5, pp. 1792-1797.

Ludwig, Wolfgang, et al., "ARB: A Software Environment for Sequence Data", Nucleic Acids Research, Feb. 25, 2004, vol. 32, No. 4, pp. 1363-1371.

Non-Final Office for U.S. Appl. No. 12/613,978, mailed on Nov. 6, 2012, Brice Tebbs et al., "Interactive Genome Browser", 11 pages.

Final Office for U.S. Appl. No. 12/613,978, mailed on May 24, 2013, Brice Tebbs et al., "Interactive Genome Browser", 14 pages.

Office action for U.S. Appl. No. 12/265,396, mailed on Sep. 19, 2013, Bejjani et al., "Web-Based Genetics Analysis", 32 pages.

The Australian Office Action mailed Jan. 20, 2014 for Australian patent application No. 2009313292, a counterpart foreign application of U.S. Appl. No. 12/613,978, 3 pages.

Office Action mailed Dec. 11, 2014 in U.S. Appl. No. 12/613,978.

* cited by examiner

Fig. 9

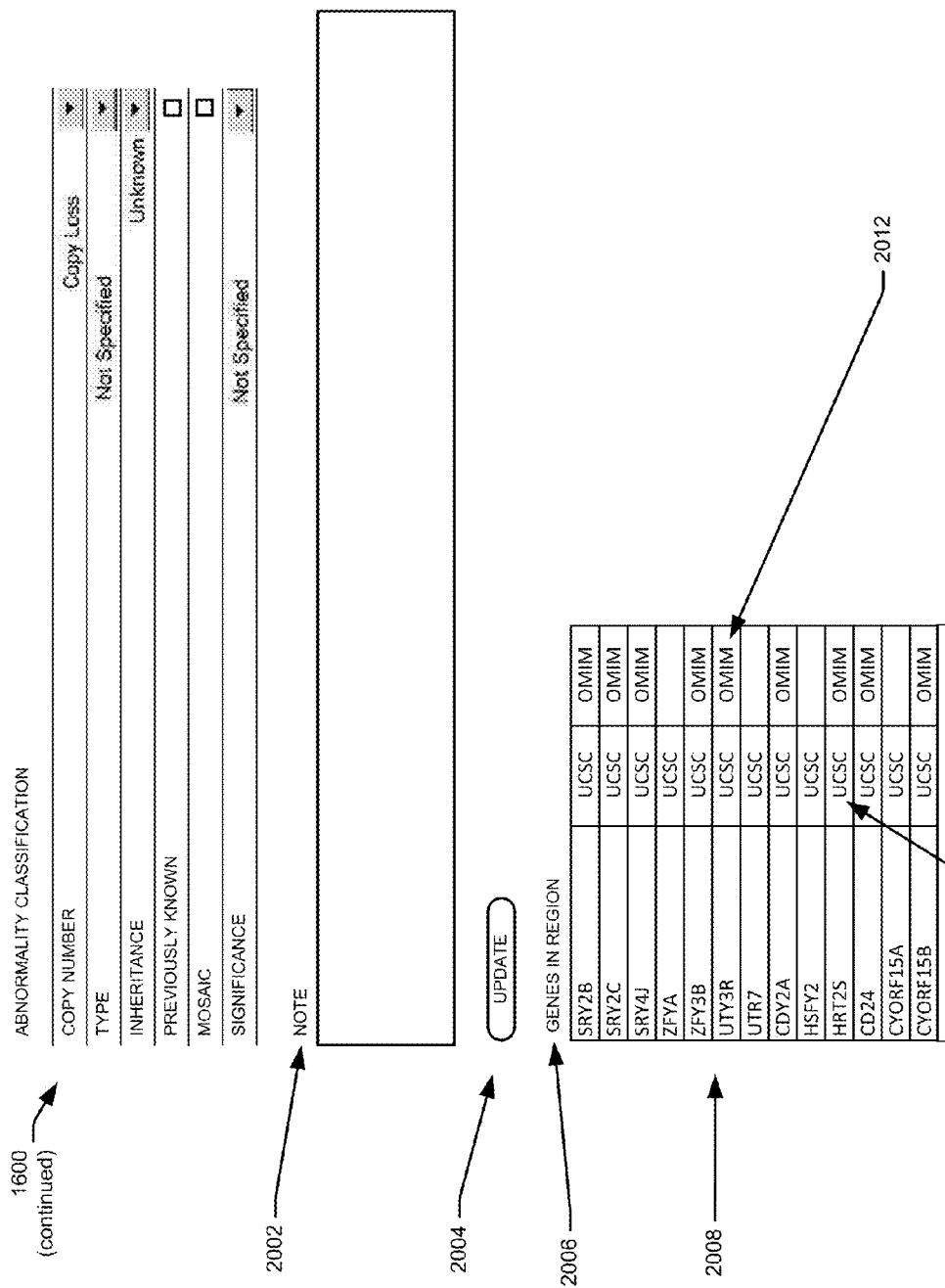

| | | |
|---|---|---|
| TMSB4Y | UCSC | OMIM |
| VCY | UCSC | OMIM |
| VCY1B | UCSC | |
| NLGN4Y | UCSC | OMIM |
| XKRY2 | UCSC | |
| XKRY2 | UCSC | OMIM |
| CDY2B | UCSC | |
| CDY2A | UCSC | OMIM |
| HSFY2 | UCSC | |
| HSFY1 | UCSC | OMIM |
| CD24 | UCSC | OMIM |
| CYORF15A | UCSC | OMIM |
| CYORF15B | UCSC | OMIM |
| JARID1D | UCSC | OMIM |
| EIF1AY | UCSC | OMIM |
| RPS4Y2 | UCSC | |
| RBMY1B | UCSC | |
| RBMY1A1 | UCSC | OMIM |
| RBMY1E | UCSC | |
| RBMY1D | UCSC | |
| PRY | UCSC | OMIM |
| PRY2 | UCSC | OMIM |
| RBMY1F | UCSC | |
| RBMY1J | UCSC | |
| BPY2 | UCSC | OMIM |
| BPY2C | UCSC | |
| BPY2B | UCSC | |
| DAZ1 | UCSC | OMIM |
| DAZ4 | UCSC | |
| DAZ2 | UCSC | OMIM |
| DAZ3 | UCSC | OMIM |
| CDY1B | UCSC | |
| CDY1 | UCSC | OMIM |

1600 (continued)

2102 → FISH PROBES IN REGION

3200 — PATIENT TORRELCO-EL-CHALUPA

3202

| PATIENT ID | TORRELCO-EL-CHALUPA |
|---|---|
| PATIENT DOB | 2008-01-01 |
| PHYSICIAN | ZOIDBERG |

3204 ANALYSIS RESULTS

| PLATFORM | SIGNATURECHIPWG™ V1.0.1 |
|---|---|
| CHIP ID #1 | 000034 |
| CHIP ID #1 | 000344 |
| NO. BAC CLONES | 4660 |
| NO. BAC CONTIGS | 1543 |
| ARRAY RESULT | RESULT WAS CLEARLY VISIBLE |
| FISH RESULTS | COPY GAIN WAS SHOWN |

3206

ANALYSIS SUMMARY

MICROARRAY ANALYSIS WAS PERFORMED ON THIS SPECIMEN USING THE SIGNATURECHIPWGTM V1.0.1 ARRAY MANUFACTURED BE SIGNATURE GENOMICS LABORATORIES, LLC. WHICH INCLUDES 4660 BAC CLONES IN 1543 CONTIGS. THERE WAS ONE ABNORMALITY OF POTENTIAL CLINICAL SIGNIFICANCE.

3208

ABNORMALITY 1 – UNKNOWN 159.88 KB COPY GAIN

THIS ABNORMALITY IS CHARACTERIZED BY A COPY GAIN OF 1 BAC CLONE(S) IN THE REGION OF UNKNOWN. THIS ABNORMALITY IS ESTIMATED TO BE A MINIMUM SIZE OF 159.88 KB AND A MAXIMUM SIZE OF 354.11 KB DUE TO GAPS IN THE REGIONS REPRESENTED ON THE MICROARRAY. PLEASE CONSULT THE CHART AND TABLE BELOW FOR MORE INFORMATION. THIS ABNORMALITY HAS BEEN CLASSIFIED AS A TERMINAL LOSS PARENTAL STUDIES INDICATE THAT THIS ABNORMALITY IS MATERNAL.

3210 GENOGLYPHIX GENOME BROWSER VIEW

3212

ABNORMALITY DETAILS

| COPY NUMBER | COPY GAIN |
|---|---|
| CHROMOSOME BAND | UNKNOWN |
| GENOMIC COORDINATES | CHRZ:30978766-31138643 |
| ESTIMATED MINIMUM SIZE | 159.88 KB |

| | |
|---|---|
| ESTIMATED MAXIMUM SIZE | 354.11KB |
| NUMBER OF BAC CLONES | 1 |
| STARTGAP | 194.23KB |
| ENDGAP | 0BP |

3302 — FULL ABNORMALITY LIST

| GENOMIC COORDINATES | BAND(S) | MINIMUM SIZE | COPY NUMBER | TYPE | INHERITANCE | SIGNIFICANCE | MOSAIC |
|---|---|---|---|---|---|---|---|
| CHRZ:30978766 -31138643 | UNKNOWN | 159.88KB | COPY GAIN | TERMINAL LOSS | MATERNAL | CLINICALLY SIGNIFICANT | NO |

3304 —

| GENOGLYPHIX DATABASE INFO | |
|---|---|
| REF SEQ GENES UPDATED ON | 10/10/2008 |
| SGL CNVS UPDATED ON | 07/04/2008 |
| GCAD UPDATED ON | 10/6/2008 |
| DVG UPDATED ON | 06/26/2008 |
| SGL GPS UPDATED ON | 11/5/2008 |
| FISH PROBES UPDATED ON | 10/20/2008 |

| | | |
|---|---|---|
| RBMY1D | UCSC | |
| PRY | UCSC | OMIM |
| PRY2 | UCSC | OMIM |
| RBMY1F | UCSC | |
| RBMY1J | UCSC | |
| BPY2 | UCSC | OMIM |
| BPY2C | UCSC | OMIM |
| BPY2B | UCSC | |
| DAZ1 | UCSC | |
| DAZ4 | UCSC | |
| DAZ2 | UCSC | OMIM |
| DAZ3 | UCSC | OMIM |
| CDY1B | UCSC | |
| CDY1 | UCSC | OMIM |

4600
(continued)

5002 — FISH PROBES IN REGION
RP11-63907
RP11-975F3
RP11-737L10
RP11-400O10
RP11-515L2
RP11-414C23
RP11-19616
RP11-475P15
RP11-693P14

Fig. 50

INTERACTIVE GENOME BROWSER

PRIORITY AND RELATED APPLICATION

The present application claims priority to and is related to U.S. Provisional Application Ser. No. 61/113,131, entitled, "Interactive Genome Browser" filed on Nov. 10, 2008; which is incorporated by reference herein for all that it teaches and discloses.

BACKGROUND

Chromosomes are organized structures of DNA and protein and are present in nearly every cell in our body. Each chromosome contains hundreds of genes that determine many of our exhibited personal traits, such as eye color, hair color and the like. Typically, humans have two sets of twenty-three chromosomes, one set of which is acquired from our mother and the other of which is acquired from our father.

While humans ordinarily have two copies of each autosomal region, this may vary for particular genetic regions due to DNA copy loss or gain. Many times, such loss or gain is normal and does not adversely affect the person. Unfortunately, other times such loss or gain is associated with a genetic syndrome or disorder. For instance, Down syndrome (or Trisomy 21) is a genetic disorder that is caused by the presence of some or all of an extra twenty-first chromosome. Other genetic disorders that are caused by chromosomal DNA copy loss or gain include, among others, Cri du chat, Wolf-Hirschhorn syndrome, Edward's syndrome, Jacobsen syndrome and Turner syndrome.

Currently, over 100 regions of human chromosomes are known to be associated with well-described genetic syndromes that are caused by DNA copy loss or gain. Many of these imbalances are sub-microscopic, which requires the use of complex technologies to detect these imbalances in a patient's genome. One such technology, known as array-based comparative genomic hybridization ("array CGH" or "aCGH"), has proven effective at allowing researchers, doctors and clinicians to rapidly evaluate chromosomal segment losses and gains.

To perform array CGH, a doctor or clinician extracts DNA from a patient sample. This DNA is then tagged with a fluorescent dye. A control sample from another person, meanwhile, is also prepared and tagged with a fluorescent dye of a different color. This control sample is typically taken from a person who does not exhibit any traits of a genetic disorder or syndrome. That is, the control sample should typically comprise a representation of a "normal" genome. At this point, the patient DNA and the control DNA are mixed together on a microscope slide (known as a "microarray slide") that may have, for instance, thousands of regions of chromosomes represented as dots on the slide. Each of these dots contains unique fragments of DNA from a particular section of each chromosome.

Once the patient and control DNA are applied to the microarray slide, fragments of the patient and control DNA compete to attach (or "hybridize") to the DNA fragments in each dot of the microarray slide. For each location on the slide, if the patient DNA does not have a gain or a loss, then the patient DNA should compete equally with the control DNA (assuming that the control DNA also does not have a gain or a loss at that location). If, however, the patient DNA has a loss at that location, then the control DNA will hybridize to the DNA fragment to a greater degree than will the patient DNA. Conversely, if the patient DNA has a gain, then the patient DNA will hybridize to the DNA fragment to a greater degree than will the control DNA.

After hybridization occurs, the microarray slide may be placed in a scanner that measures the fluorescent signals of each microarray dot. In instances where the patient and the control compete equally, the distinct fluorescent colors will result in the appearance of a color that reflects equal dosage of the two colors. In instances where a patient has a loss, however, the scan will result in the predominance of the fluorescent color with which the control DNA was tagged. Conversely, where the patient DNA has a gain, the scan will result in the predominance of the fluorescent color with which the patient DNA was tagged. With this information, a doctor or a clinician may determine where the patient has chromosomal segments gains and/or losses. Furthermore, with this knowledge, the doctor or clinician may formulate or verify a diagnosis for the patient. For instance, the doctor or clinician may use this information to verify (to a higher degree of certainty) that a particular patient does indeed have Down syndrome.

Given ongoing research as well as application in clinical settings, different users may make use of different terminology. For example, "patient" and "study subject" are considered synonymous, with the distinction being point of view. Researchers typically refer to an individual under investigation as a "study subject" while doctors and clinicians refer to the individual under investigation as a "patient." Similarly, a researcher may generate "experimental results" on the study subject while doctors and clinicians generate "test results" on a patient.

While array CGH and other technologies have drastically improved clinician's ability to detect DNA copy gains and losses, a need exists to leverage previously-accumulated knowledge and experience.

SUMMARY

This document describes techniques for allowing researchers, doctors, clinicians, and other users to view and manipulate large amounts of genetic data in an interactive genome browser executing within a user's web browser application or other application.

Users may utilize the interactive genome browser to view a patient experiment data track for a patient and other genetic data tracks ("tracks"). Tracks are aligned by base pair with the patient experiment data track and may be provided for display to a user. A user may annotate and/or compare data tracks from private and community databases. During analysis, additional genetic tests may be ordered quickly from an aligned data track displaying available tests. A user may search genomic data using the interactive browser, leveraging the alignment of the tracks and the extensive private and community databases.

Once the user has analyzed a patient's information, a report may be automatically generated using data acquired during the analysis within the interactive genome browser. Analytical results as well as patient genetic data may then be published by a user to the community database. The publisher (or their affiliate) may choose to be accessible for consultation with regards to the published data. Published data may be rendered anonymous to protect patient confidentiality. Anonymous contact between users is also supported.

This combination of speed, access, presentation, reporting, and community collaboration generates significant opportunities for users to more accurately and quickly complete complicated genetic analysis.

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. The term "techniques," for instance, may refer to system(s), method(s) and/or computer-readable instructions as permitted by the context above and throughout the document.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical items.

FIG. 9 illustrates additional genetic data tracks ("tracks") available for display in the interactive genome browser of FIG. 8.

FIG. 20 illustrates additional details available in the detailed view of FIG. 16, including an area for a user to enter notes, and a display of genes in the region displayed and links for those genes to external databases. An external database is distinct from the genetic information database 114 of a host server for the interactive genome browser.

FIG. 21 illustrates additional details available in the detailed view of FIG. 16, including a listing of fluorescent in-situ hybridization ("FISH") probes in the region.

FIG. 29 illustrates the final review interface of FIG. 28 after updating information.

FIG. 32 illustrates a report automatically generated using information entered by the user.

FIG. 33 illustrates additional data which may be presented in the report of FIG. 32.

FIG. 45 illustrates a partial listing of results from the search of FIG. 43.

FIG. 47 illustrates the additional detailed information from FIG. 46 including an additional genetic data track for abnormal regions.

FIG. 50 illustrates additional details available in the detailed view of FIG. 46, including a listing of FISH probes in the region.

DETAILED DESCRIPTION

Figure 1:
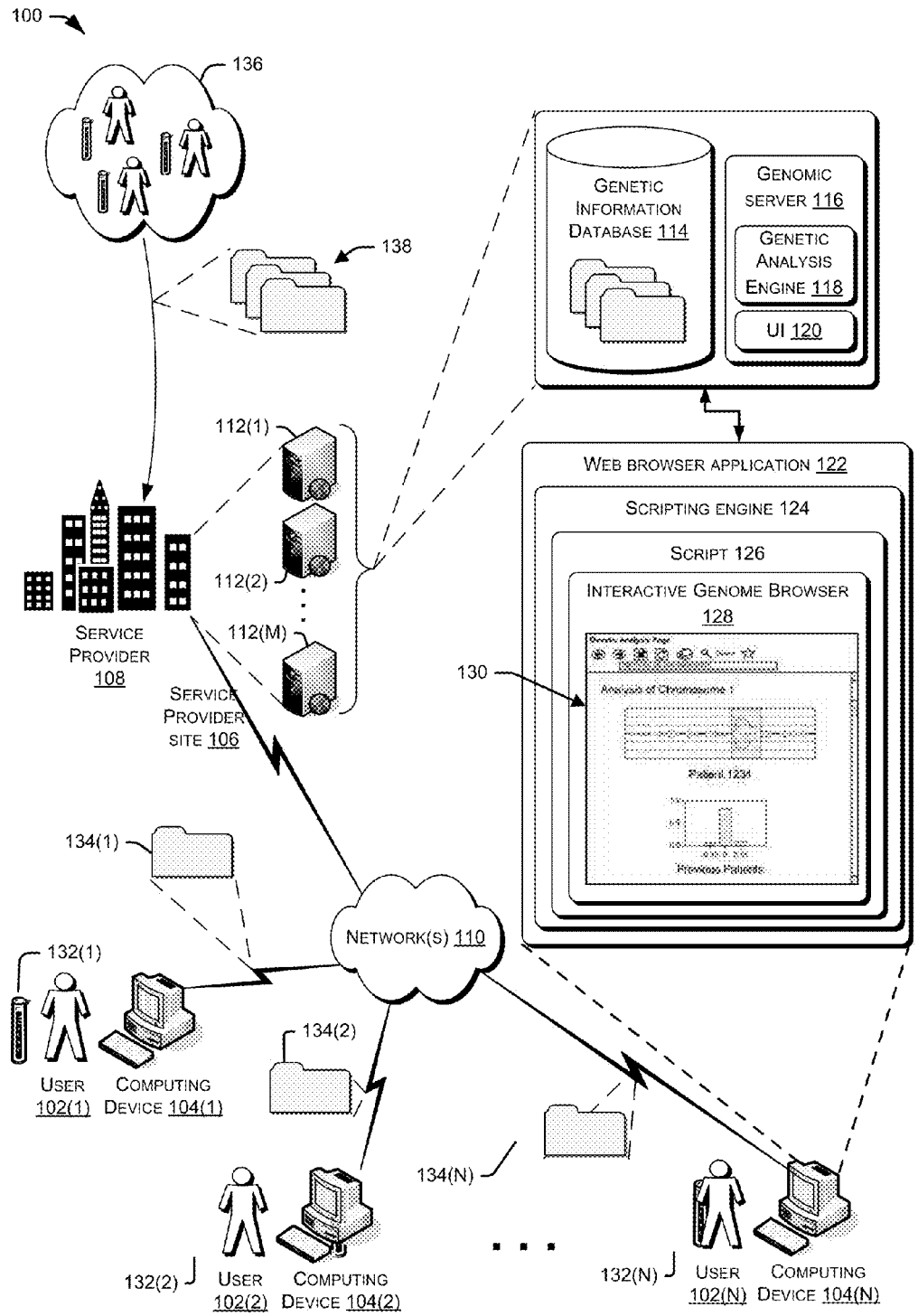
FIG. 1 illustrates an example architecture that includes a site to host genetic information that is accessible by multiple users via a network and using an interactive genome browser.

This disclosure is directed to an interactive genome browser, executing within a web browser application. A genome server ("server") provides a script, applet, or other application ("script") configured to execute within a scripting engine of the web browser application or virtual machine and display the interactive genome browser. By combining the accessibility of vast amounts of genomic data stored on a server with the ease of distribution and responsiveness of script executing within a browser, complicated and large sets of genomic data may be viewed and manipulated in a highly interactive and responsive format.

Users, including researchers, doctors and clinicians, may view and manipulate genetic data in the interactive genome browser. Patient genetic data comprising experiment results may be displayed in graphical form in a patient track, and additional genetic data tracks may be added to the browser display. These additional genetic data tracks are aligned with the patient track, the alignment being a correspondence between base pairs of the tracks. Thus, as a user moves through the patient genome, the additional genetic data tracks are updated to display corresponding data. Additional data tracks may include a proprietary database of previously gathered genetic data, genetic data from a relative of the patient, information considered of clinical significance and published by users to a community, available genetic tests, and links to external databases for additional information. Users may also include annotations in an annotation data track, create customized data tracks, and view data tracks from other patients.

Alignment of the patient track with additional tracks may take place on the genome server with aligned data sent to the interactive genome browser, or alignment may take place in the interactive genome browser. When aligning within the interactive genome browser, track data is sent from the server to the interactive genome browser. This track data may comprise base pair genomic coordinates, which may be interpreted by the interactive genome browser. Scaling and translation of the tracks for display may then occur in the interactive genome browser.

Once the user has completed analysis of genetic features such as abnormalities, a report may be automatically generated.

The interactive genome browser facilitates searching enormous amounts of genetic data. For example, selection of a region of interest by the user may pre-populate a search form with a genomic location of the selection. Searches may also be filtered in different combinations to access all data in the database, community data, data from a user's patients, chromosomal location, disorder, symptom, clinical sign, indication for study, etc.

The described techniques may be implemented in a number of ways and in a number of contexts. One example implementation and context is provided with reference to the following figures, as described below in more detail. It is to be appreciated, however, that the following implementation and context is but one of many.

Illustrative Environment and System Architecture

FIG. 1 illustrates an example architecture 100 in which the described techniques for leveraging previously-accumulated knowledge and experience for diagnosing chromosomal syndromes may be implemented. Here, the techniques are described in the context of a site hosted by a service provider in combination with an interactive genome browser executing within a web browser executing on a user's computing device. It is to be appreciated, however, that the described techniques may be implemented in a vast number of other contexts and environments.

In architecture 100, one or more representative users 102(1), 102(2), . . . , 102(N) employ user computing devices 104(1), 104(2), . . . , 104(N) to access a representative service provider site 106 associated with a service provider 108. Users 102(1)-(N) may include doctors, clinicians, health care professionals, researchers, patients, or any other person interested in providing and/or analyzing genetic data. Service provider 108, meanwhile, may be a business or other entity that hosts or otherwise operates site 106 for the purpose of allowing users 102(1)-(N) the ability to upload and research genetic data. Site 106 may comprise any sort of site that supports user interaction, such as a website accessible over the Internet. Site 106 may also comprise a proprietary site that receives requests and provides content over proprietary networks other than the Internet and public web. Furthermore, in some instances, service provider 108 may not operate a site, but may somehow otherwise make available the described application(s) and database(s) to users 102(1)-(N) over a network.

As illustrated, a user (such as user 102(1)) accesses site 106 of service provider 108 via a network 110. Network 110 may include any one or combination of multiple different types of networks, such as cable television networks, the Internet, and wireless networks. User computing device 104, meanwhile, may be implemented as any number of computing devices, including as a remote terminal accessing a server, a personal computer, a laptop computer, a portable digital assistant (PDA), a cell phone, a set-top box, a game console, a personal media player (PMP), and so forth. User computing device 104 is typically equipped with one or more processors and memory to store applications and data. An application, such as browser or other client application, running on device 104 facilitates access to site 106 over network 110.

Site 106, meanwhile, is hosted on one or more servers 112(1), 112(2), . . . , 112(M) having processing and storage capabilities. In one implementation, the servers might be arranged in a cluster or as a server farm, although other server architectures may also be used to host the site. The site is capable of handling requests from many users and serving, in response, various pages of content that can be rendered at user computing devices 104(1)-(N) for viewing by user 102(1)-(N). This rendering involves more than a mere display of a web page. Rendering includes the use of an interactive genome browser executing within a web browser application. This interactive genome browser permits responsiveness and flexibility for user interaction by reducing the constant back-and-forth present in traditional page serving. Furthermore, it is noted that while the proceeding discussion describes the techniques with reference to pages, it is to be appreciated that the described techniques are equally applicable to other types of user interfaces (UIs). That is, the described techniques may apply to any sort of interface that includes visual content.

As illustrated, servers 112(1)-(M) host a genetic information database 114, as well as a genomic server 116. Genetic information database 114 stores data about multiple patients. As discussed in detail below, this stored data may be uploaded by a plurality of users at a plurality of locations (e.g., users 102(1)-(N)), as well as by service provider 108. As such, genetic information database 114 stores a multitude of patient data for use in leveraging previously-acquired knowledge and experience associated with the stored data.

Genomic server 116, meanwhile, may comprise a server application that includes a genetic analysis engine 118 and a user interface (UI) component 120. Genetic analysis engine 118 may analyze the patient data stored in genetic information database 114 for use in calculating statistics regarding this data. For instance, engine 118 may determine, for each autosomal region, how often patients associated with this data have exhibited chromosomal gain or loss. Engine 118 may also store notations about particular pieces of stored genetic data, which again may be provided by users 102(1)-(N) and/or by service provider 108.

User interface component 120, meanwhile, functions to output the information provided by analysis engine 118 for rendering on user computing devices 104(1)-(N). Furthermore, UI component 120 may also output for rendering information about a particular patient's data. This information may include, for instance, a visual representation (e.g., a plot) of some or all of the genome for a particular patient, uploaded by one of users 102(1)-(N) or by service provider 108.

Computing device 104(1) . . . (N) executes a web browser application 122. This web browser application comprises a scripting engine 124, virtual machine, or the like. Genomic server 116 serves a script 126, applet, or other executable component to a user upon request from the user. When script 126 is executed, the interactive genome browser 128 may be presented to the user, displaying an interface, such as illustrated page 130.

As illustrated, page 130 includes both a visual representation of chromosomal DNA copy number gain or loss for chromosome 1 of a particular patient, as well as statistics about previously-uploaded patient data, as calculated by genetic analysis engine 118. For instance and as illustrated, page 130 may include the plot of the particular patient's data, as well as statistics depicting how often chromosomal copy loss or gain have been found in the previously-uploaded patient data. Of course, while FIG. 1 illustrates an illustrative page 130, site 106 may serve multiple other pages, as illustrated and described below and otherwise.

With this architecture in mind, FIG. 1 further illustrates that users 102(1)-(N) may analyze a respective patient sample 132(1), 132(2), . . . , 132(N) to determine corresponding patient data 134(1), 134(2), . . . , (N). For instance, users 102(1)-(N) may each utilize a particular laboratory (in fact, each may utilize a different laboratory) to perform array CGH or CGH testing on patient samples 132(1)-(N). Additionally or alternatively, users 102(1)-(N) may employ a different form of genetic testing array-based or otherwise that does not involve CGH. In either instance, this testing may somehow describe or illustrate chromosomal segment loss and/or gain, information about single nucleotide polymorphisms (SNPs), sequence information generally, or any other type of genetic data including regions of loss of heterozygosity (LOH) for some or all of a corresponding patient's genome. Users 102(1)-(N) may then upload patient data 134(1)-(N) to genetic information database 114 via computing devices 104(1)-(N). Furthermore, in some instances, users 102(1)-(N) may upload genetic data without having performed any sort of tests. In these instances, this data may have been previously compiled by another entity.

Once these data have been uploaded, each of users 102(1)-(N) may then operate, at a corresponding computing device 104(1)-(N), interactive genome browser application 128. For instance, these users may use application 128 to compare their uploaded data against previously-uploaded data in hopes of better diagnosing a subject/patient.

To illustrate, user 102(1) may upload patient data 134(1) in order to compare uploaded patient data against previously-uploaded data associated with multiple other patients. User 102(1), who may be a doctor or a clinician, may then determine that while his or her patient does indeed show a chromosomal DNA copy loss or gain at a particular location, the previously-uploaded information shows that such a loss or gain is commonly found without adverse affects among many people. Conversely, user 102(1) may learn, via application 128, that his or her patient's DNA copy loss or gain occurs at a location that is commonly associated with a particular genetic syndrome. In either instance, user 102(1) is able to leverage previously-accumulated knowledge and is able to better serve his or her patient.

While each of users 102(1)-(N) may perform the genetic testing (e.g., array CGH) of patient samples 132(1)-(N), in some embodiments these users may also choose to have service provider 108 directly perform this testing. For instance, user 102(1) may physically send patient sample 132(1) to service provider 108. One or more representatives 136 (e.g., doctors, clinicians, etc.) of service provider 108 may then perform the testing of sample 132(1) to create patient data 134(1).

Service provider 108 may then either provide this data to user 102(1), who may then upload the data to site 106 and database 114, or service provider 108 may directly upload data 134(1) to database 114. User 102(1) may then navigate to site 106 to analyze data 134(1) along with the previously-uploaded patient data. As illustrated, FIG. 1 depicts that representatives 136 of service provider 108 test patient samples to create a set of patient data 138 for uploading to the genetic information database 114.

Figure 2:
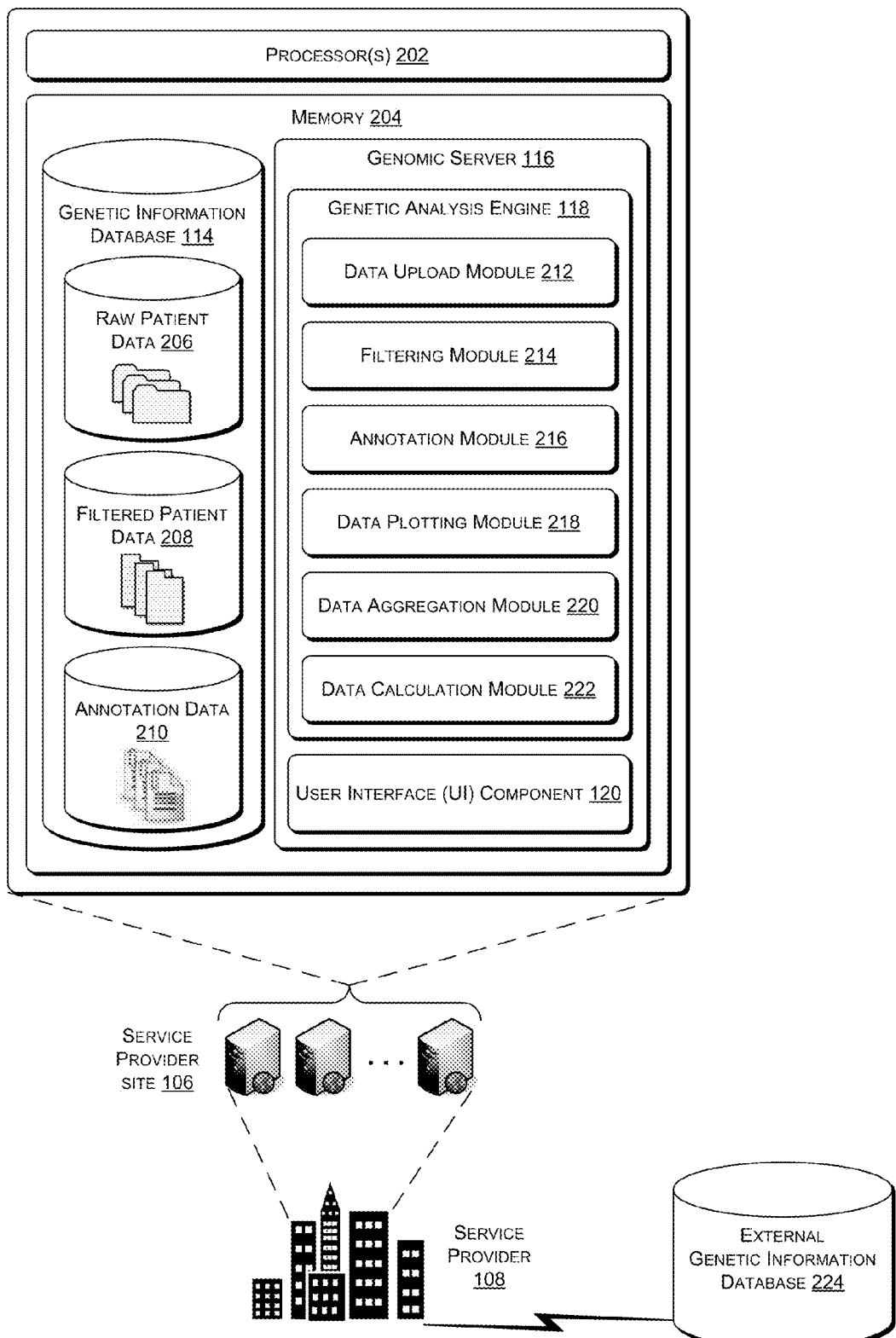
FIG. 2 illustrates example components of the site of FIG. 1 which hosts genetic information.

FIG. 2 depicts illustrative components of the site of FIG. 1 which hosts genetic information. As illustrated, servers 112 (1)-(M) of site 106 include processors 202 and memory 204, which stores database 114 and genomic server 116.

In some implementations, genetic information database 114 includes raw patient data 206, filtered patient data 208 and notation data 210. While this data may be stored in database 114 in some instances, in other instances each of these types of data may be stored in separate and distinct databases. Raw patient data 206 comprise data that have been uploaded by users (e.g., users 102(1)-(N) and representatives 128) before site 106 has processed the data. Filtered patient data 208, meanwhile, may comprise patient data that site 106 has processed. For instance, while raw patient data 206 may include all or substantially all of the information learned during the genetic testing (such as array CGH), filtered patient data 208 may include only the information regarding chromosomal DNA copy loss or gain. Finally, notation data 210 may include notations made by users (e.g., users 102(1)-(N) and representatives 128) or by some external entity, such as a remote database that provides information regarding genetic syndromes.

Next, genomic server 116 includes genetic analysis engine 118 and UI component 120. Genetic analysis engine 118, meanwhile, may include a data upload module 212, a filtering module 214, a notation module 216, a data plotting module 218, a data aggregating module 220, and a data comparator module 222.

Data upload module 212 functions to allow users (e.g., users 102(1)-(N) and representatives 136) to upload raw patient data (e.g., patient data 134(1)-(N) and patient data 138) to genetic information database 114. Specifically, module 212 allows these users to upload this data to a database or a location in database 114 that stores raw patient data 206. Filtering module 214 then functions to filter this uploaded raw patient data 206. For instance, module 214 may filter out information that does not identify a chromosomal DNA copy loss or gain. As such, module 214 may create filtered patient data 208 that generally only includes those regions that may contain a chromosomal abnormality. Of course, in some instances, engine 118 may not filter this data, in which case database 114 may store raw patient data 206 but not filtered patient data 208.

In some instances, patient samples 132(1)-(N) are placed onto array CGH or CGH slides in the form of bacterial artificial chromosome (BAC) arrays. A contig is a set of contiguous overlapping DNA segments. Stated another way, a contig is a set of overlapping DNA segments that, when considered together, covers or represents a contiguous segment of DNA that represents a locus in a genome. In other instances, patient samples 132(1)-(N) are hybridized onto microarray slides that have been manufactured in the form of oligonucleotide (oligo) arrays. While both BAC and oligo arrays tend to be successful in enabling identification of losses and gains, oligo arrays tend to identify smaller segments of DNA copy gain or loss due to the fact that they represent smaller regions of a chromosome (approximately 25-60 nucleotides, as compared to 150,000-250,000 in the case of BACs). Furthermore, because oligo arrays comprise smaller regions of a chromosome than compared to BAC arrays, oligo arrays tend to include many more spots than BAC arrays. For instance, a slide comprising an oligo array may include approximately 105,000 spots, while BAC array slide may include approximately 4,700 spots. Because of the large number of spots that comprise an oligo array, patient data garnered from these arrays tend to be much larger than data garnered from BAC arrays.

Therefore, in some instances filtering module 214 may filter out patient data that is based on oligo arrays, but not patient data that is based on BAC arrays. Specifically, genetic information database 114 may store all or substantially all of the information uploaded for a BAC array, while only storing the regions of potential DNA copy losses or gains as filtered by module 214 for oligo arrays.

In addition to data upload module 212 and filtering module 214, genetic analysis engine 218 includes data plotting module 216. Data plotting module 216 functions to receive patient data (e.g., stored as raw patient data 206 or filtered patient data 208) and create a plot for the data. This plot may indicate, for instance, a degree of chromosomal segment loss or gain for some or all of the uploaded chromosome information. Furthermore, module 218 may create a plot for the entirety of the corresponding patient data, as well as plots for smaller pieces of this data. For instance, module 218 may create plots for each chromosome associated with the uploaded data.

Next, data aggregation module 220 functions to aggregate previously-uploaded patient data based on requests made by a user of application 128. For instance, if a user (e.g., user 102(1)) wishes to view his or her patient data at chromosome 1, data aggregation module 220 may aggregate information about chromosome 1 based on the previously-uploaded patient data. Data calculation module 222 may then calculate statistics regarding this aggregated data. For instance, module 222 may determine (and output for the user) statistics indicating how often chromosomal DNA copy losses and/or gains have been found in the aggregated data for chromosome 1 or for some portion of chromosome 1.

If, for instance, user 102(1) wishes to focus on a particular portion of chromosome 1 associated with his or her patient (e.g., a portion that appears, according to the plot, to have a DNA copy gain or loss), then data aggregation module 220 may aggregate corresponding data and data calculation module 222 may calculate statistics about gain or loss previously seen at this location. Of course, while one specific type of statistics has been discussed, data calculation module 222 may similarly calculate any other type of statistics regarding the previously-uploaded data.

Finally and as discussed above, UI component 120 functions, at least in part, to receive the created plots, notations and calculated statistics for creation of one or more user interfaces. User interface component 120 may output this and other data for the rendering of page 130 illustrated in FIG. 1, as well as for multiple other pages and UIs including those discussed below.

Illustrative Display of Chromosomal Data

Figure 3:
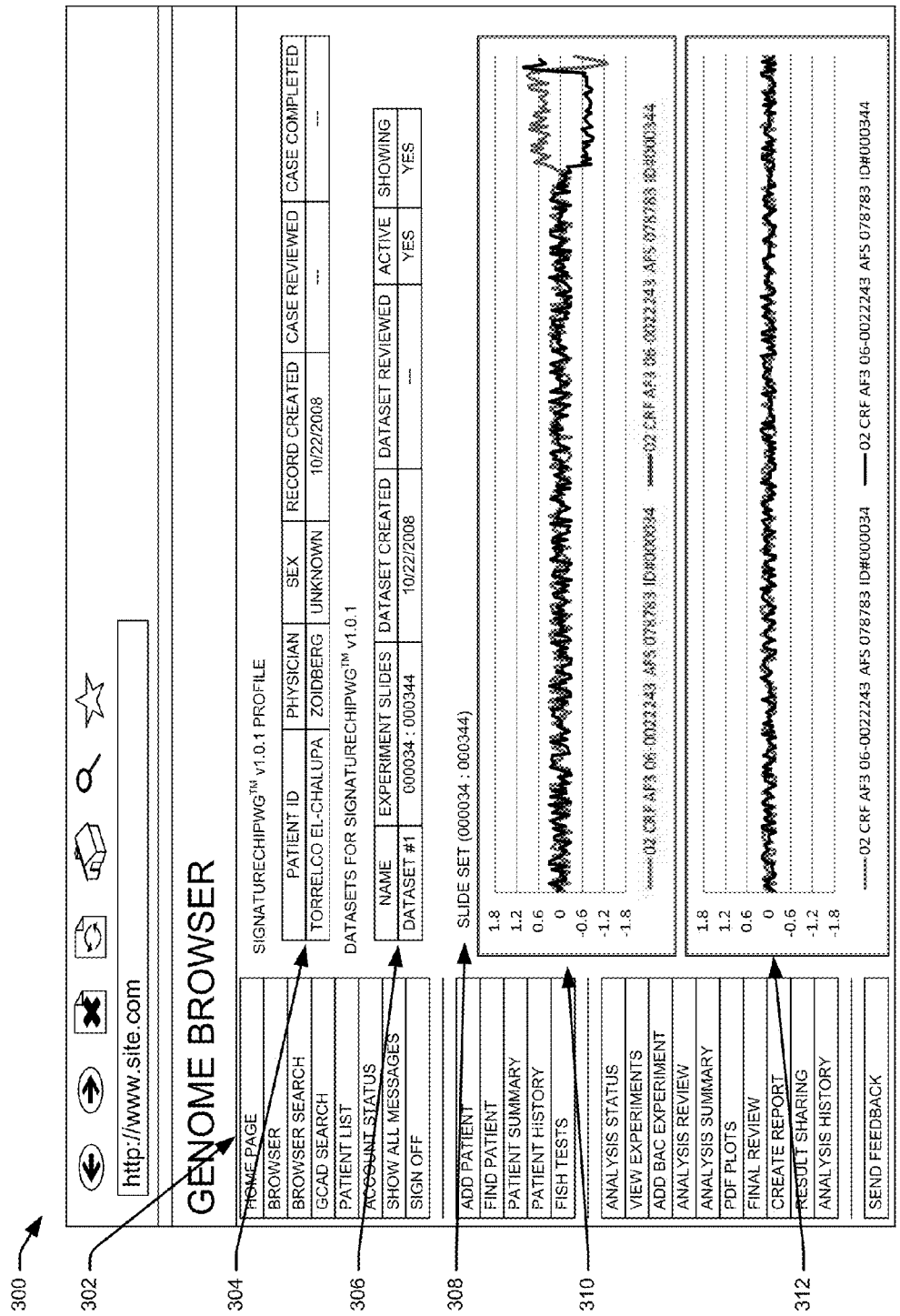
FIG. 3 illustrates a view of array CGH slide sets available after selection of a patient.

FIG. 3 illustrates a view 300 of array CGH slide sets available after selection of a patient. Displayed is a navigation bar 302 of options available to a user including the browser, browser search, GCAD search, patient list, account status, show all messages, find a patient, patient summary, patient history, FISH tests, analysis status, view experiments, add BAC experiment, analysis review, PDF plots, final review, create report, result sharing, and analysis history. Each of these tracks is discussed in depth below.

Patient data 304 may be displayed, including patient identification, physician, sex, date the record was created, review date, and case completion date. A listing of datasets 306 are also displayed, indicating the name of the dataset, experiment slides, date dataset created, date dataset reviewed, whether the dataset is active or inactive, and if to be shown or not. A set of slides 308 are also displayed showing various charts 310 of the patient's whole genome 310. Each chromosome, for example chromosome 1 shown at 312, may also be displayed.

Figure 4:
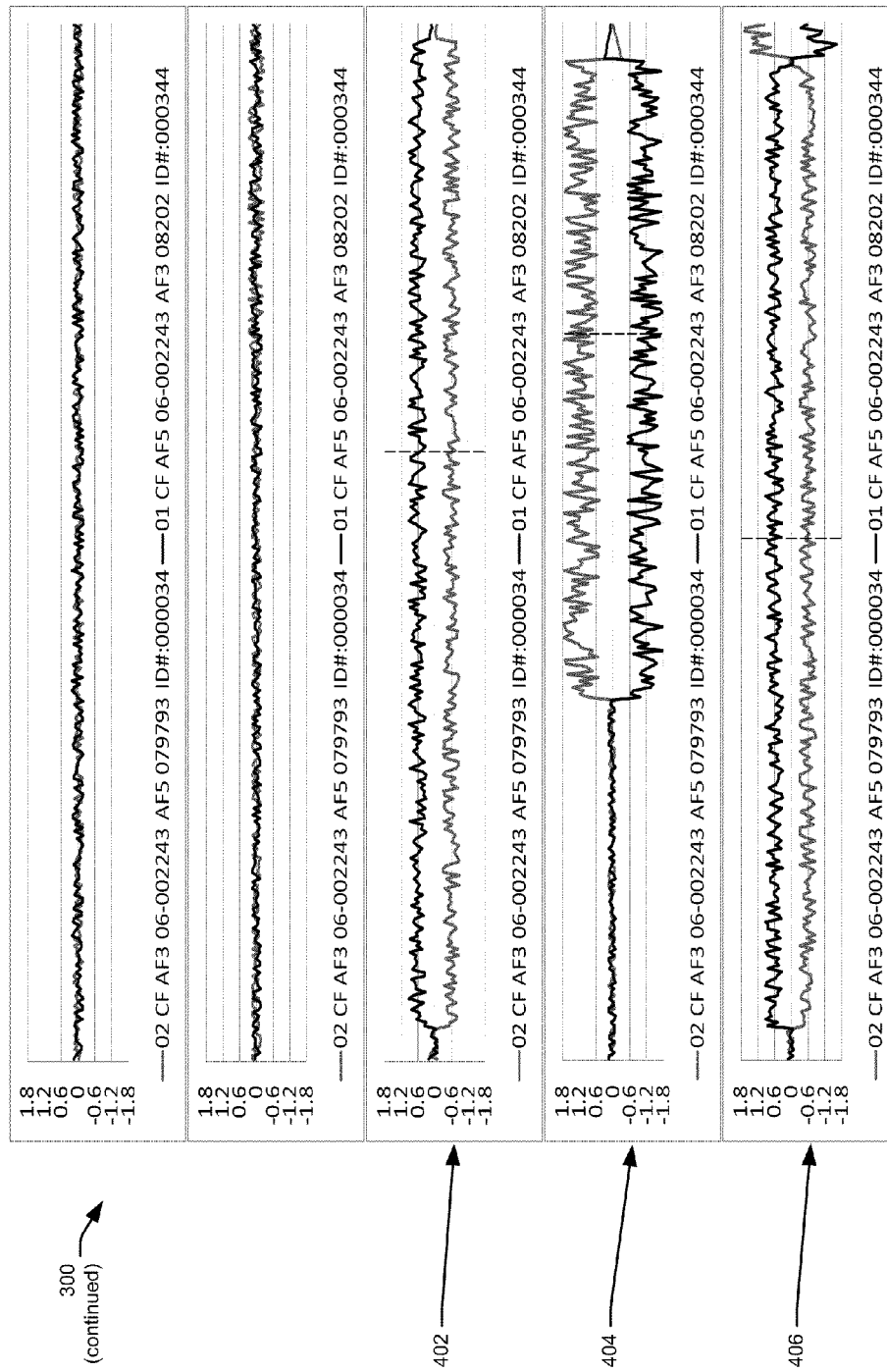
FIG. 4 illustrates a view of the array CGH slide sets illustrated in FIG. 3 and showing an X chromosome (402), a Y chromosome (404), and both chromosomes (406).

FIG. 4 illustrates a of the array CGH slide sets 300 of FIG. 3 and shows a chart of an X chromosome 402, a chart of a Y chromosome 404, and an X & Y chart 406.

Illustrative Display of a Specific Chromosome

Figure 5:
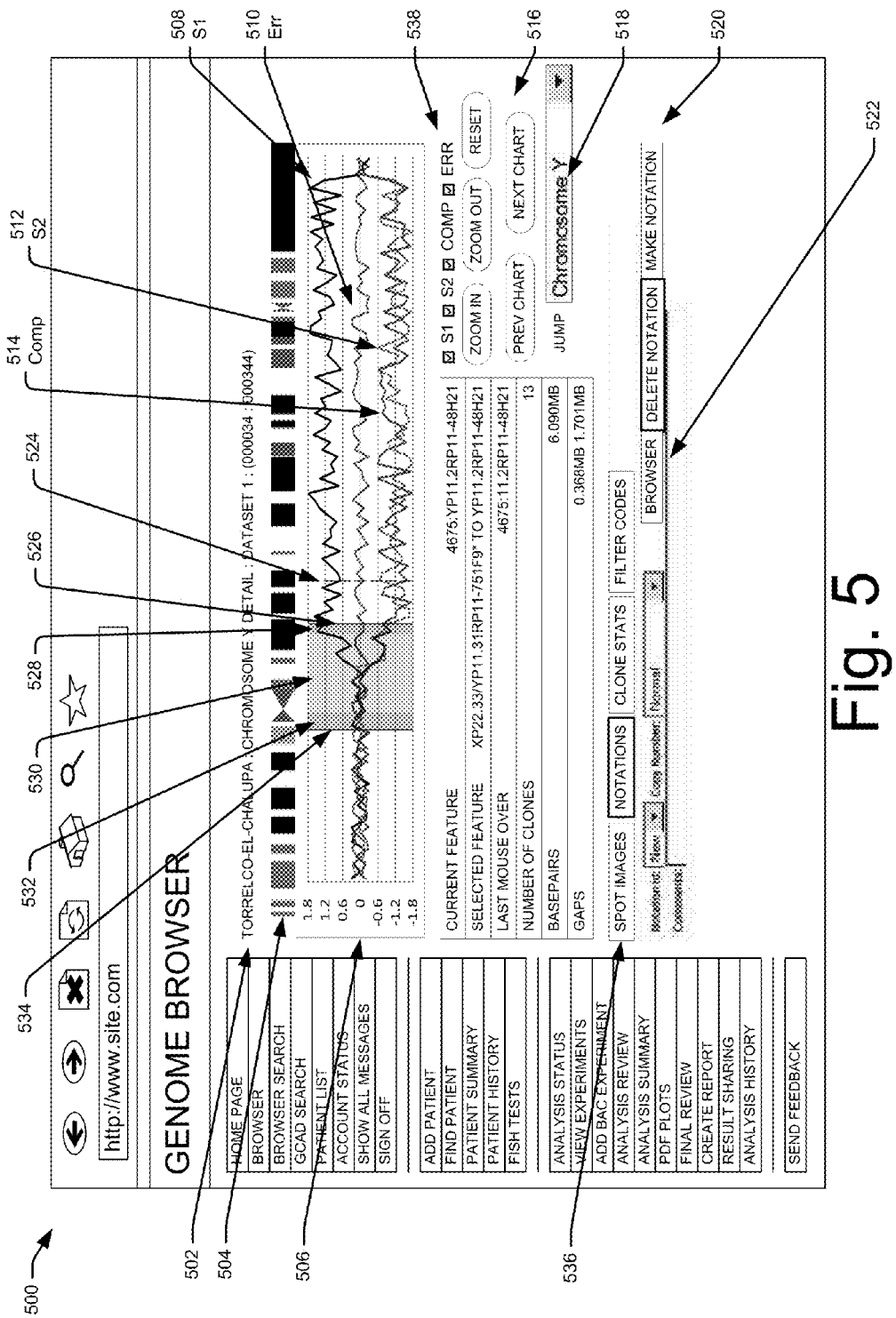
FIG. 5 illustrates a detail view of data for the Y chromosome of FIG. 4 after selection.

FIG. 5 illustrates a detail view 500 of data for the Y chromosome 404 of FIG. 4 after selection. A title header 502 displays patient information, chromosome, and dataset name. A large scale chromosome ideogram 504 may be displayed to provide orientation for the user. A BAC plot 506 displays the layout of the uploaded BAC clones for the particular patient, the gap there between, coverage of the corresponding genes, the copy number variance that service provider site 106 has tracked for the specified location of the genome, information about copy number variance as provided by one or more public databases, and segmental duplications (i.e., low-copy repeats) in the human genome. A copy number variance (CNV) is any DNA segment, longer than 1 kb, with a variable copy number compared with a reference genome. Feuk et al. Nat Rev Genet 7,85-97 (2006).

Within this BAC plot 506 S1 data 508, Err data 510, S2 data 512, and Comp data 514. S1 indicates data from a first experiment, S2 the dye swap experiment, Err is the error, or disagreement, between S1 and S2, and Comp is a composite of Si and S2 made by inverting one and averaging the results. A jump 518 pull down allows an easy change to other chromosomes in the dataset. A user may make a notation 520 for the displayed data using the notation section of the options menu 536. Options menu 536 comprises notations, spot images, clone stats, and filter codes.

A browser view 522 of the patient data may be initiated. The centromere of the sample 524 may be displayed, as is a left edge 534 and a right edge 526 of a region of interest 530. An additional shaded area 532 extends from the left edge 534 towards the right edge 526 and another shaded area 528 extends from the right edge 526 towards the left edge 534, where the shaded areas indicate the contigs are the start and end of the region. This shading allows the user to gauge about close together the clones are in a genome.

Figure 6:
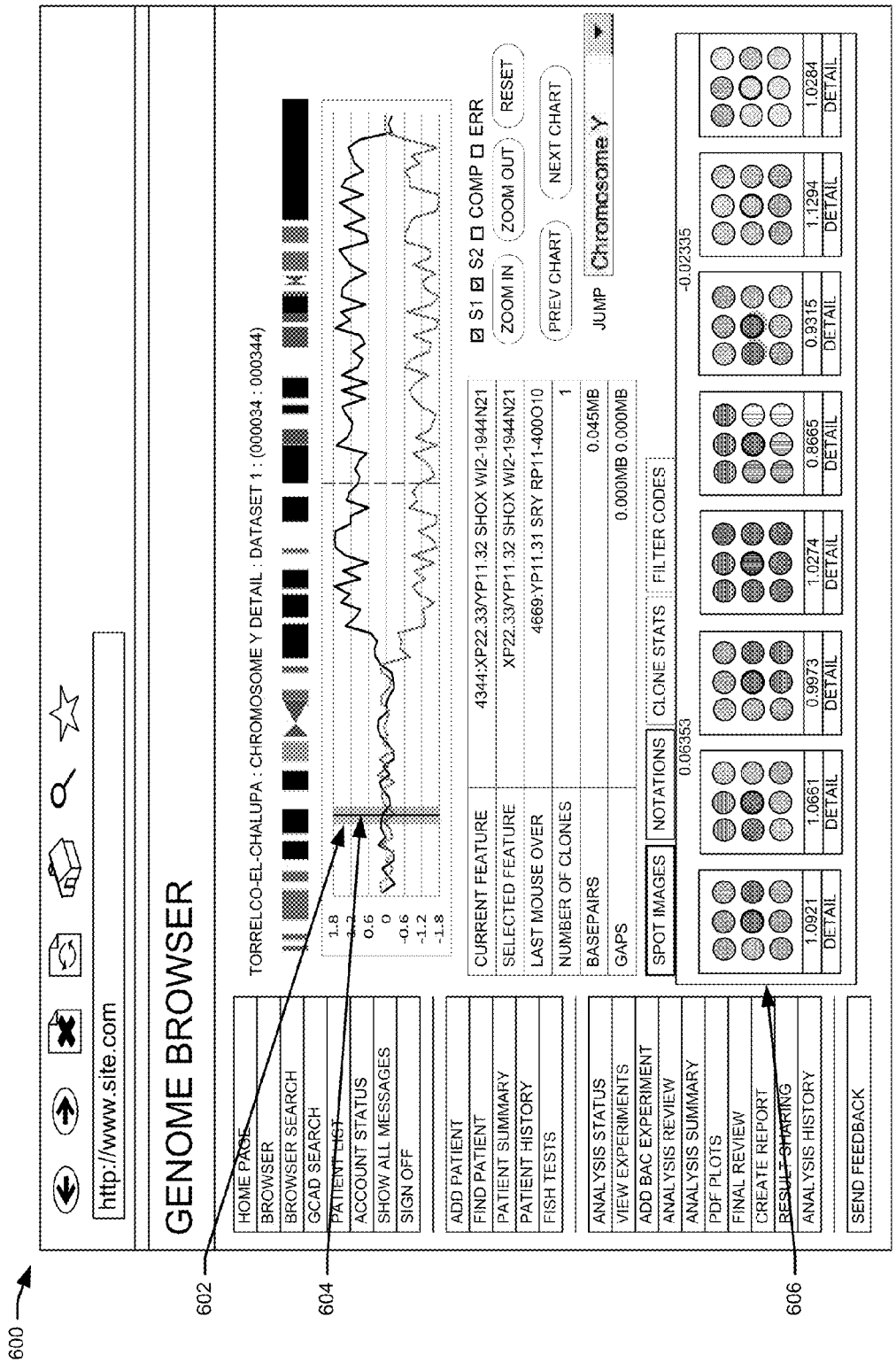
FIG. 6 illustrates another view of FIG. 4 showing varying shading to indicate different Bacterial Artificial Chromosome (BAC) contigs boundaries around a point of interest, as well as spot images from a dataset of the slides.

FIG. 6 illustrates another view of FIG. 4 showing varying shading to indicate different contig boundaries 602 around a point of interest. Displaying the contig boundaries informs the user about the specific location of the breakpoint where the DNA copy number change occurred, gives information on whether there is a gap in coverage of the genome in the array, and as such guides the interpretation of the abnormality. The option menu 536 has also been selected to display spot images 606 from a dataset of the slides. Display of spot images provides the user with additional information, and the opportunity to personally assess data which may have been generated by an automated system.

Illustrative Interactive Genome Browser Display

Figure 7:
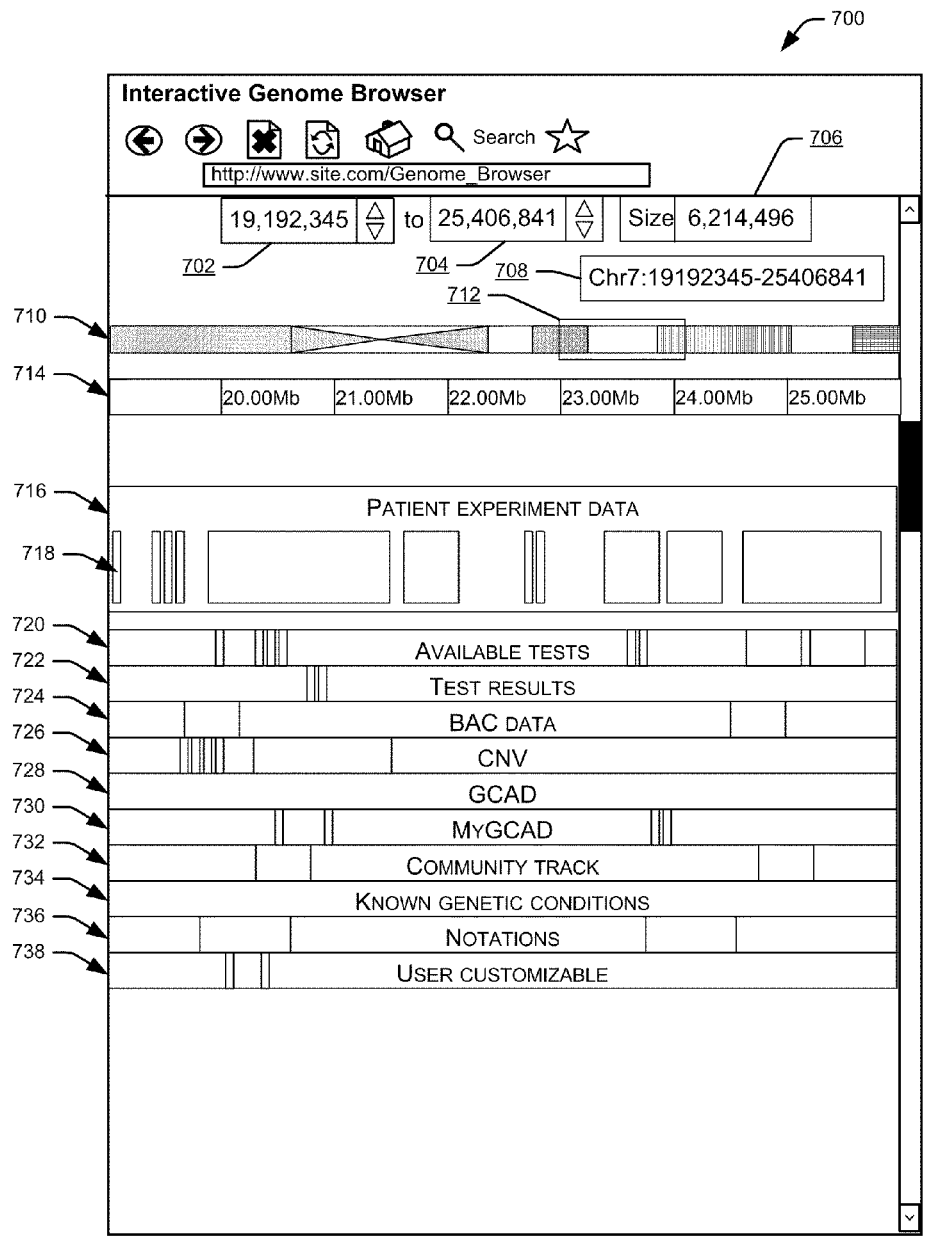
FIG. 7 illustrates a schematic of an interactive genome browser showing navigation elements and available genetic data tracks which are aligned to patient experiment data.

FIG. 7 illustrates a schematic 700 of an interactive genome browser display after selection of the "browser" button 522 of FIG. 5. Navigation controls comprising a starting base pair 702 and an ending base pair 704 for a displayed area of a patient's experimental data may be presented. The size 706 of the displayed area may be presented, showing the distance between the starting base pair 702 and the ending base pair 704. A position indicator 708 shows the chromosomal position of the displayed area.

Displayed is a large scale chromosome ideogram 710 to provide orientation for the user. Superimposed on the large scale chromosome ideogram 710 is an indicator box 712 designating a location of the displayed area defined by the starting base pair 702 and the ending base pair 704.

A base pair ruler 714 displays a regular interval of base pairs for ease of navigation. For example, at this scale of view, the intervals are 1 million base pairs (Mb). As the displayed area is narrowed or expanded the intervals are adjusted to match.

Patient experimental data 716 may be displayed, with detailed experimental regions 718 indicated. Aligned with base pairs in the patient experimental data, the following additional tracks may be displayed individually or in any combination: A track displaying available tests 720, such as FISH probes, BAC clones, or other methods to visualize the specific DNA copy number in situ such as Primed in situ Labeling (PRINS) or related techniques. A track displaying test results 722. A BAC data 724 track. A copy number variation (CNV) track 726. A track displaying GCAD data 728. A track displaying MyGCAD data 730. A track displaying community data 732. A track displaying known genetic conditions 734. Furthermore, a track displaying notations 736 made by users, while a user-customizable track 738 may also be shown. Individual tracks may be hidden if desired by the user, displayed in full detail, or shown in a condensed or dense view.

Figure 8:
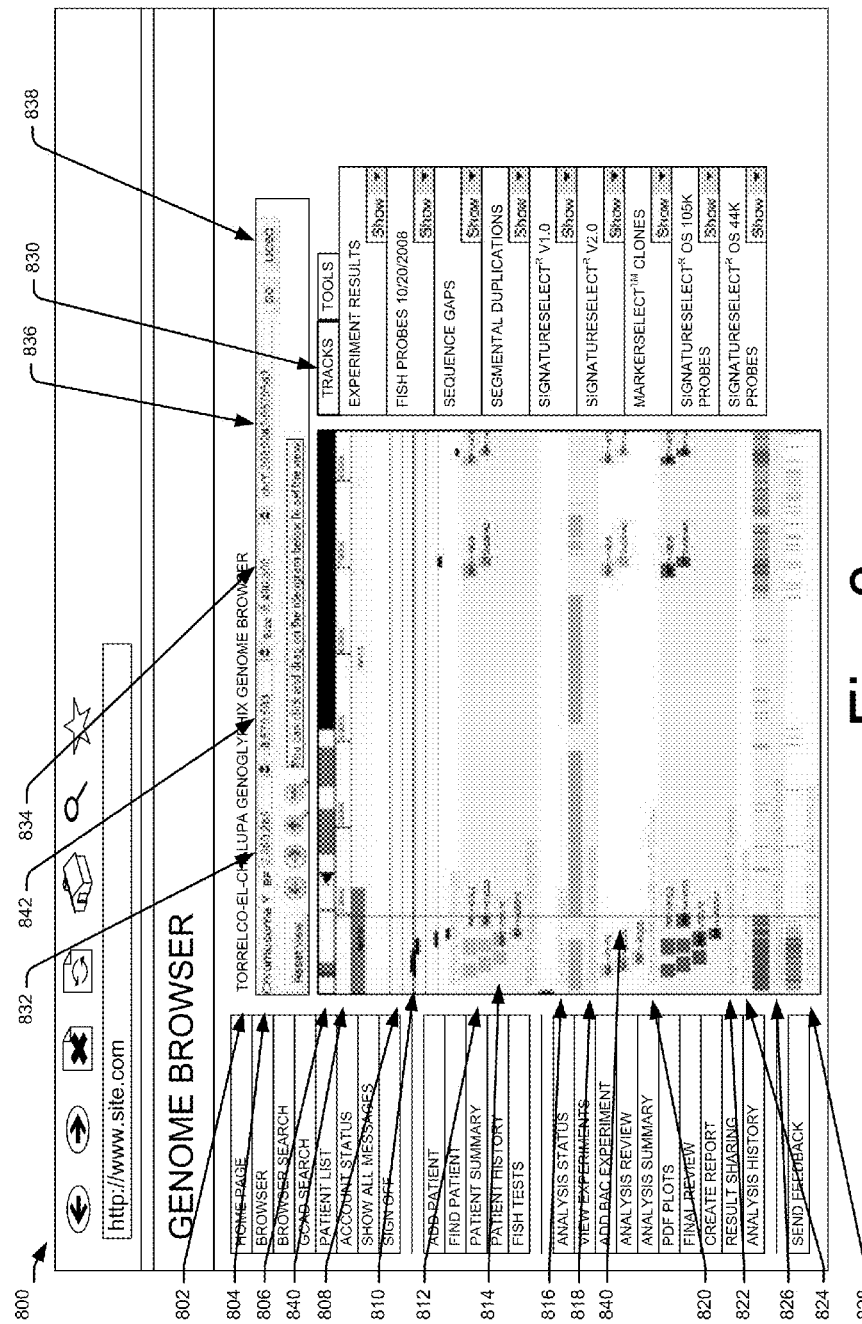
FIG. 8 illustrates another embodiment of an interactive genome browser after selection of the "browser" button shown in FIG. 5.

FIG. 8 is another embodiment 800 of an interactive genome browser display after selection of the "browser" button 522 of FIG. 5. Patient information 802 may be displayed. A navigation cluster 804 may be displayed. Navigation cluster 804 may comprise a starting base pair editable field 832, an ending base pair editable field 842, a size display 834 indicating the distance between the starting base pair and the ending base pair currently displayed, and buttons 838 to update the displayed data and access an external database. Additional functions in the navigation cluster comprise a button to reset the view to an original state, and buttons to scroll and zoom the displayed area. Additionally, a user may zoom in on a region by clicking and dragging a pointing device on a data track or within a large scale chromosome ideogram 806. An indicator box designating a location of the displayed area defined by the starting base pair 832 and the ending base pair 842 is also shown on the chromosome ideogram.

Base pair ruler 840 displays a regular interval of base pairs for ease of navigation. For example, at this scale of view, the intervals are 1 million base pairs (Mb). As the displayed area is narrowed or expanded the intervals are adjusted to match.

A patient experiment results track 808 is shown with detailed experimental regions 810 indicated. Additional data tracks, aligned with the base pairs of the track 808 may also be displayed.

A track showing available genetic tests, such as FISH probes, may be displayed. Each available fish probe 814 is indicated. As described below, selection of an available probe will present a test order entry interface.

The following tracks may also be displayed: Sequence gaps 816, segmental duplications 818, available clones 822 and 824, and probes 828 are shown.

The user cursor 840 may be indicated as a vertical bar extending throughout all displayed tracks. This cursor may be configured to snap to the edges of a region within a track, to facilitate fine placement of the cursor to a particular location of interest on the displayed data track.

A tracks menu 830 displays available tracks and the type of view desired. For example, tracks may be shown, hidden, or displayed in a dense or compact format.

Figure 9:
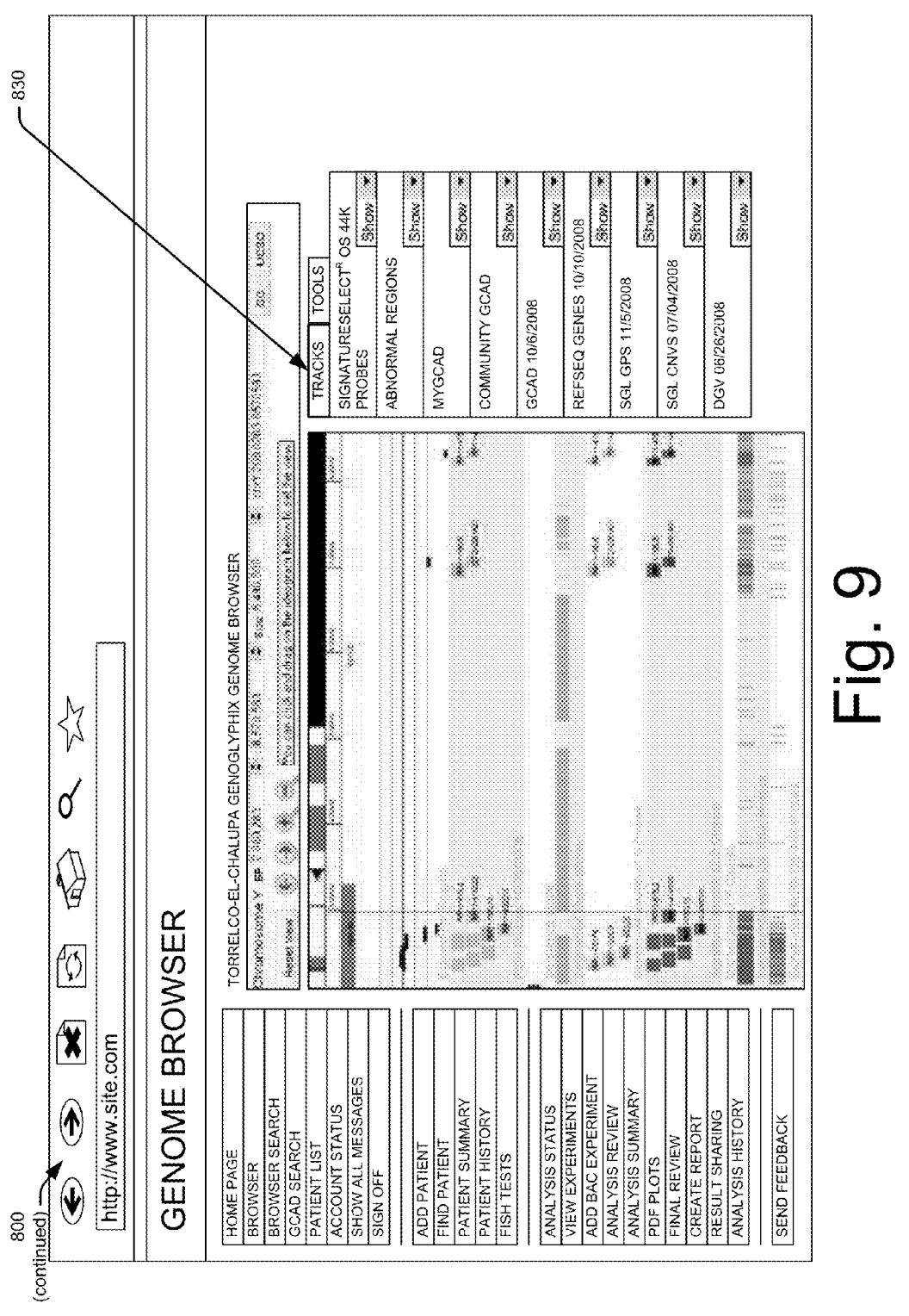

FIG. 9 illustrates additional genetic data tracks ("tracks") available for display in the interactive genome browser 800 of FIG. 8. Tracks menu 830 shows a list of tracks which may be displayed, and possible display settings.

Figure 10:
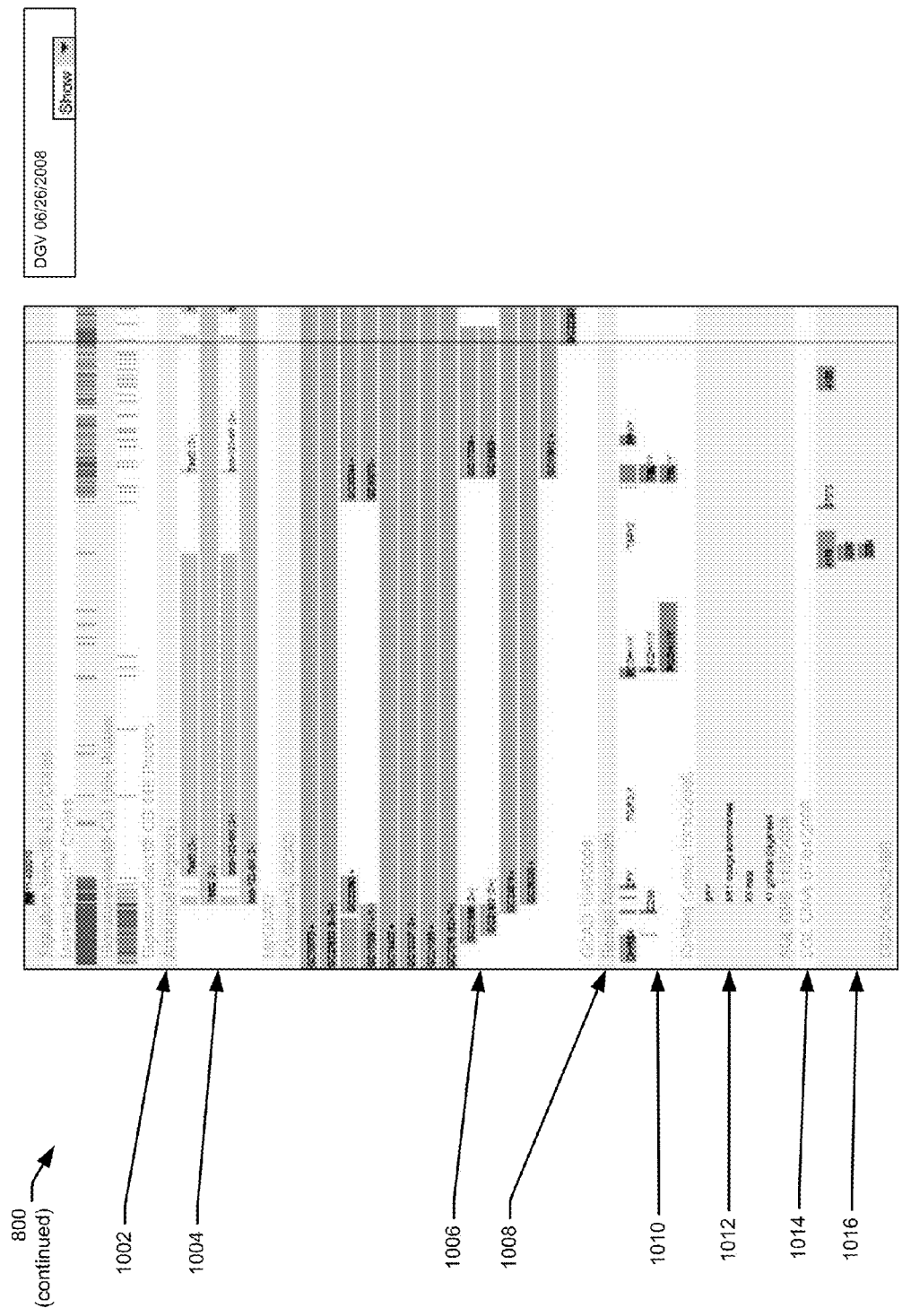
FIG. 10 illustrates additional tracks displayed in the interactive genome browser of FIG. 8.

FIG. 10 illustrates additional tracks displayed in the interactive genome browser 800 of FIG. 8. A track showing abnormal regions 1002 are displayed. A track displaying data from other patients accessible to a specified user ("MyGCAD") 1004 may be displayed. MyGCAD data may comprise chromosomal aberrations that a specific user may have elected to denote as such in his/her collection of patients. This database is viewed only by that particular user (hence "MyGCAD"). In some instances, the "MyGCAD" track consists of data uploaded by the specified users. As such, in some instances, this track displays data about patients of the specified user, but does not display data about patients of other users of the system. Next, a track displaying information gathered from testing done by a specific lab ("GCAD") 1006 is shown. In some instances, this specific lab comprises service provider 108 of FIG. 1. Other tracks which may be displayed are benign abnormals 1008, RefSeq genes 1010, lab specific positioning data such as SGL GPS 1012, lab specific CNV's such as SGL CNVs 1014, and DGV 1016. RefSeq 1010, or Reference Sequence (RefSeq) Genes data is a non-redundant collection of richly annotated DNA, RNA, and protein sequences from diverse taxa. SGL GPS 1012 is a Signature Genomic Laboratories Genome Positioning System, a track which displays known genetic syndromes that occur when the corresponding segment of genomic DNA undergoes copy loss or gain. SGL CNVs 1014 is a database of benign copy number variants, for example the database developed by Signature Genomic Laboratories, based on our experience from our patients that these are indeed benign copy number variants of no clinical significance. DGV 1016 is a Database of Genomic Variants, a publically available database in Toronto, Canada that displays known Copy Number variants (CNVs) deposited there by researchers from all over the world.

Figure 11:
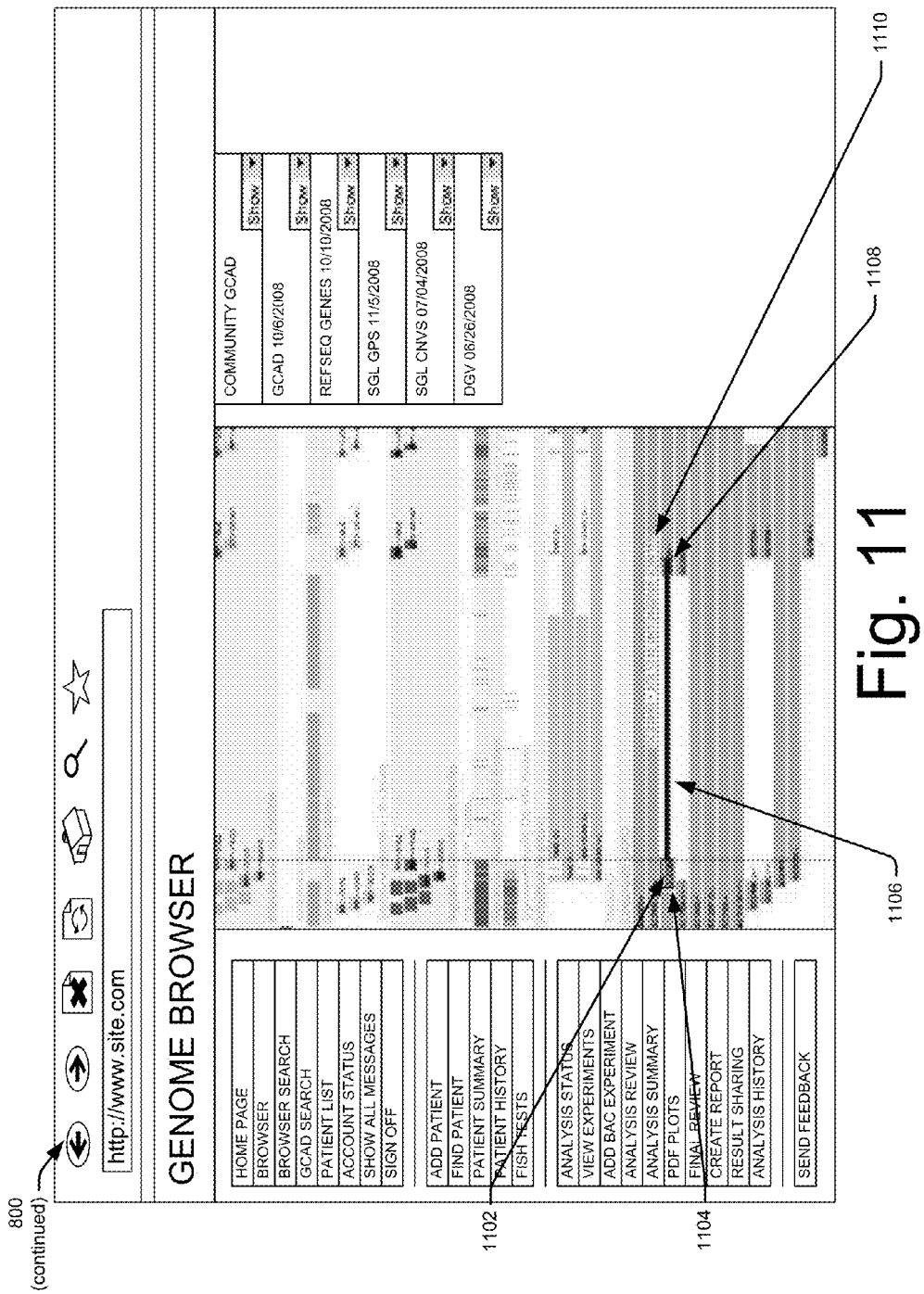
FIG. 11 illustrates additional tracks displayed in the interactive genome browser of FIG. 8, and gap indicator bars upon selection, the gap comprising the distance in coverage of the genome in the array, indicating the maximum possible aberration.

FIG. 11 illustrates additional tracks displayed in the illustrative interactive genome browser 800 of FIG. 8 and gap indicator bars. A region of interest 1102 on the GCAD track is selected, with the selection shown by a highlight 1104. A gap indicator 1106 extends from the region of interest to an end bar 1108. This gap indicator displays the distance to a next oligonucleotide probe or bacterial artificial chromosome (BAC) clone which is not part of the region of interest. A gap indicator 1106 may extend from either the left or right side of a region of interest, as defined by the gap to the next oligo probe or BAC clone. The gap indicator therefore indicates the maximum possible aberration for that individual. When a region of interest 1102 is selected in any track, a selection information box 1110 may be displayed, which may display the name of the region, its length, and location in the genome.

Figure 12:
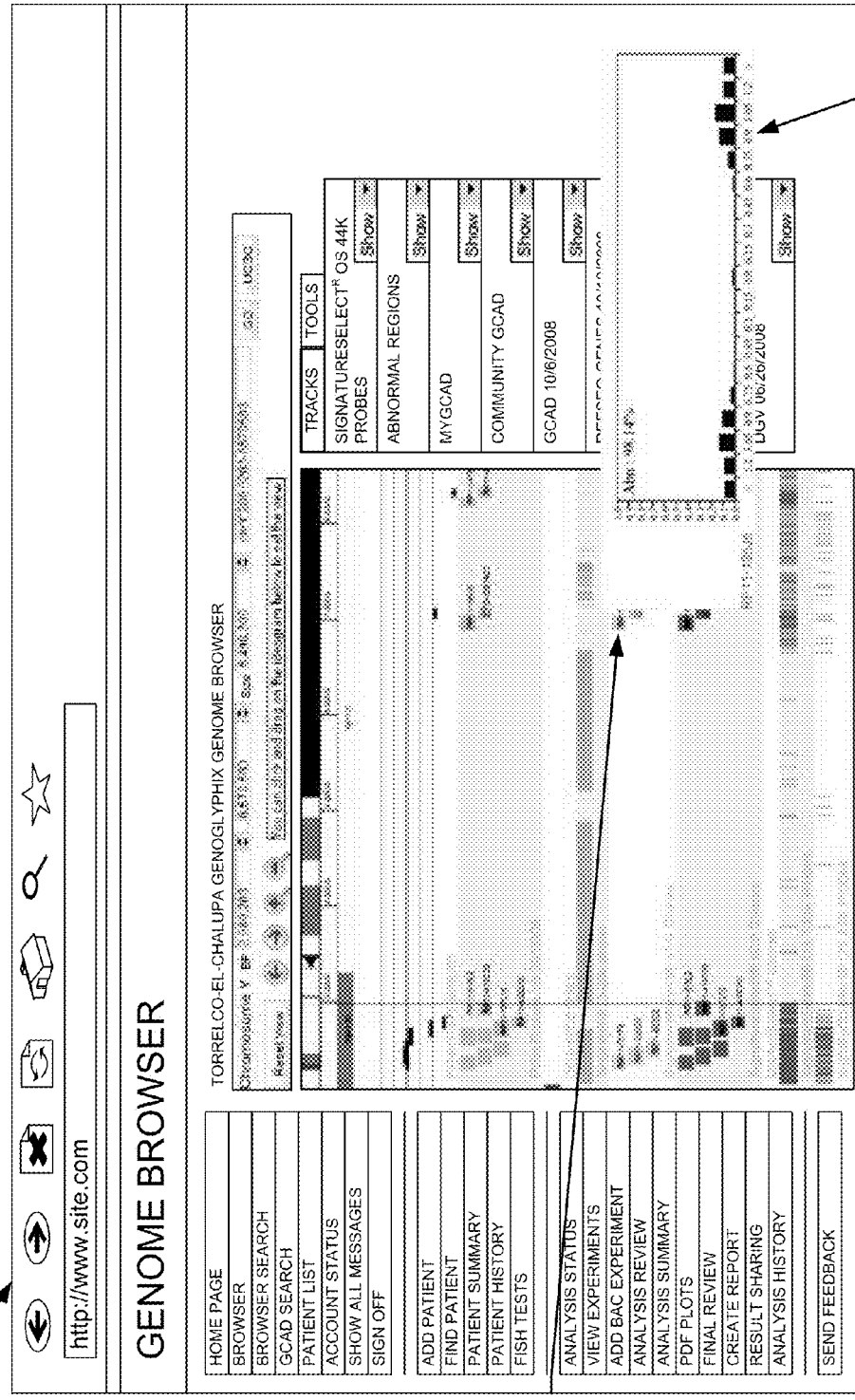
FIG. 12 illustrates a selection of a region of interest in the interactive genome browser of FIG. 8 and presentation of supplemental data.

FIG. 12 illustrates a selection of a region of interest 1202 in the interactive genome browser 800 of FIG. 8 and presentation of supplemental data. As described above with respect to FIG. 11, upon selection of a region of interest 1202, a selection information box 1204 is shown displaying detailed results for that region.

Figure 13:
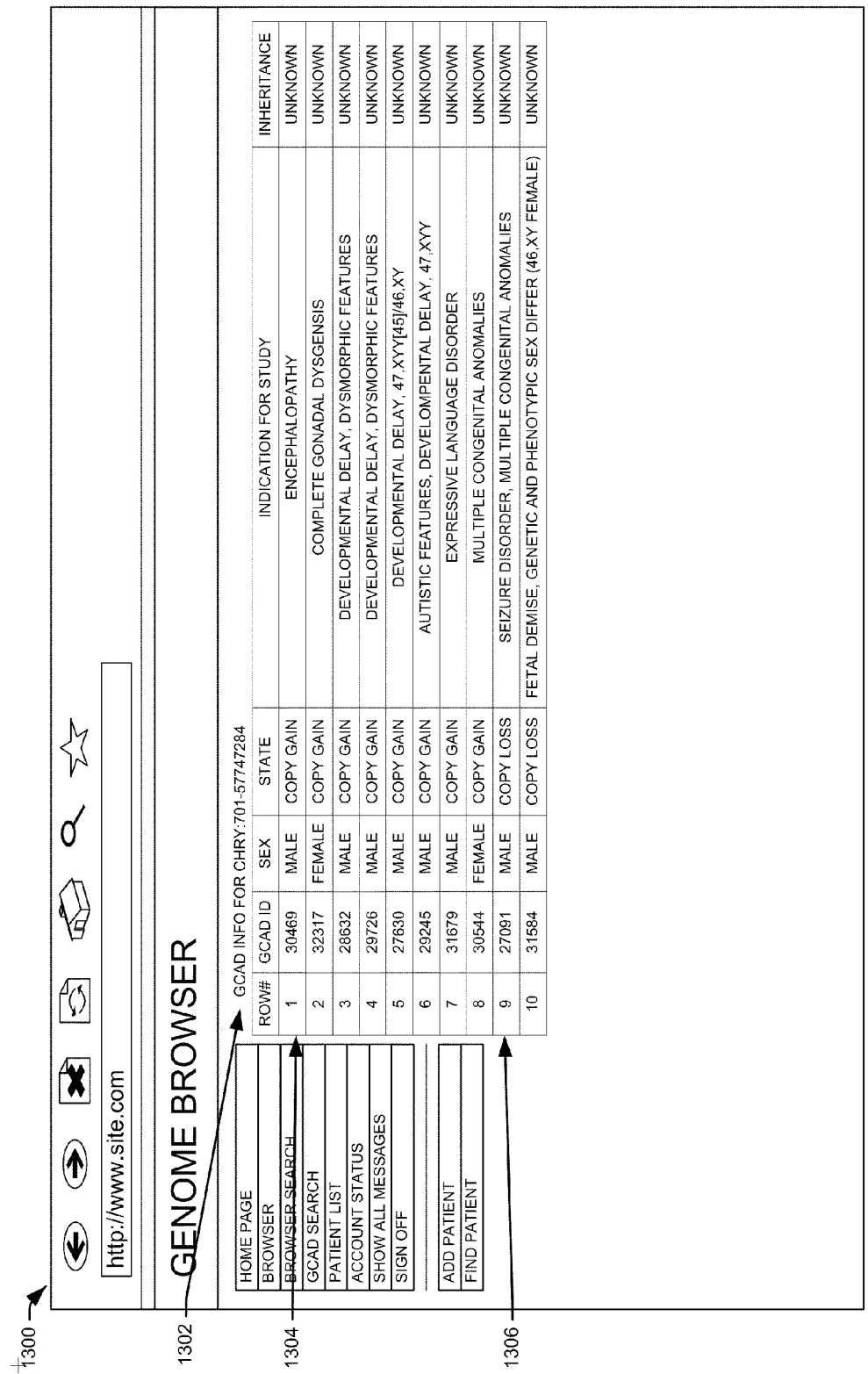
FIG. 13 illustrates a summary listing of abnormalities, for example those present in a Genoglyphix Chromosome Aberration Database ("GCAD"), with results shown in the interactive genome browser 800 of FIG. 10.

FIG. 13 illustrates a summary listing 1300 of results from a database of abnormalities such as the Genoglyphix Chromosome Aberration Database ("GCAD") 1006 shown in the interactive genome browser 800 of FIG. 10. Upon selecting a region present in the GCAD results 1006, a summary listing 1300 may be displayed. A GCAD information display 1302 indicates the genomic location for this listing. GCAD summary information list may be displayed 1304. This GCAD summary information comprises a GCAD identifier ("GCAD ID"), patient sex, state of an abnormality, indications for study, and inheritance. For example, a specific patient 1306 may have GCAD ID of 27091, be a male with a copy loss, and have indications comprising a seizure disorder and multiple congenital anomalies.

Figure 14:
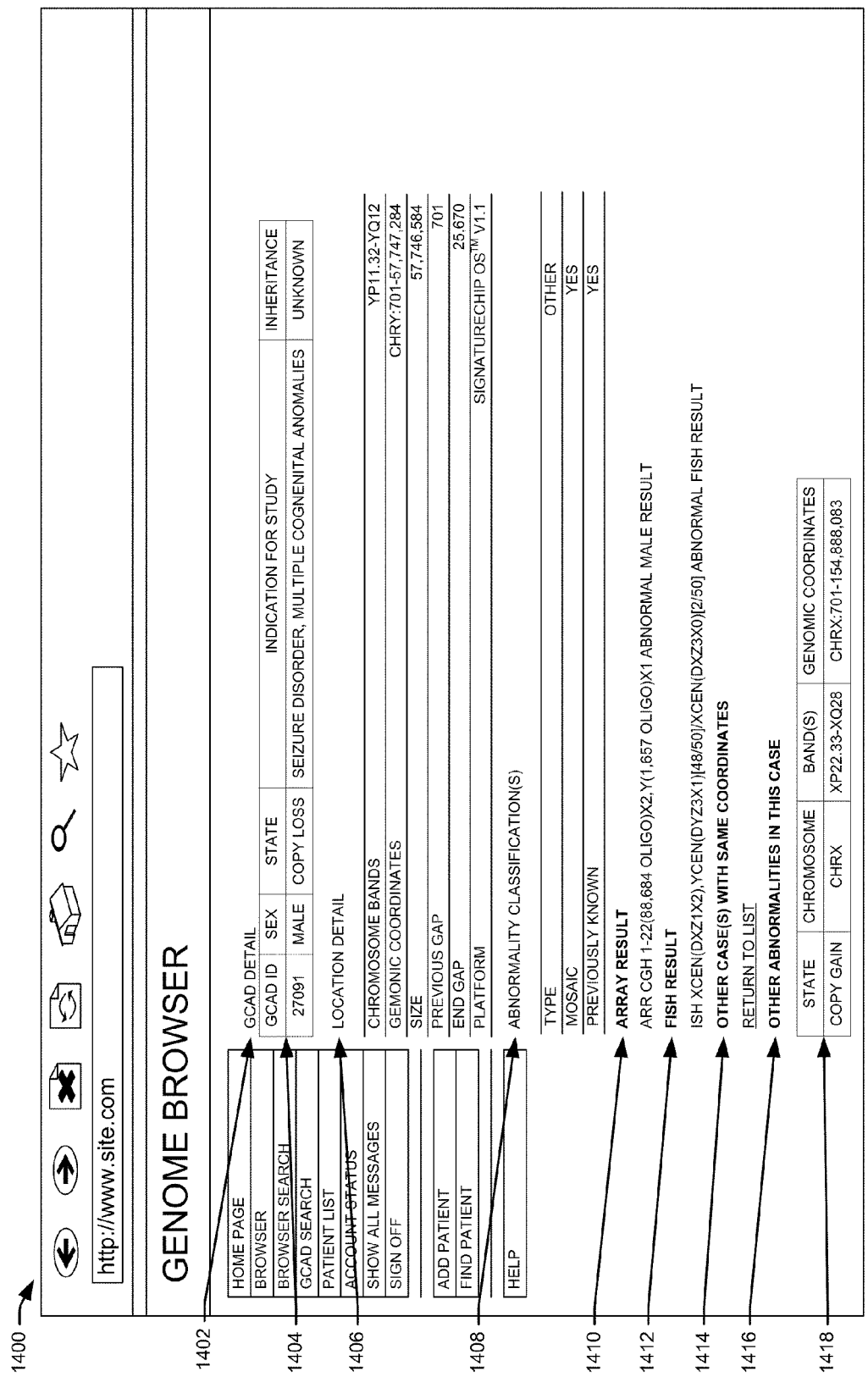
FIG. 14 illustrates additional detail in the interactive genome browser 800 available upon selection of a GCAD line item shown in FIG. 13.

FIG. 14 illustrates additional GCAD detail 1400 available upon selection of specific patient 1306 shown in the GCAD summary information list 1304 of FIG. 13. A page header 1402 indicates this view is of GCAD detail information. Patient information 1404 may be displayed. Location details 1406 may be shown. These location details 1406 may comprise chromosome bands, genomic coordinates, size, previous gap, end gap, and platform for the testing.

Abnormality classifications 1408 may also be displayed. Abnormality classifications 1408 may comprise type, mosaic, or whether the abnormality is previously known.

Array results 1410 may be displayed. FISH results 1412 may also be displayed. A link to other cases with the same coordinates 1414 may be presented. Other abnormalities in this case 1416 may also be displayed, with summarized data 1418 presented. Access to underlying detailed data may then be obtained by selecting the summarized data.

Figure 15:
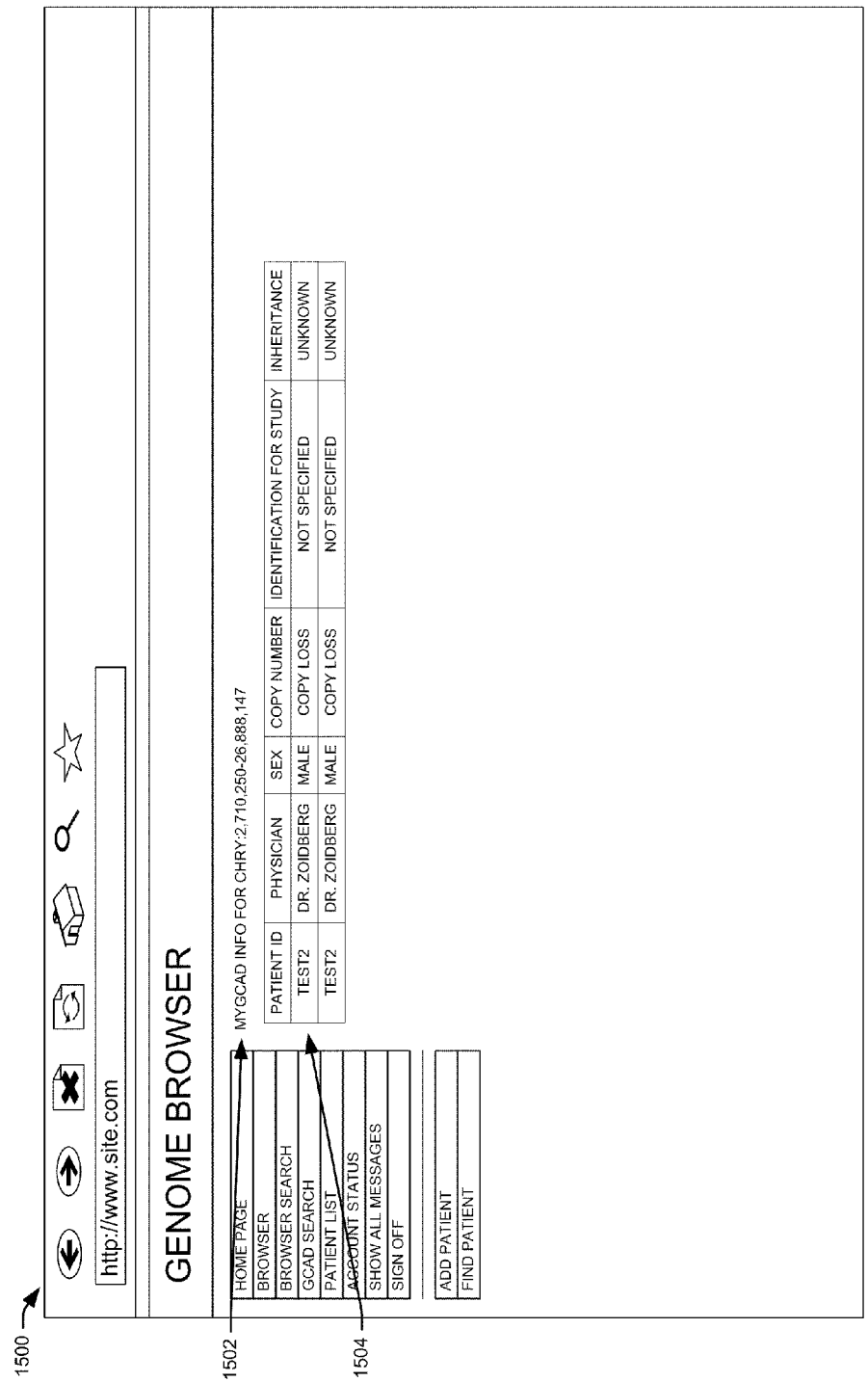
FIG. 15 illustrates a summary listing of chromosomal aberrations present within a user's personal collection of patients, termed "MyGCAD" displayed in the interactive genome browser 800 in FIG. 10.

FIG. 15 illustrates a summary listing 1500 of MyGCAD patient data displayed by the interactive genome browser 800 of FIG. 10. MyGCAD patient data comprises patients analyzed by a particular user, or group of users, for example users which are staff at the same hospital or laboratory. A header indicates the data source, in this case "MyGCAD" and the genomic location being displayed. A summary patient listing 1502 may be presented. The information presented in the summary patient listing 1502 may comprise the patient identification, physician, sex, copy number, indication for study, and inheritance. For example, a particular patient named "test2" 1504 may be displayed.

Figure 16:
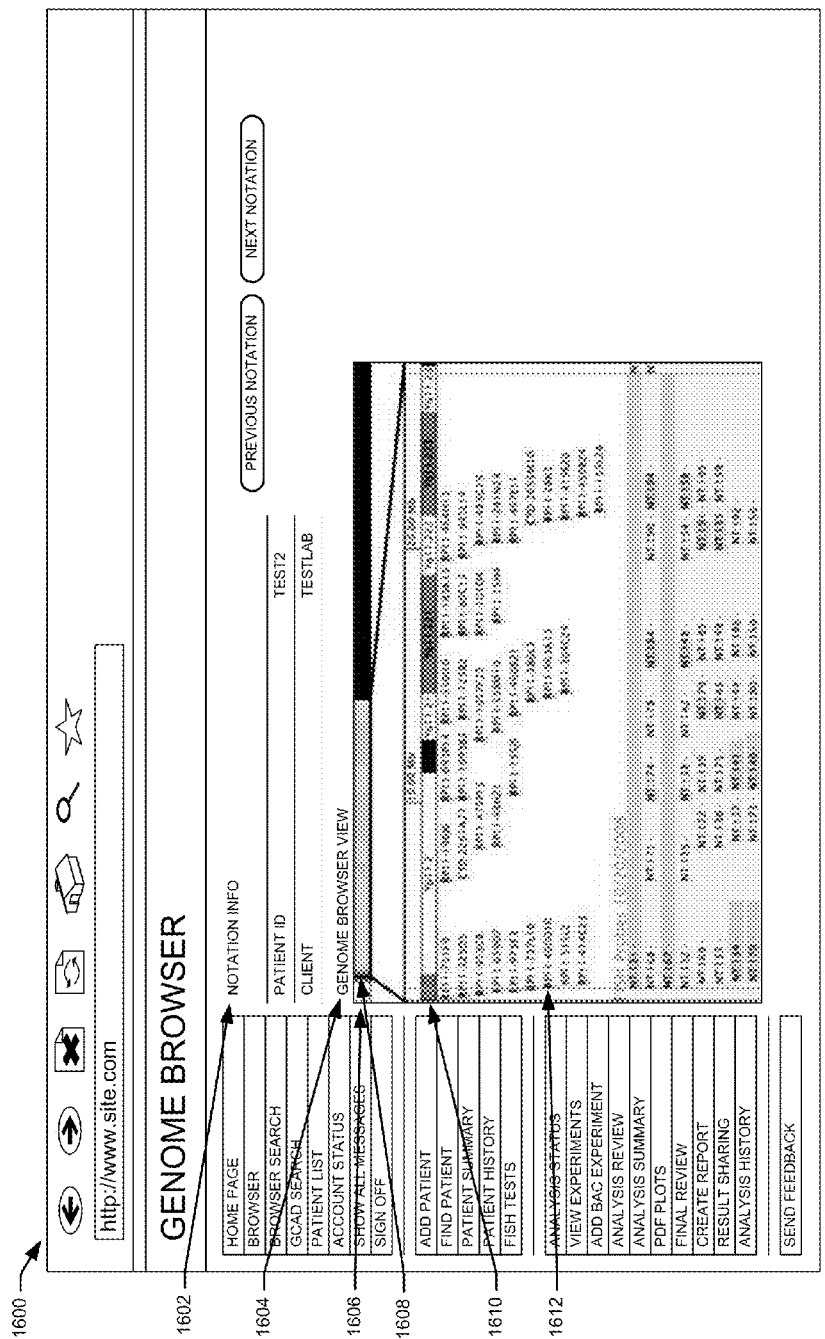
FIG. 16 illustrates a detailed view of a patient listed in the summary listing of FIG. 15.

FIG. 16 illustrates a detailed view 1600 of patient 1502 as listed in the summary listing 1504 of FIG. 15. Notation information 1602 may be presented to indicate the patient and client for this data. A detailed interactive genome browser view 1604 may be presented. This interactive genome browser view 1604 comprises elements of the interactive genome browser 800. For example, a large scale chromosome ideogram 1606 with a box 1608 indicating the displayed area. A base pair ruler 1610 is visible, here with 10 Mb intervals. Also illustrated are available FISH probes 1612.

Figure 17:
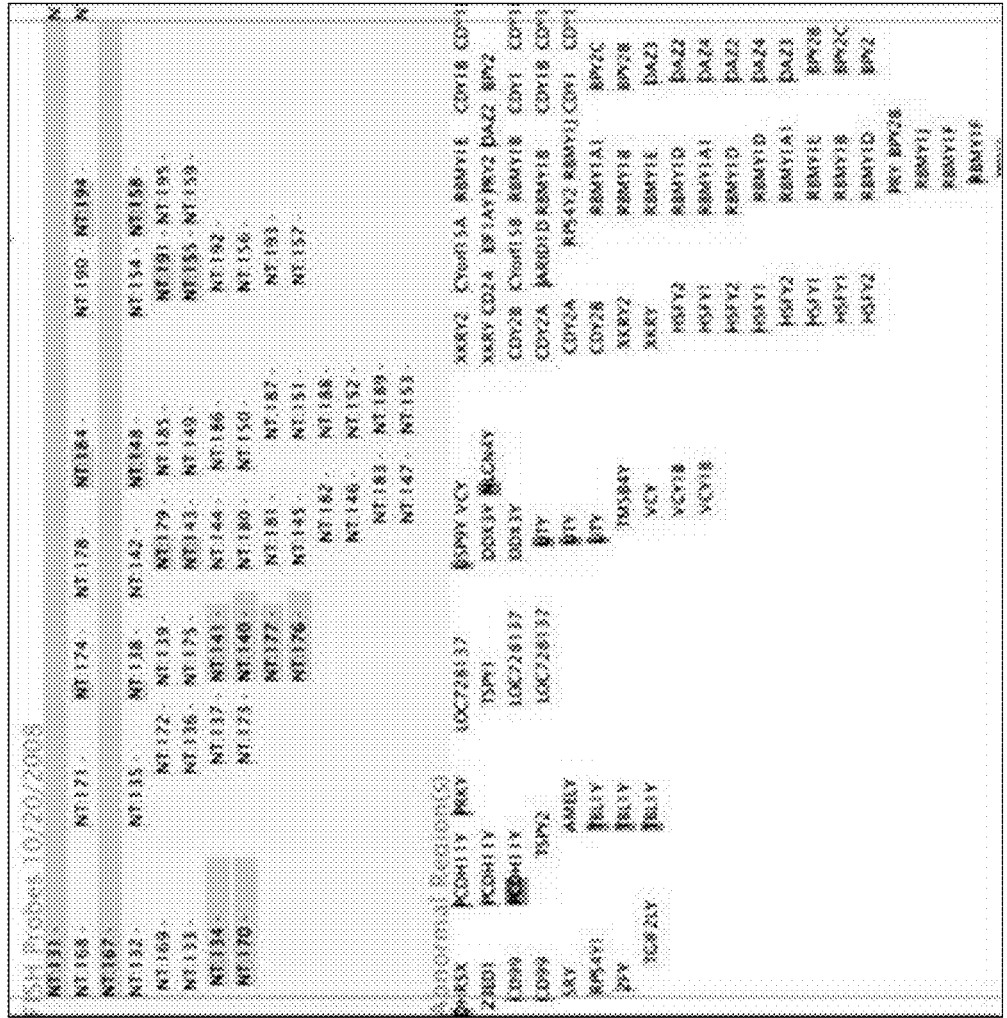
FIGS. 17-18 illustrate additional tracks available in the detailed view of FIG. 16.

FIG. 17 illustrates additional tracks available in the detailed view 1600 of FIG. 16, showing the abnormal regions track 1702.

Figure 18:
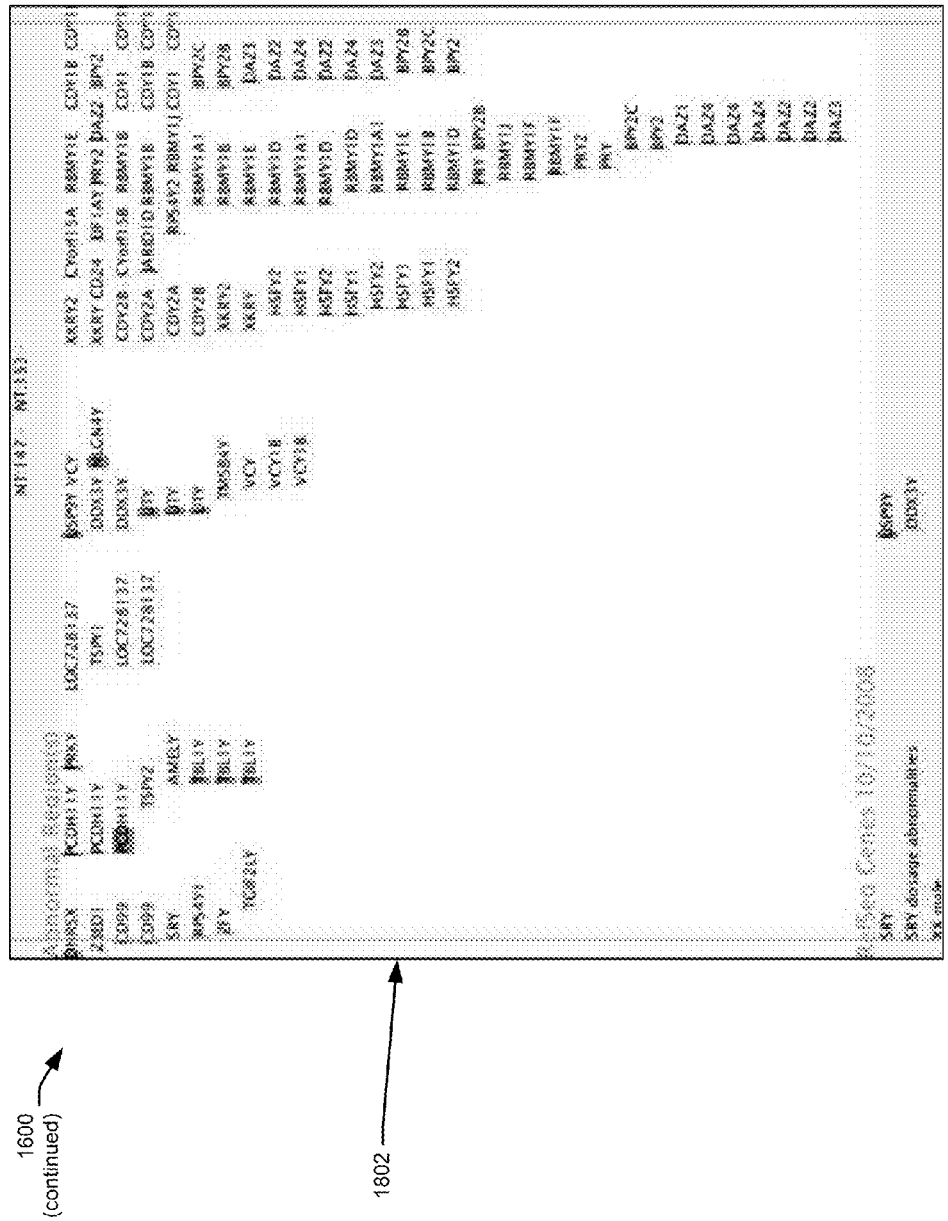

FIG. 18 illustrates additional tracks available in the detailed view 1600 of FIG. 16, showing the RefSeq Genes track 1802. The Reference Sequence (RefSeq) Genes data is a non-redundant collection of richly annotated DNA, RNA, and protein sequences from diverse taxa.

Figure 19:
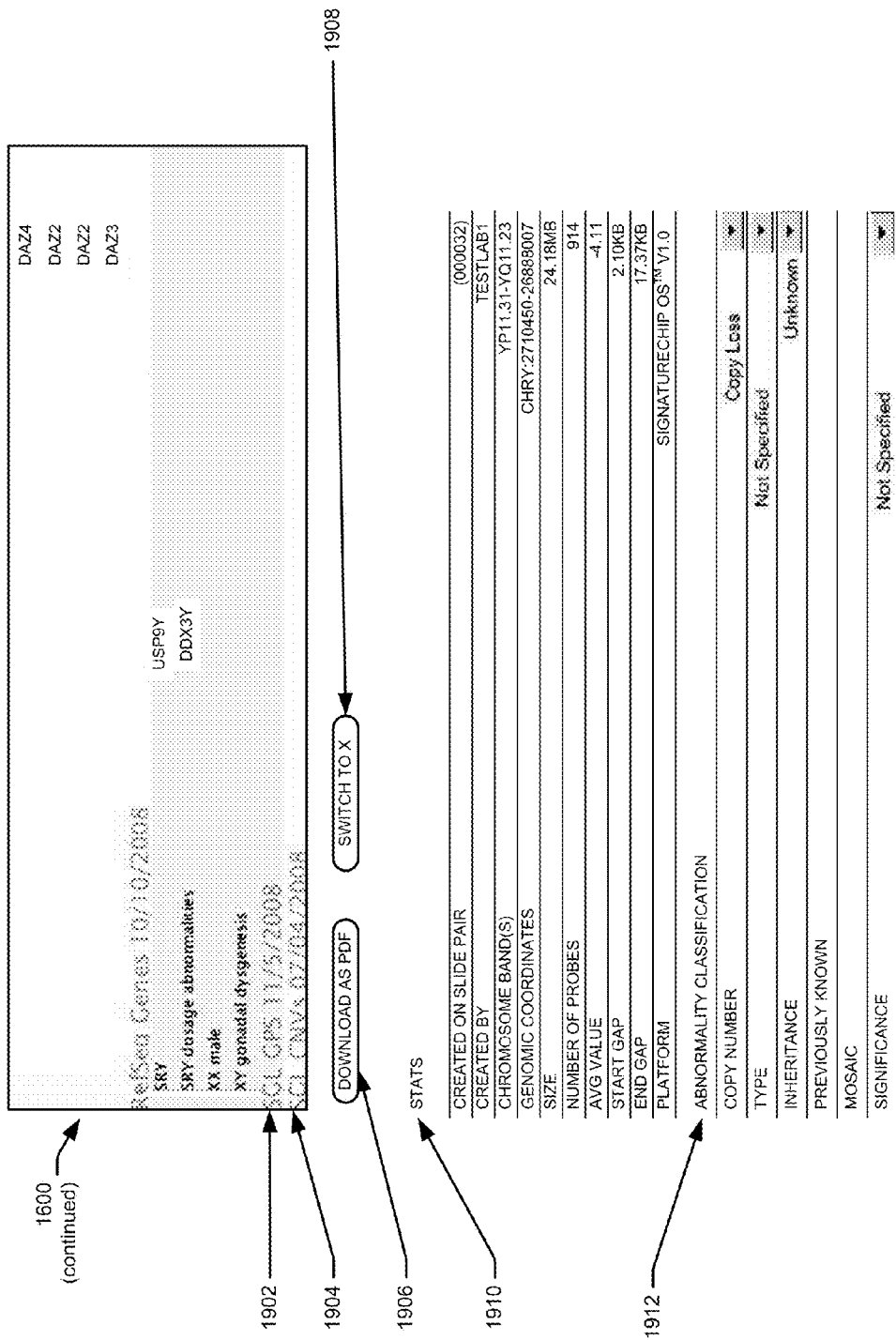
FIG. 19 illustrates additional details available in the detailed view of FIG. 16, including additional tracks, statistics, and abnormality classification information.

FIG. 19 illustrates additional details available in the detailed view 1600 of FIG. 16. The SGL GPS track 1902 and SGL CNV 1904 tracks are displayed. A user may select to download the detailed report as a PDF 1906, or switch display to the X chromosome 1908. The switch display to the X chromosome 1908 function may be used to move the abnormality from the Y chromosome displayed to the X chromosome. Similarly, when displaying the X chromosome, a switch to the Y chromosome may be displayed. When an array result for an abnormality in the pseudoautosomal region is presented, it is not known until later in the analysis which chromosome the abnormality is actually on. This function provides a convenient way to switch the notation and adjust coordinates for the abnormality to the chromosome which has been determined to be correct.

Statistics 1910 may also be displayed. These statistics 1910 may comprise the slide pair created on, who created the statistics, chromosome band(s), genomic coordinates, size, number of probes, average value, start gap, end gap, and platform of the test. Abnormality classification 1912 may also be entered. Abnormality classification 1912 may comprise copy number, type, inheritance, whether previously known, mosaic, and significance.

FIG. 20 illustrates additional details available in the detailed view 1600 of FIG. 16. An area for a user to enter notes 2002 may be displayed, along with an update button 2004 to incorporate changes. A list of genes in the region 2006 may be displayed. The list of genes in the region 2006 may comprise a gene identifier 2008, and a link to external databases such as the genetic database at University of California at Santa Cruz (UCSC) 2010 and/or the Online Mendelian Inheritance in Man (OMIM) genetic database 2012.

FIG. 21 illustrates additional details available in the detailed view 1600 of FIG. 16. A listing 2102 of fluorescent in-situ hybridization ("FISH") probes available for testing in the region is displayed.

Illustrative Ordering of Additional Genetic Tests

Figure 22:
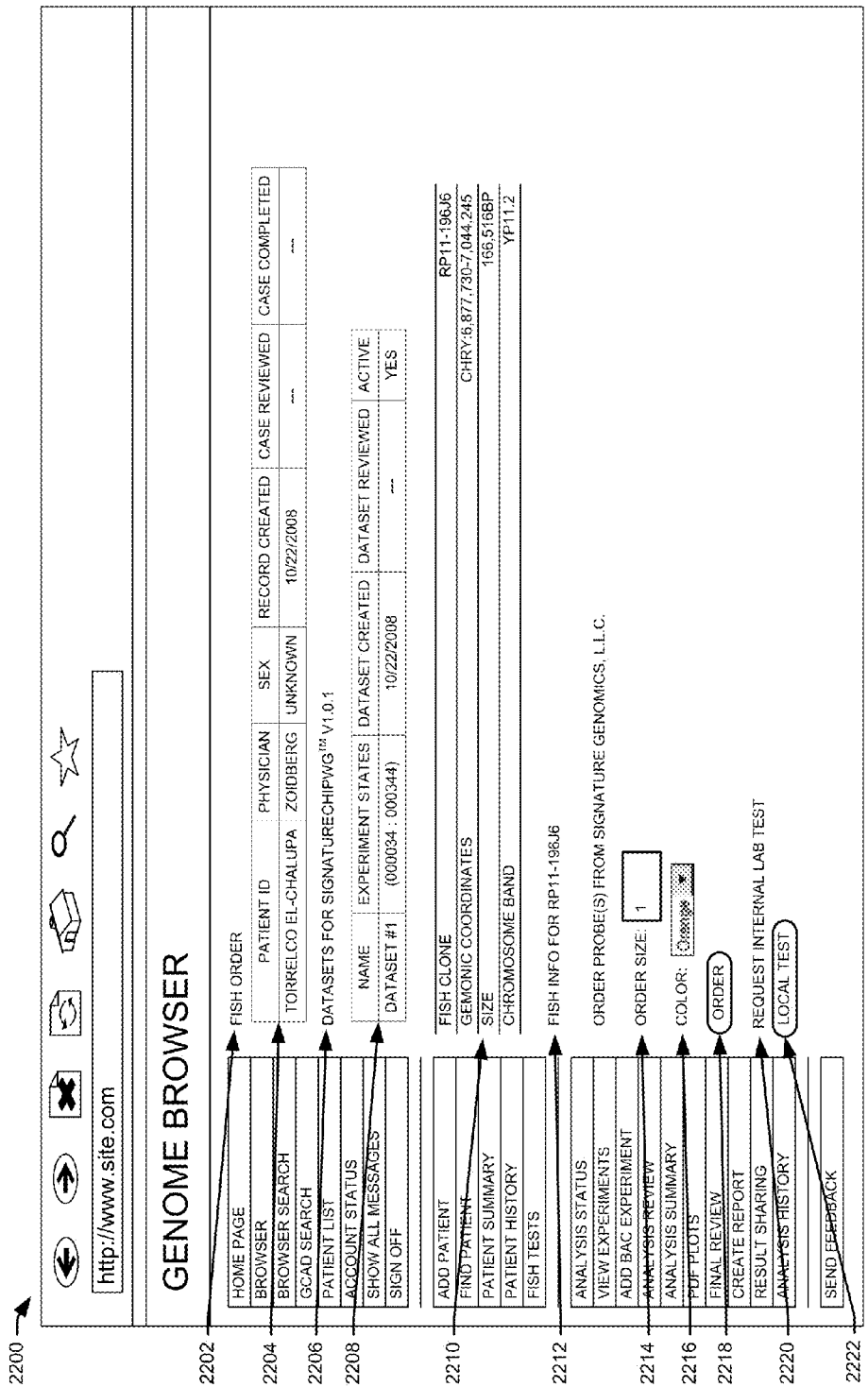
FIG. 22 illustrates an order form for additional genetic tests such as a FISH, after a user has selected a test from a test track.

FIG. 22 illustrates 2200 an order form for additional genetic tests, the genetic test being selected within the interactive genome browser upon selection of the test or probe in a test track. Additional genetic tests may comprise FISH, BAC clones, or any other type of genetic test. For example, as described above with respect to FIG. 8, a track showing available genetic tests, such as FISH probes, may be displayed. Each available FISH probe is indicated.

In this example, a header 2202 indicates that this is a FISH order page. Patient information 2204 may be displayed. The dataset platform may be displayed 2206. Details about the dataset 2208 are shown, which may comprise a dataset name, experiment slide numbers, date created, date reviewed, and whether active or inactive. Additional details 2210 may also be shown, comprising FISH clone, genomic coordinates, size, and chromosome band.

Information about the region specified for the FISH is displayed 2212. An order size or quantity 2214 may be indicated, as well as a color 2216 of the probe. An order button 2218 initiates a probe order. A user may also choose to request an internal lab test 2220 by selecting a "local test" button 2222. Other types of tests, when available, may also be ordered in this fashion.

Figure 23:
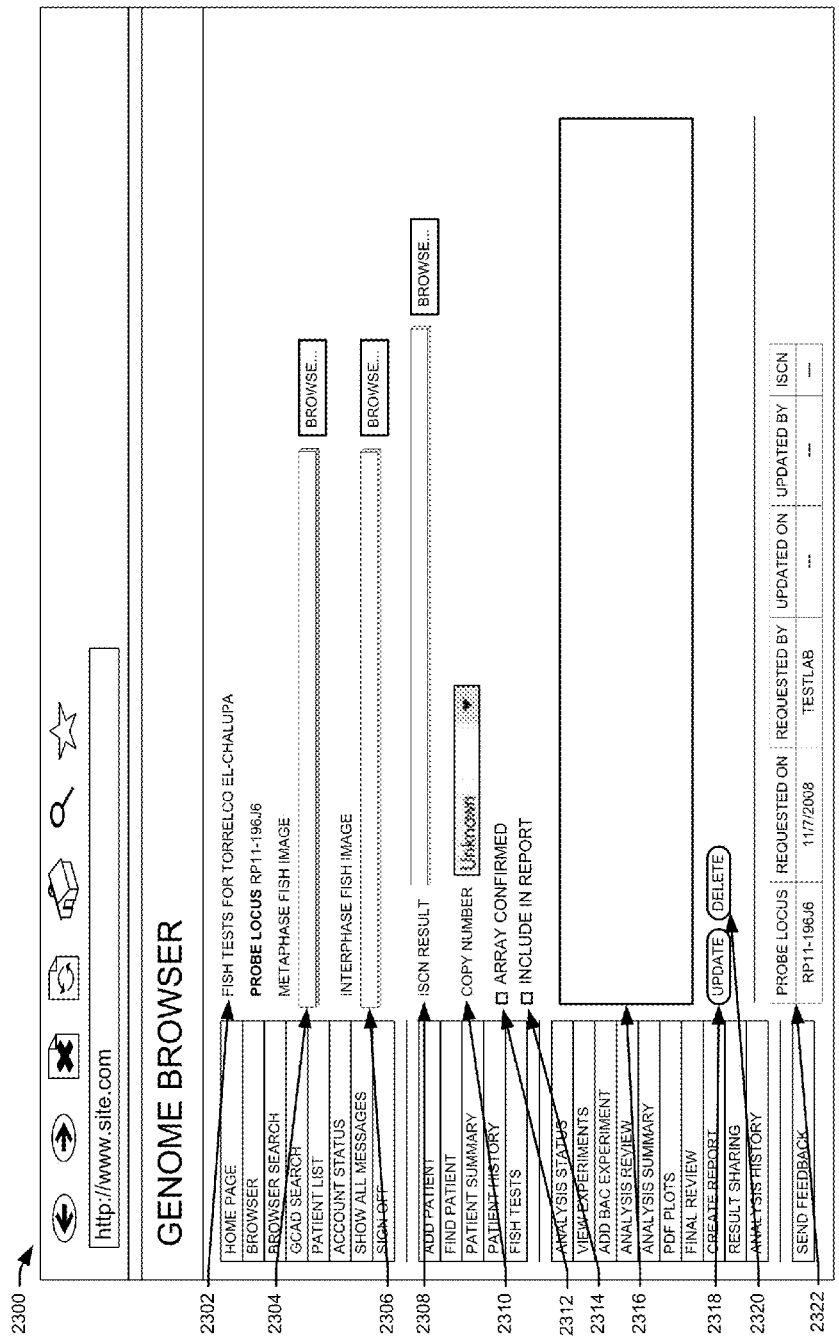
FIG. 23 illustrates the uploading of a user-provided FISH test into the patient database.

FIG. 23 illustrates uploading a user's own test data, such as a FISH test, into the patient database 2300. A name of the test and the patient are displayed 2302. A user may input or browse 2304 to a path containing the file for upload of a metaphase FISH image. A user may input or browse 2306 to a path containing the file for upload of an interphase FISH image. An ISCN result may be input 2308. A copy number 2310 may be entered. The array may be confirmed 2312. A user may indicate if the FISH test being uploaded is to be included in a report 2314.

A user may also add comments or other annotations 2316, and update 2318 or delete 2320 those comments or annotations. Probe details 2322 may also be displayed, the probe details comprising probe locus, date requested, who requested, date updated, who updated, and ISCN. While FISH results are discussed, results from other types of tests may also be uploaded.

Figure 24:
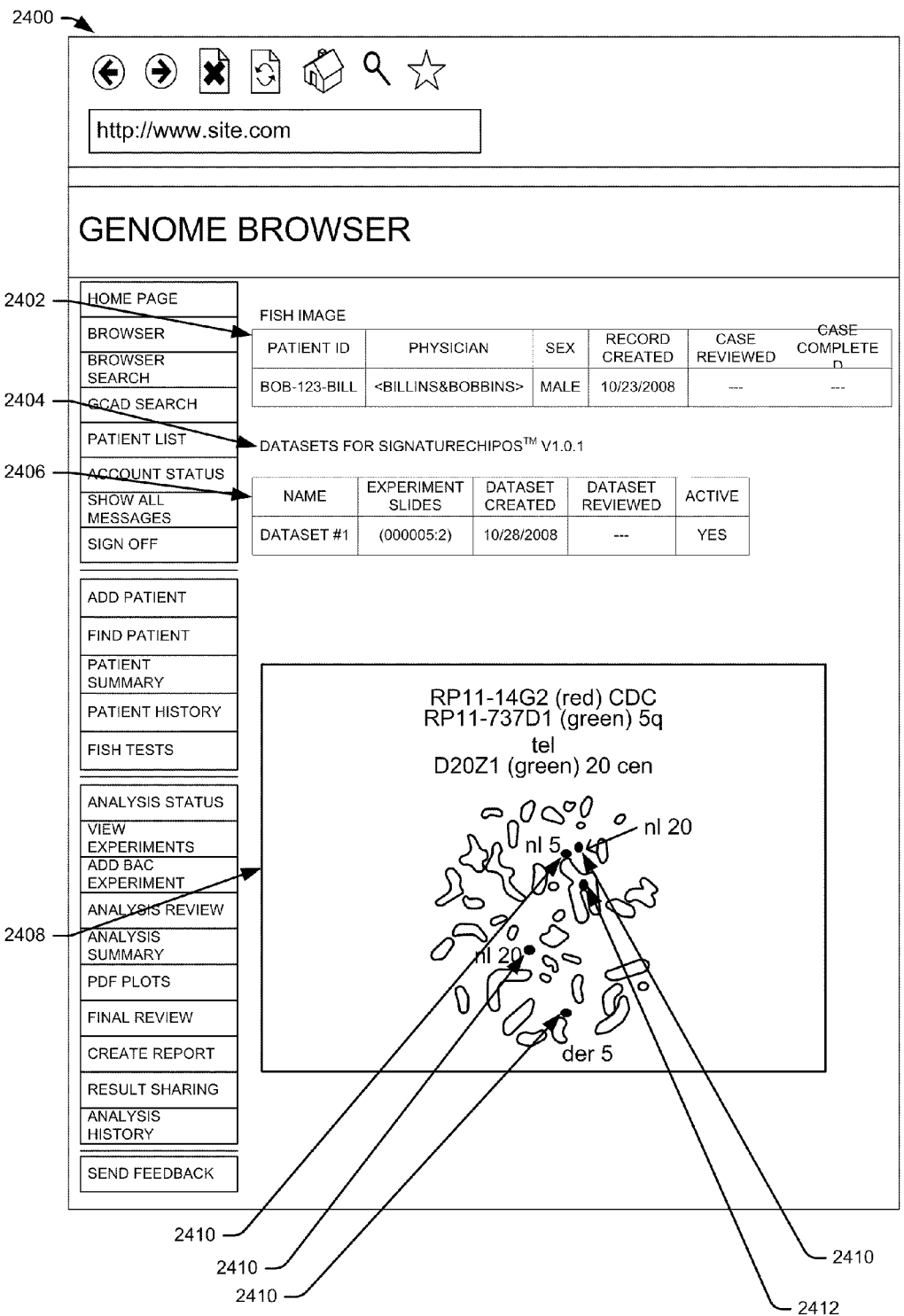
FIG. 24 illustrates a detailed view of a FISH image for a patient.

FIG. 24 illustrates a detailed view 2400 of a FISH image for a patient. Patient information may be displayed 2402, along with the platform 2404 and experiment data 2406. The image of the FISH test 2408 is also present. A green marker 2410 and a red marker 2412 is shown. This detailed view 2400 may be accessed from the interactive genome browser when FISH probe results are present for a patient being displayed in the browser, or by browsing directly to FISH test results within the interactive genome browser.

Establishing Relationships Between Patients in the Database

Figure 25:
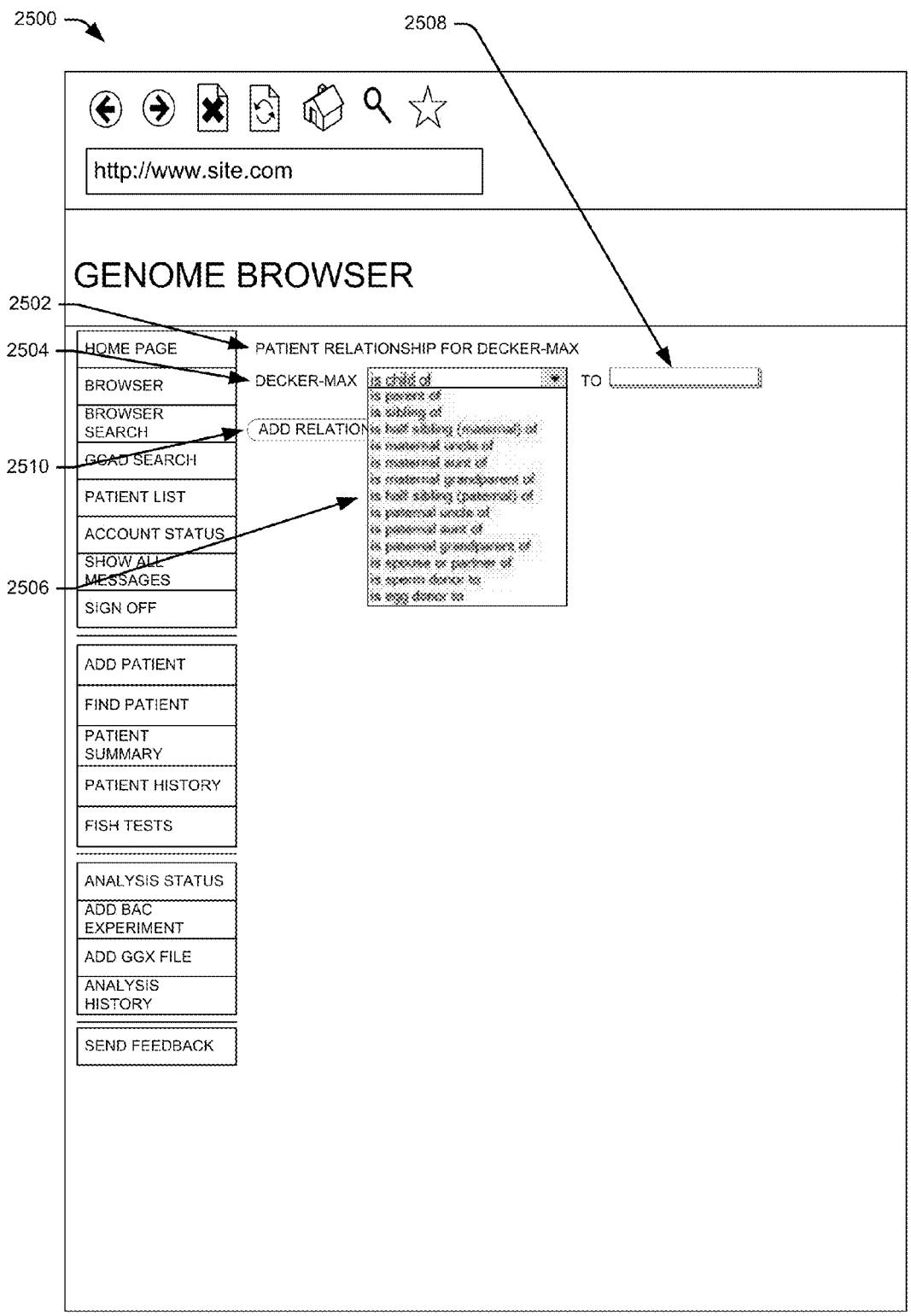
FIG. 25 illustrates the assigning of a relationship between patients.

FIG. 25 illustrates assigning a relationship between patients 2500. Providing relationships between patients facilitates analysis by a user. Genetic abnormalities may be compared against relatives, helping to determine whether an abnormality is benign or clinically significant. The patient being assigned a relationship may be displayed 2502. An input line 2504 permits selection of the type of relationship 2506 and whom 2508 they are related to. Once entered, the relationship may be added by selecting a button 2510. The relationship may comprise being a parent, child, sibling, maternal half sibling, maternal uncle, maternal aunt, maternal grandparent, half sibling (paternal), paternal uncle, paternal aunt, paternal grandparent, spouse or partner, sperm donor, egg donor, or surrogate.

Automated Generation of ISCN

Figure 26:
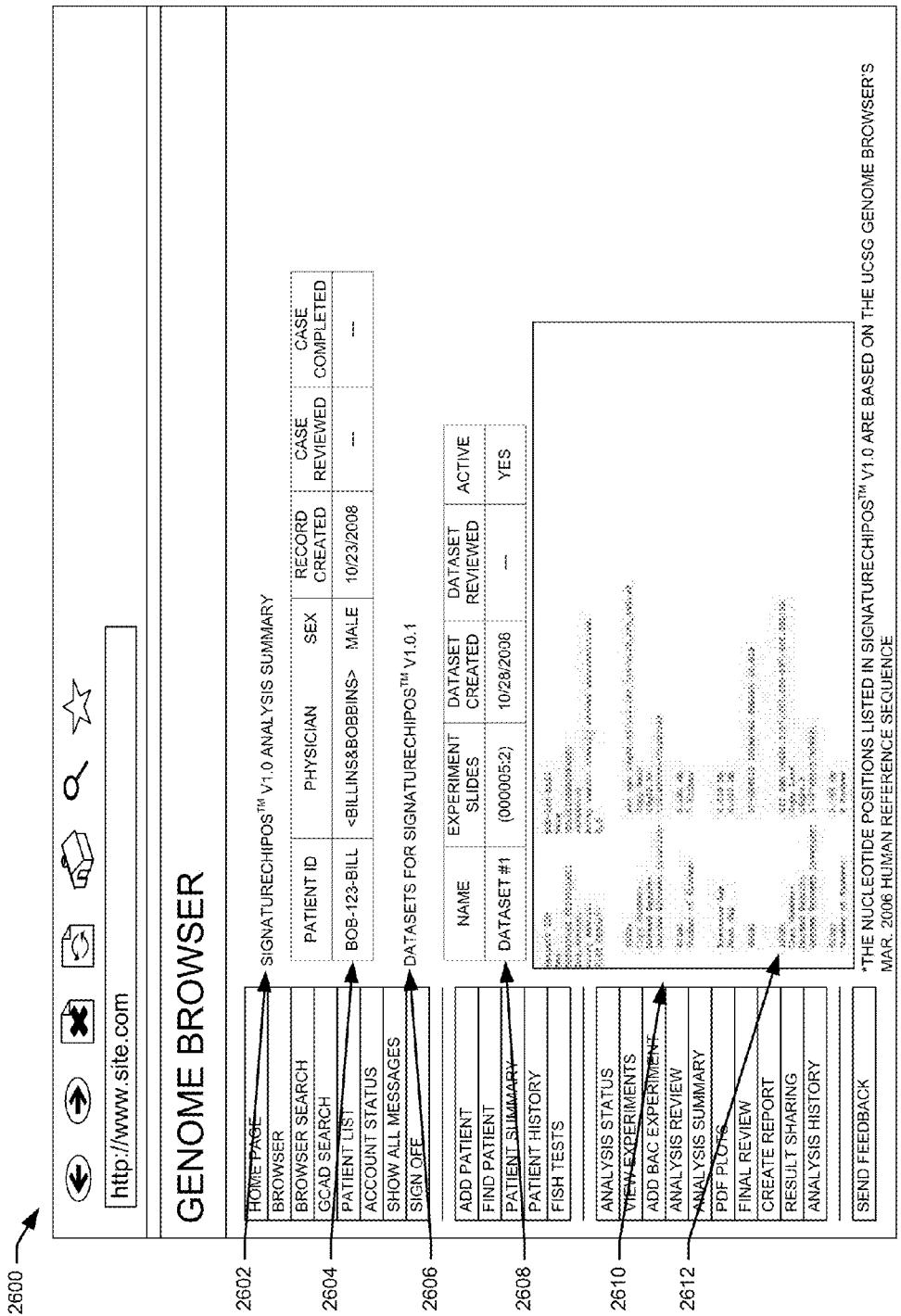
FIG. 26 illustrates a portion of an analysis summary, comprising an automatically-generated International Standard Cytogenetic Nomenclature ("ISCN") for a region of interest.

FIG. 26 illustrates a portion of an analysis summary 2600. A header 2602 indicates that an analysis summary may be displayed. Patient information 2604 may be displayed. The dataset platform 2606 may be displayed. Dataset information may be displayed 2608. The body of the report 2610 may describe all abnormalities found during analysis. For each abnormality found, an International Standard Cytogenetic Nomenclature ("ISCN") string 2612 may be automatically generated for a region of interest.

Figure 27:
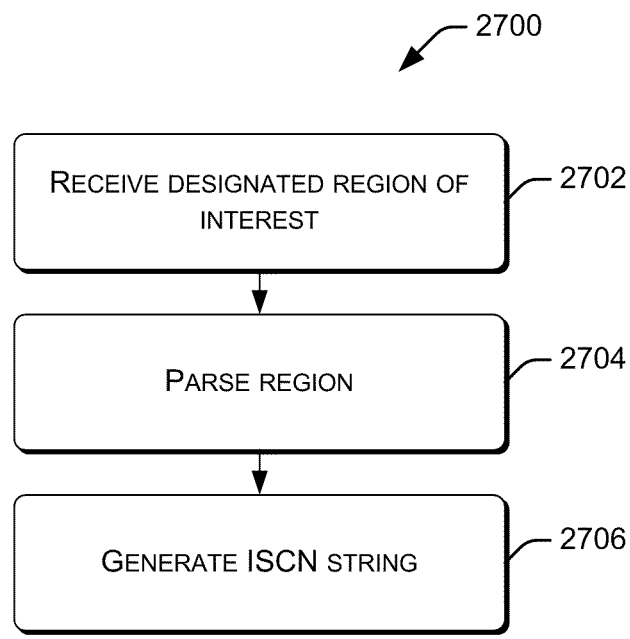
FIG. 27 illustrates a flow diagram for automatic generation of an ISCN.

FIG. 27 illustrates a flow diagram 2700 for automatic generation of an ISCN. The ISCN provides a common nomenclature for defining a specified region of a genome. This common nomenclature facilitates research and analysis by allowing users to annotate and search databases using common terminology. Manual generation of an ISCN may be tedious and may be prone to error, depending upon the experience of the user. Thus, automatic generation provides consistency, accuracy, and speed to a user. At 2702, a user designated region of interest is received. At 2704, the region is parsed and at 2706 the ISCN string is generated using ISCN nomenclature rules which may be stored in a database to describe the region.

Final Review of Data

Figure 28:
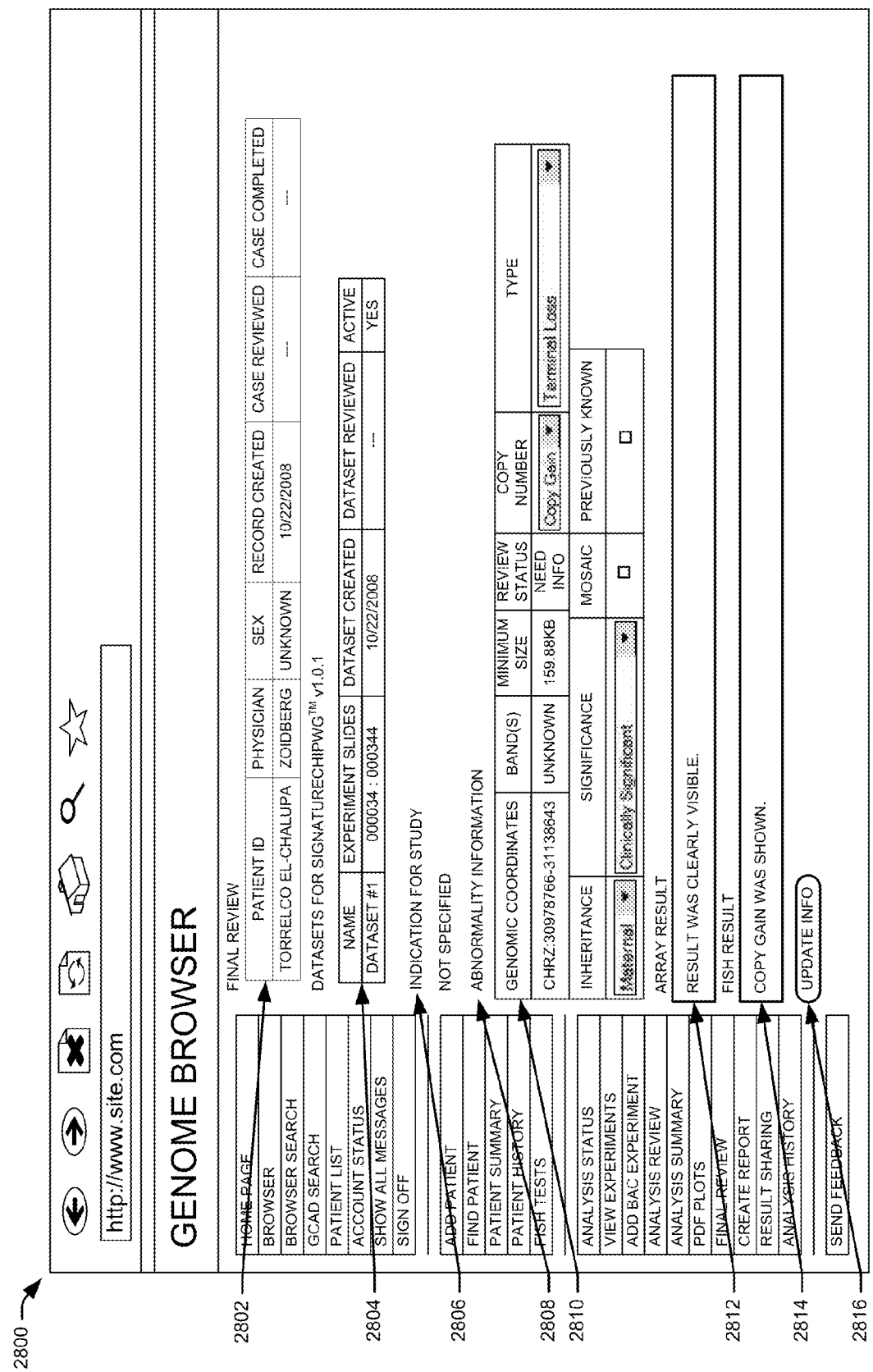
FIG. 28 illustrates a final review interface for entry of data about the analysis of a patient.

FIG. 28 illustrates a final review interface 2800 for entry of data about the analysis of a patient's experimental data. Patient information 2802 may be displayed. Dataset information 2804 may be displayed. Indications for study 2806 may be displayed. Abnormality information 2808 may be displayed, and an abnormality information input area 2810 for this information may be presented. The input area 2810 may comprise a menu for each abnormality, the menu further comprising for copy number, type, inheritance, significant, mosaic, and if previously known. An array result annotation box 2812 may be displayed allowing a user to type in comments about the array result. A FISH result annotation box 2814 may be displayed allowing a user to type in comments about the FISH result. An update info button 2816 updates the information in the database when selected.

Figure 29:
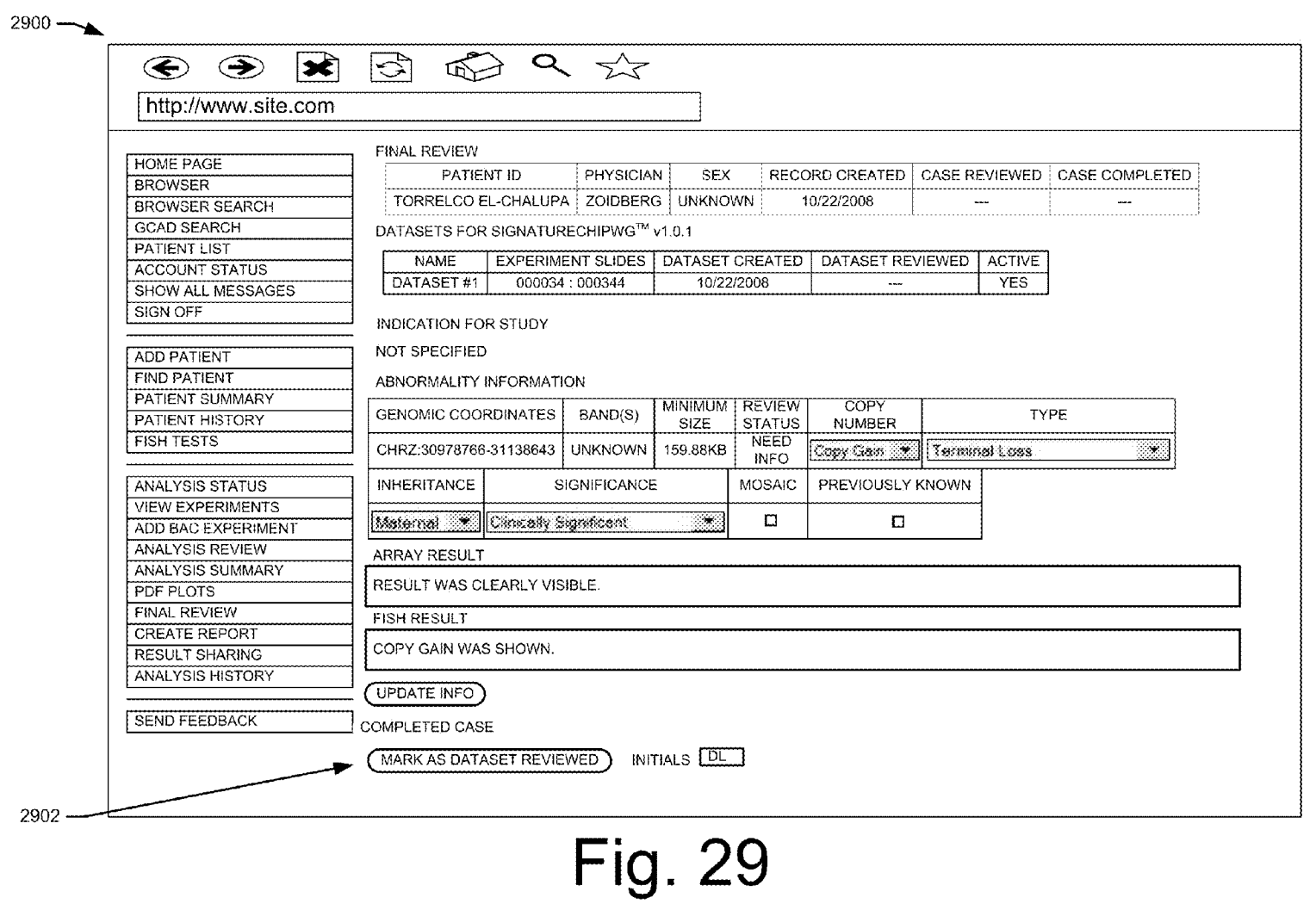

FIG. 29 illustrates the final review interface 2800 of FIG. 28 after selecting the update info button 2816. An input for identifying information about the user and a button 2902 for marking the dataset as reviewed is provided.

Figure 30:
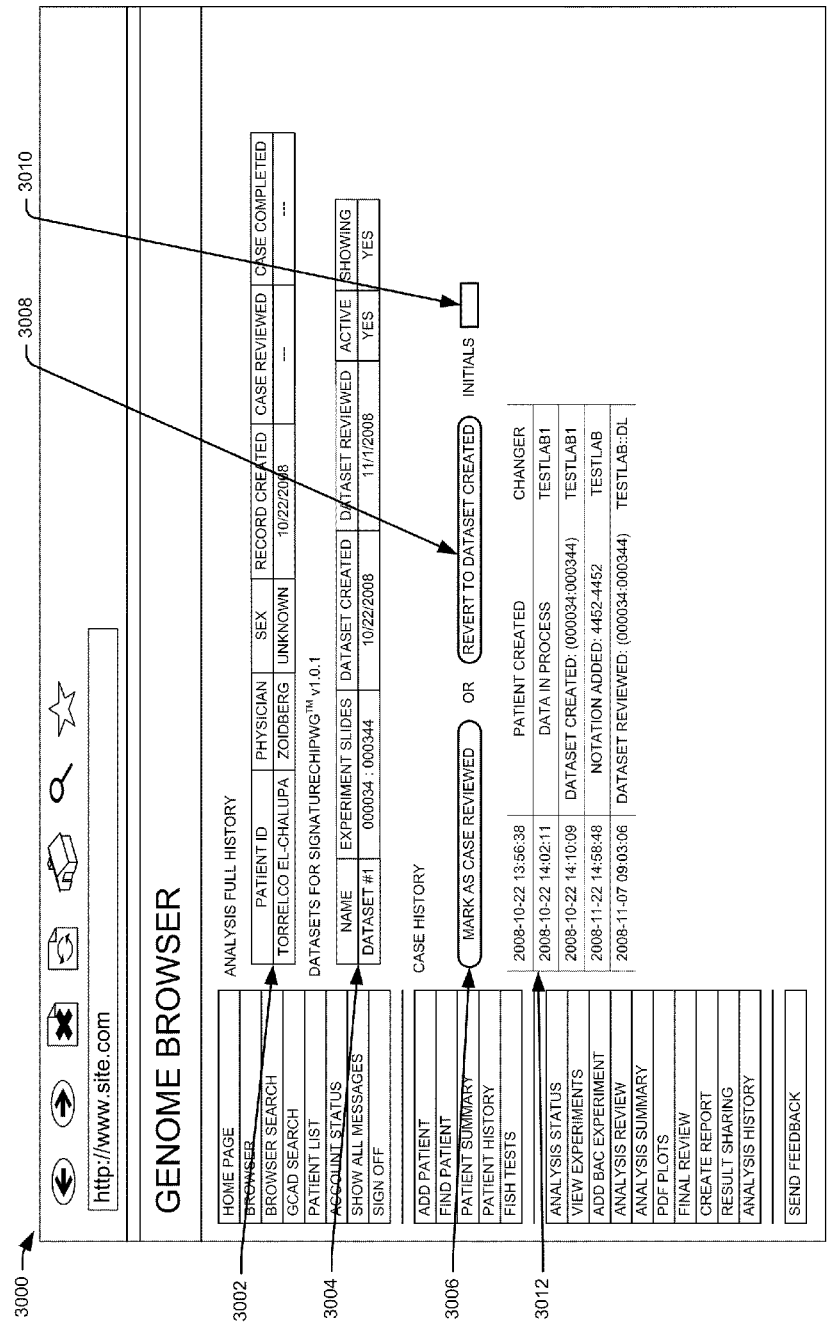
FIG. 30 illustrates an analysis full history displayed after indicating the final review of FIG. 29 as "reviewed" and showing datasets and case history for the patient.

FIG. 30 illustrates an analysis full history 3000 displayed after indicating the final review 2900 of FIG. 29 as having been "reviewed." Patient information 3002 and dataset information 3004 may be presented. A button to mark the case as reviewed 3006 or to revert to a dataset created 3008 may be presented. An input for identifying information about the user 3010 marking or reverting the case may be displayed. A history of transactions on the account 3012 may also be displayed, comprising date and time of activities relating to a patient file.

Automatically Generating a Detailed Report

Figure 31:
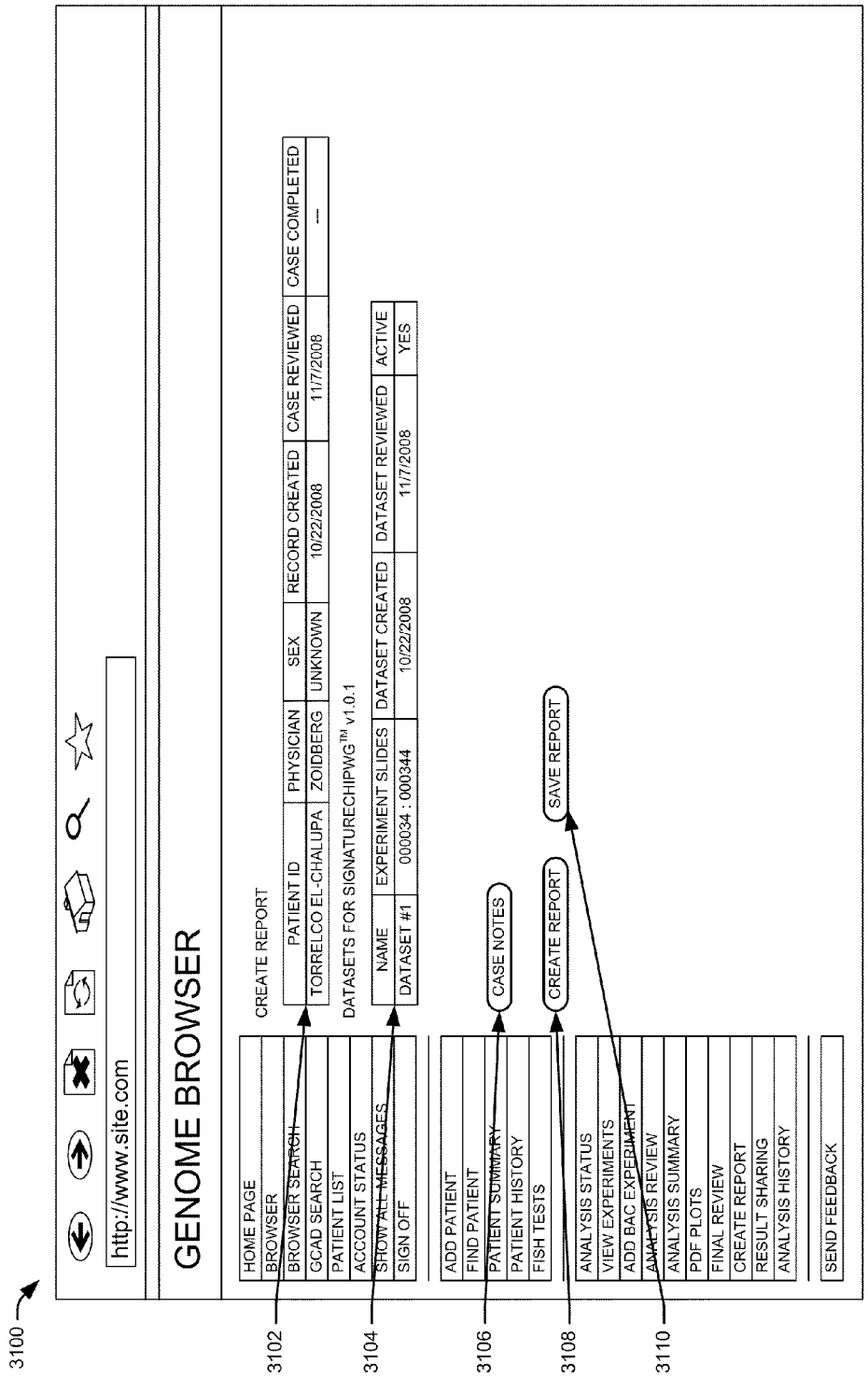
FIG. 31 illustrates a "create report" interface.

FIG. 31 illustrates a "create report interface" 3100. When a user in the interactive genome browser selects a "create report" button, the create report interface 3100 may be presented. Patient information 3102 and dataset information 3104 may be presented. A button to access case notes 3106 may also be displayed. A button to create a report 3108 and save a report 3110 may also be displayed.

FIG. 32 illustrates a report 3200 automatically generated after selection of the "Create Report" button 3108 and using information entered by the user. Patient information 3202 is presented, along with analysis results 3204 and an analysis summary 3206. Abnormalities 3208 are then displayed, including a view of the interactive genome browser 3210 showing the abnormalities. Details about the abnormalities 3212 are then presented.

FIG. 33 illustrates additional data which may be presented in the report 3200 of FIG. 32. A full abnormality list 3302 is shown, as well as information about the databases used in the report 3304, the information comprising version numbers, dates, editions, etc.

Figure 34:
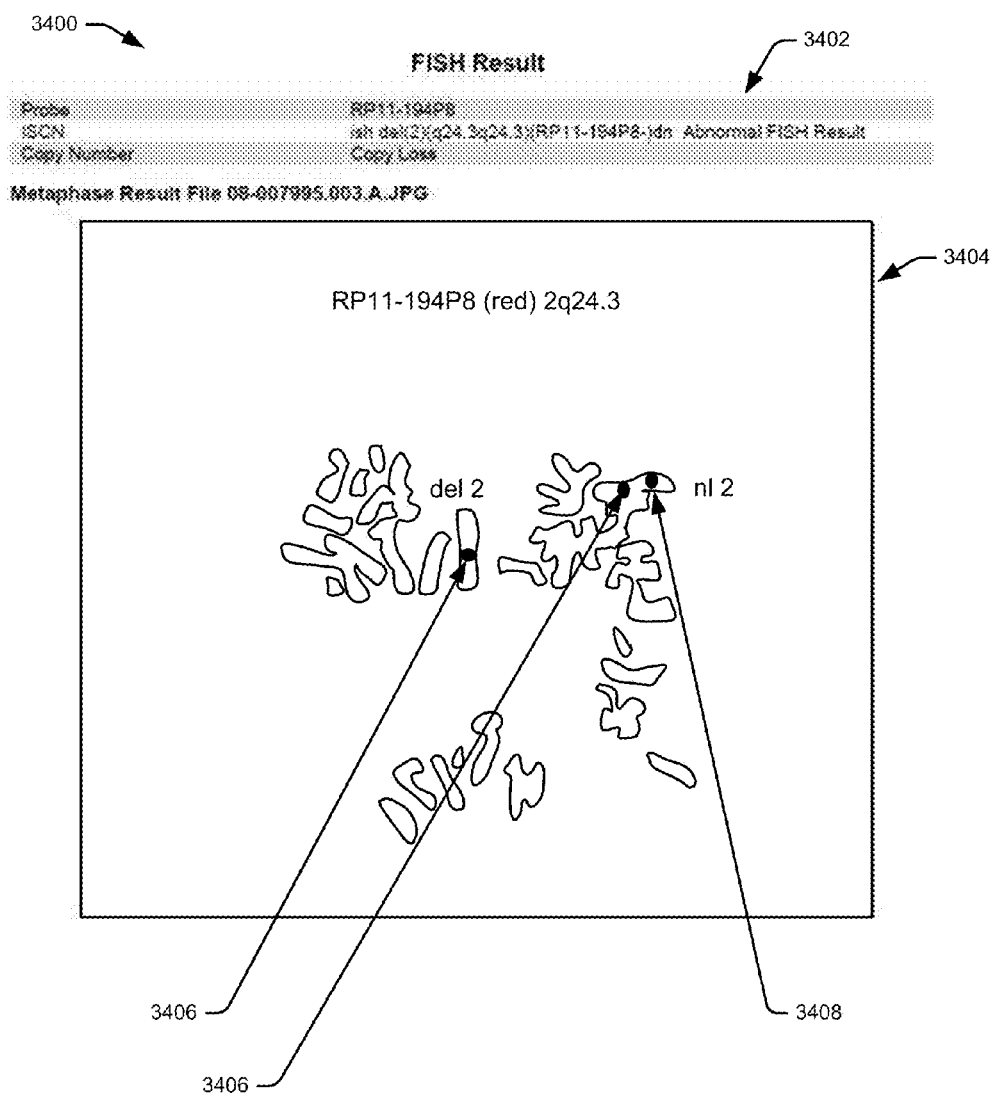
FIG. 34 illustrates a FISH result and associated imagery as presented in the report of FIG. 32.

FIG. 34 illustrates a section of a report 3400 where a FISH result may be presented. Details about the FISH probe 3402 may be presented, the details comprising the probe, ISCN and copy number. A reproduction of a FISH image 3404 (or another genetic testing image) may be presented in the report of FIG. 33. A green marker 3406 and a red marker 3408 is shown.

Figure 35:
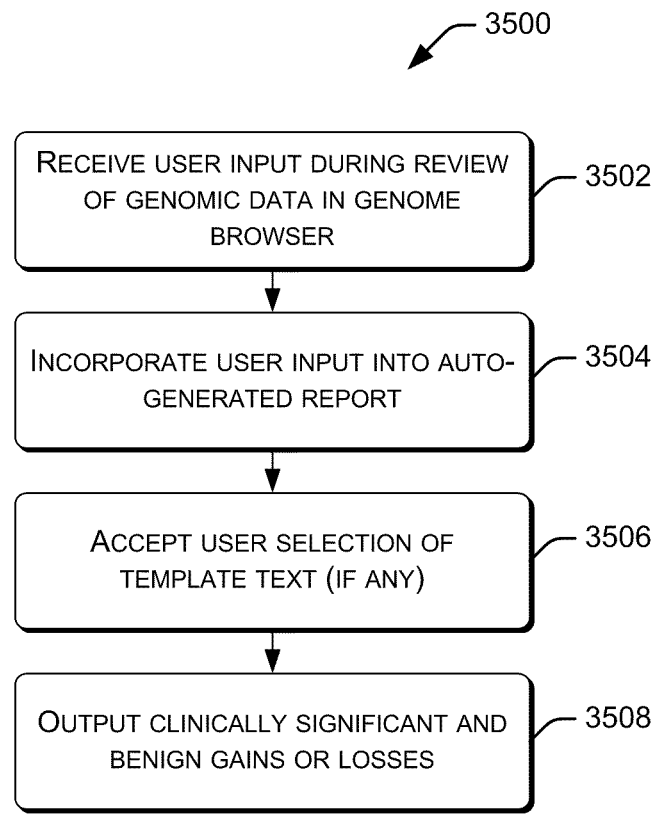
FIG. 35 is a flow diagram illustrating user input and automatic generation of a report.

FIG. 35 is a flow diagram 3500 of user input and automatic generation of a report. At 3502, during review of genomic data in the interactive genome browser, user input is received. This input comprises analysis, annotations, designations of regions of interest, and the like. At 3504, the user input is incorporated into an automatically generated report. At 3506, a user may accept selection of template text if desired, and edit the template text to customize For example, a block of commonly used text in a diagnosis may be re-used with modification to suit a particular patient. At 3608, a report is generated, which may comprise clinically significant and benign gains or losses.

Publishing Data to a Community

Figure 36:
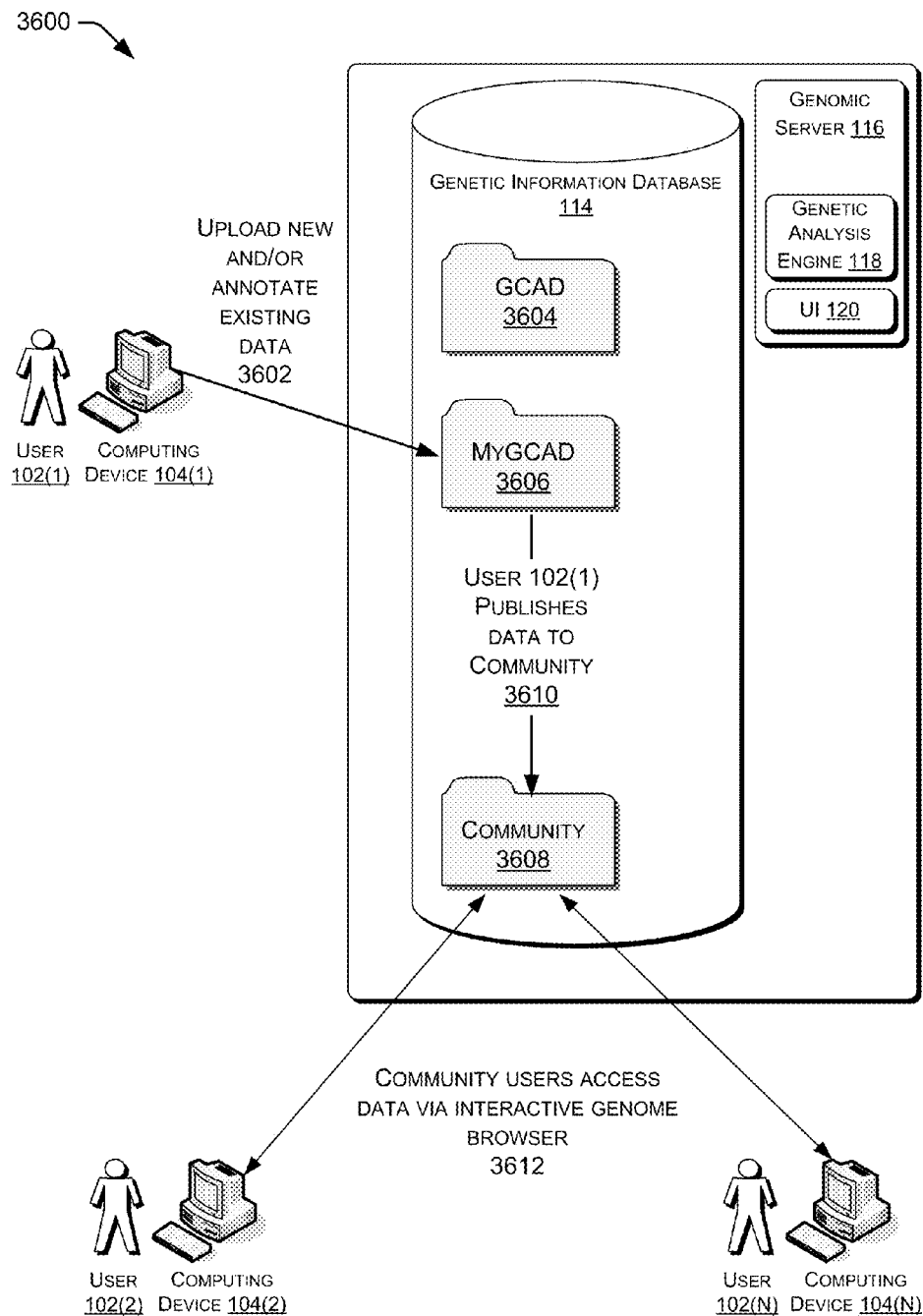
FIG. 36 illustrates sharing experiment data among community users.

FIG. 36 illustrates sharing patient data including experiment data among community users 3600. A user 102(1) uses computing device 104(1) executing an interactive genome browser to upload 3602 patient data or annotate existing patient data. This data is stored within genetic information database 114, which may comprise GCAD data 3604, MyGCAD data 3606, or community data 3610. When uploaded or annotated, data is present within the MyGCAD 3606 data. For example, the MyGCAD data comprises all of the patients analyzed by user 102(1). User 102(1) may then use the interactive genome browser to indicate that the patient data may be shared with a community 3608 comprising other users. The data is then published 3610 to the community 3608. Community users 102(2) through 102(N) may then access the data 3612 via an interactive genome browser.

Figure 37:
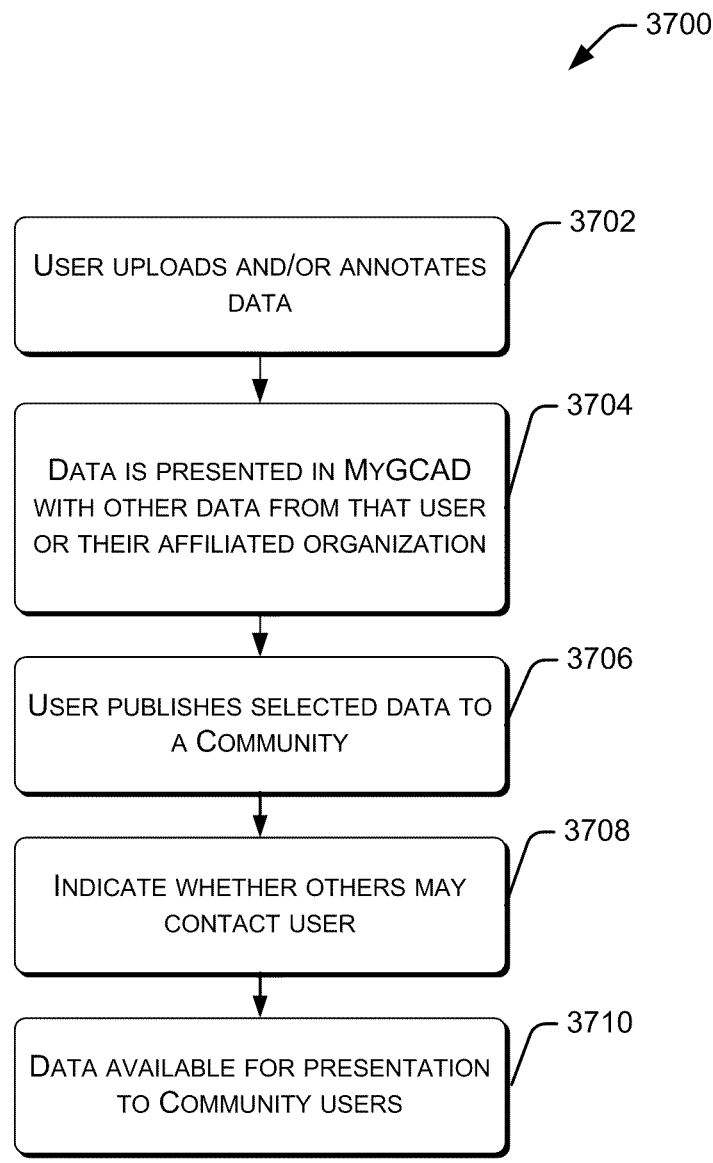
FIG. 37 is a flow diagram of sharing experiment data among community Users.

FIG. 37 is a flow diagram of sharing data 3700 among community users. At 3702, a user uploads or annotates patient data. At 3704, data is presented in MyGCAD with other data from that user or their affiliated organization to which they have MyGCAD access. At 3706, a user publishes selected data to a community. At 3708, the user may indicate whether others in the community may contact the publishing user. At 3710, the published data is made available for presentation to community users.

Figure 38:
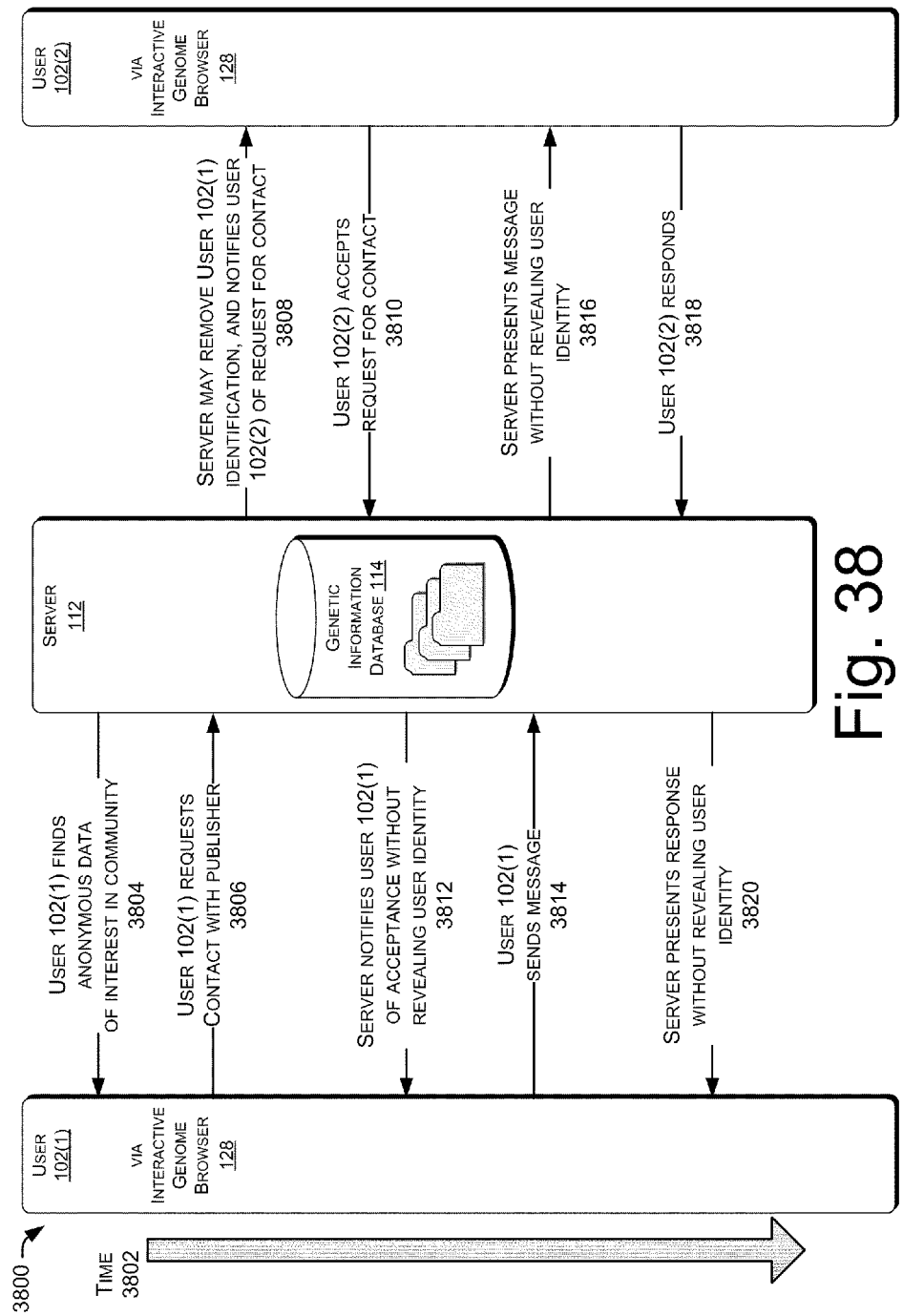
FIG. 38 is a diagram illustrating the interaction between two users to provide for anonymous exchange of patient information, if desired.

FIG. 38 is a diagram illustrating the interaction 3800 between two users to provide for anonymous exchange of patient information. In this diagram, time increases down, along the direction of arrow 3802. At 3804, user 102(1) finds anonymous data of interest on genome server 112 in the community data via interactive genome browser 128. At 3806, user 102(1) sends a request for contact with the publisher or the contact listed for that data to the server 112. At 3808, server 112 may remove user 102(1)'s identifying information where anonymity is requested, and notifies user 102(2) of the request for contact. At 3810, user 102(2) sends an acceptance of the request for contact 3810 using the interactive genome browser 128 to server 112. At 3812, the server 112 notifies user 102(1) of acceptance, without revealing clinician identity, where anonymity is requested. At 3814, user 102(1) sends a message to user 102(2) via server 112. At 3816, server 112 presents the message to user 102(2) without revealing user identity. At 3818, user 102(2) sends a response to server 112. At 3820, server 112 sends the response to user 102(1) without revealing user identity. Thus, the identity of the users may remain anonymous, when anonymity is desired. While two users are shown here in confidential communication, more than two users may communicate simultaneously or in a common format such as a web log ("blog") or newsgroup. When anonymity is not required or desired, user identification information is passed along through server 112 to the other party of the communication.

Figure 39:
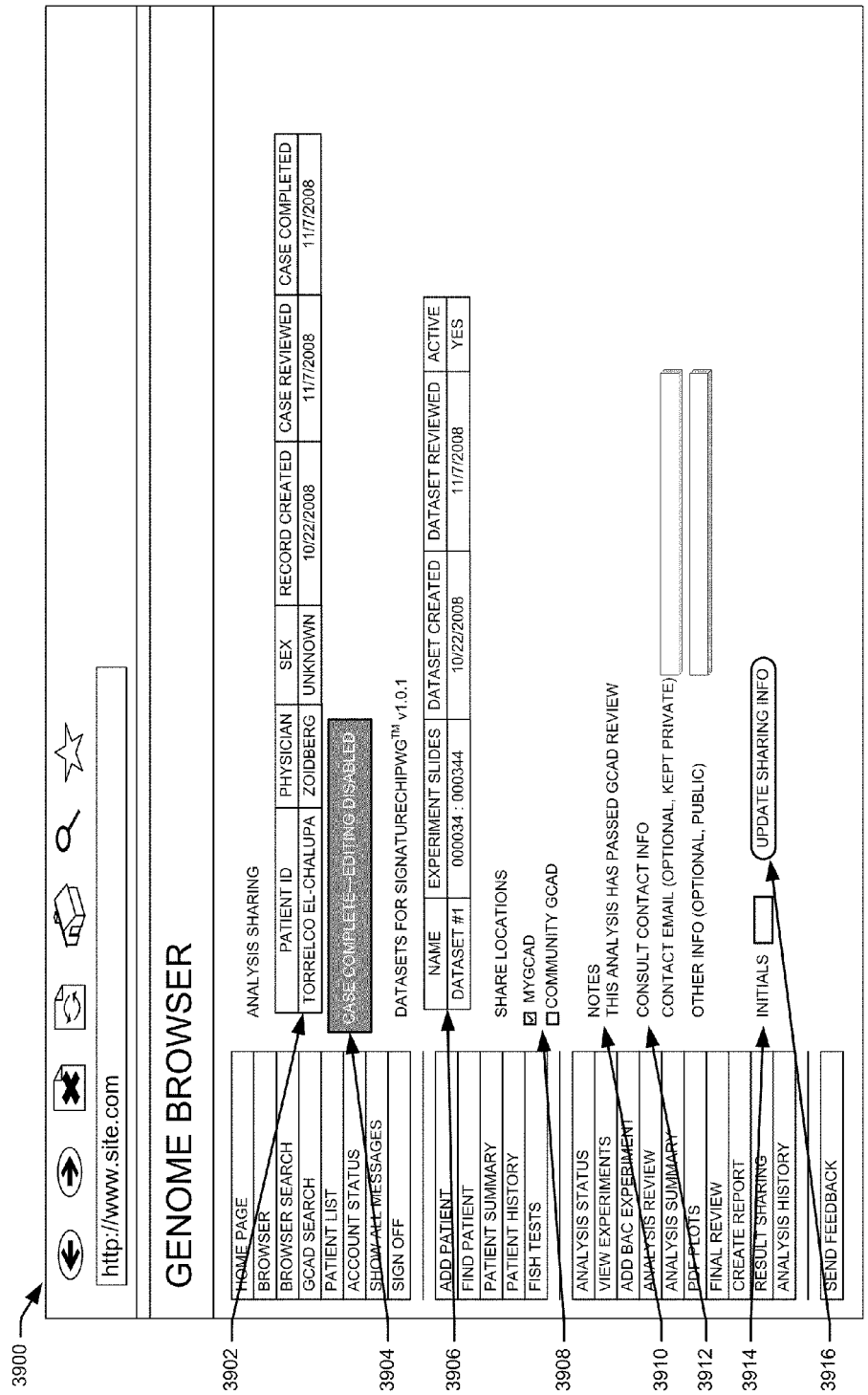
FIG. 39 illustrates an interface to share patient information.

FIG. 39 illustrates an interface in the interactive genome browser to share patient information. Patient information 3902 may be displayed. Case status 3904, for example, if the case is completed and editing is disabled, may be displayed. Dataset information 3906 may be displayed. Share locations 3908 may be indicated, for example whether the file is to be shared to MyGCAD and/or the community GCAD. Notes 3910 may be presented, for example, that the analysis has passed GCAD review. Contact information 3912 may be input, the contact information comprising an email address. An input for identifying information about the user 3914 and a button 3916 for updating the sharing information may also be displayed.

Communicating New Clinically Significant Data to Users

Figure 40:
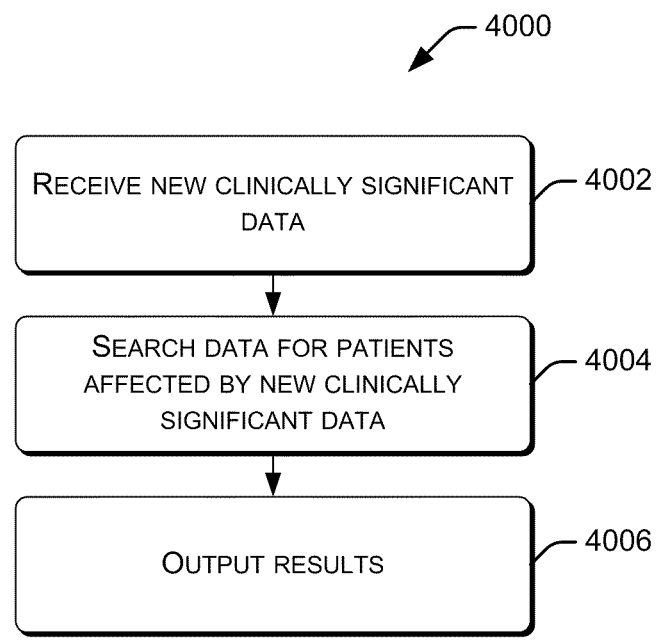
FIG. 40 is a flow diagram for outputting information about new clinically significant data for previously analyzed patients.

FIG. 40 is a flow diagram for outputting information about new clinically significant data for previously analyzed patients 4000. At 4002, new clinically significant data is received into the genetic information database. This may come from GCAD, MyGCAD, community data, or other data loaded into the genetic information database. At 4004, patient data is searched to find patients affected by the new clinically significant data. At 4006, search results may be output. This may include generating a notification to a user that a patient assigned to them has new clinically significant data available.

Searching Genomic Data

Figure 41:
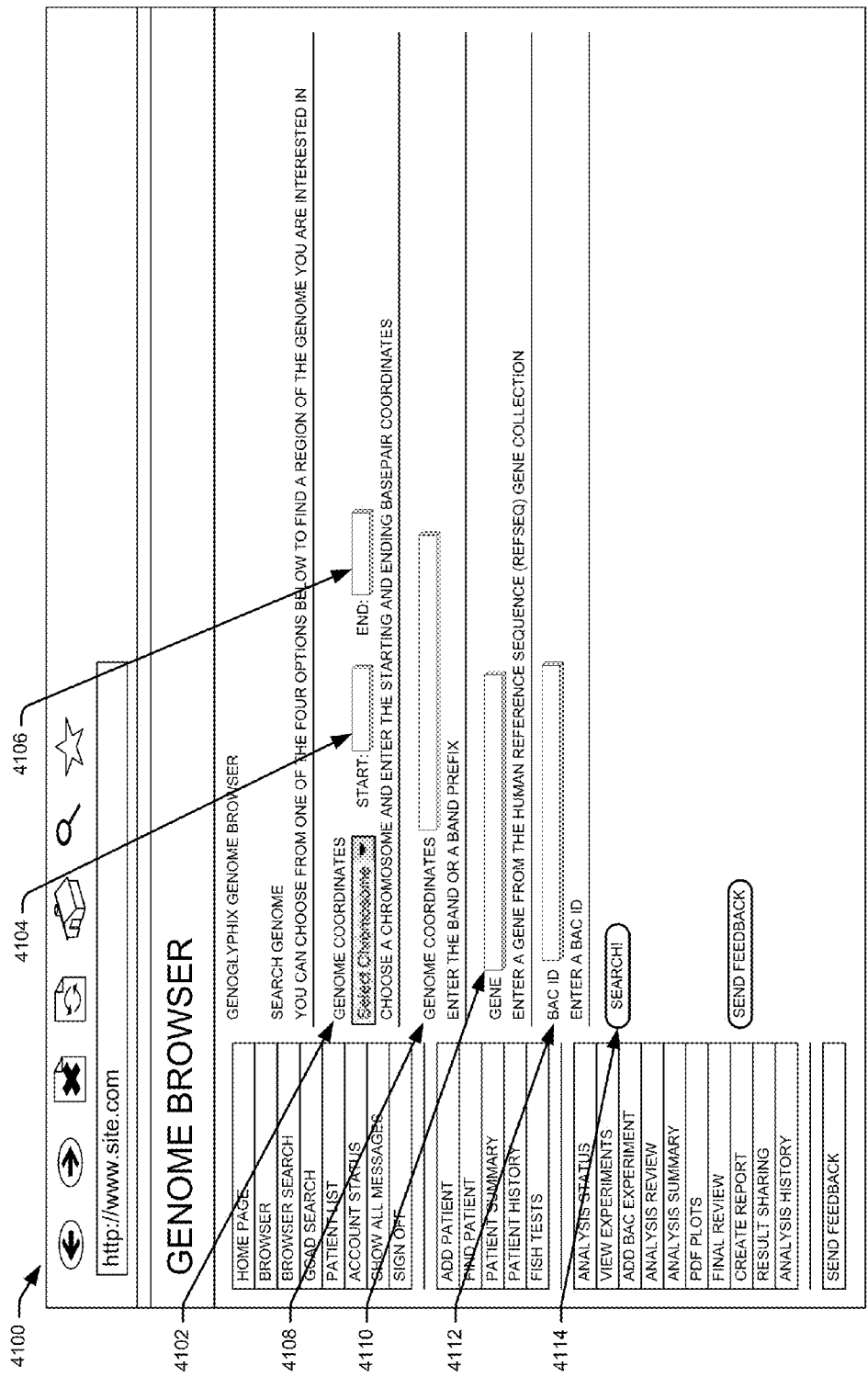
FIG. 41 illustrates a search interface allowing entry of genetic coordinates, chromosome band, gene, or BAC ID.

FIG. 41 illustrates a search interface 4100 for searching a genome by entering genetic coordinates, chromosome band, gene, or BAC ID. A user may input genomic coordinates 4102, indicate a starting base pair 4104 and/or ending base pair 4106. A chromosome band 4108 may be input, for example 2p23.2, 2p23, 2p2, or 2p. A particular gene 4110 may be entered, for example TBX1, DVL1, EXT2, etc. A BAC identifier (BAC ID) may be entered 4112, for example RP11-316L10 or CTD-3120F6. A search button 4114 is displayed and when selected initiates a search. A search may be with combinations of the above user inputs, for example a chromosome band and a BAC identifier.

Figure 42:
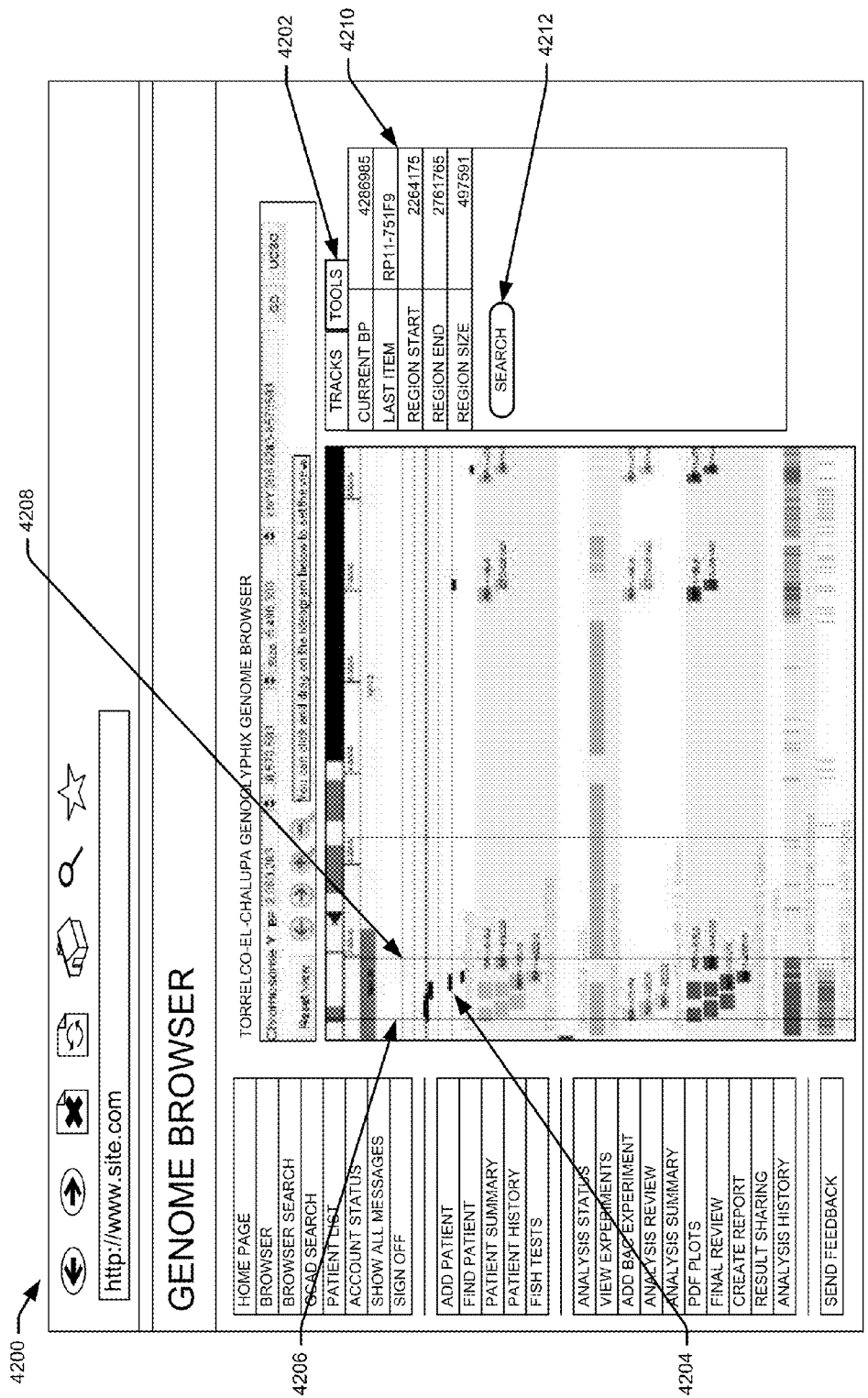
FIG. 42 illustrates additional features of the interactive genome browser, including the tools menu and selection of a region of interest.

FIG. 42 illustrates additional features of the interactive genome browser 800 of FIG. 8. The tools menu 4202 has been selected and is visible. A region 4204 is defined by region start 4206 and region end 4208. Tools data 4210 is displayed for the selection, the tools data displayed comprising the current base pair, last item selected, a region start, a region end, and a region size. Once selected, a search of the genetic information database may be initiated by selecting a search button 4212.

Figure 43:
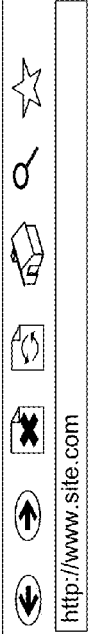
FIG. 43 illustrates a search interface in the interactive genome browser, which may be pre-populated with information about the selected region of interest of FIG. 42.

FIG. 43 illustrates a search interface 4300 in the interactive genome browser. When the search interface 4300 is accessed by selecting search button 4212 during display of a selected region, certain inputs on the search interface 4300 may be pre-populated. A header indicates the type of search 4302, for example, searching GCAD cases. A dataset to search may be selected 4304, for example GCAD, MyGCAD, Community GCAD, or benign abnomals. An identification number or GCAD number may be input 4306, and may be selected as being approximate 4308. Sex may be specified 4310. Platform may also be specified 4312. Tags 4314 may be selected. Tags are user defined, and may be used to organize patients. For example, a "validation" tag may be added to allow users to easily indicate when a patient has been validated. A keyword for an indication for study may be entered 4316, and may be set to require an exact match 4318. A diagnosis state 4320 may be selected, as well as inheritance 4322.

Abnormality classes 4324 may also be specified. These abnormality classes 4324 may comprise previously known abnormalities, mosaic abnormalities, unbalances translocation, terminal loss, interstitial deletion, terminal gain, interstitial duplication, Trisomy, marker, or other.

Abnormality location 4326 may also be specified. These location specifications may comprise selection of a chromosome, start band, end band, starting coordinate, ending coordinate, starting clone, ending clone, gene name, and maximum size of abnormality. Based on the previous selection of a region of interest by a user, some of these fields may be pre-populated, for example chromosome, start band, end band, starting coordinate, and ending coordinate. A user may also select to include abnormalities overlapping a range specified by the location specifications.

A user may sort results 4328 by several fields, and choose to output results 4330 to screen, printer, file, and so forth. A user may initiate a search by selecting a submit button 4332, or select a clear form button 4334 to clear the form.

Figure 44:
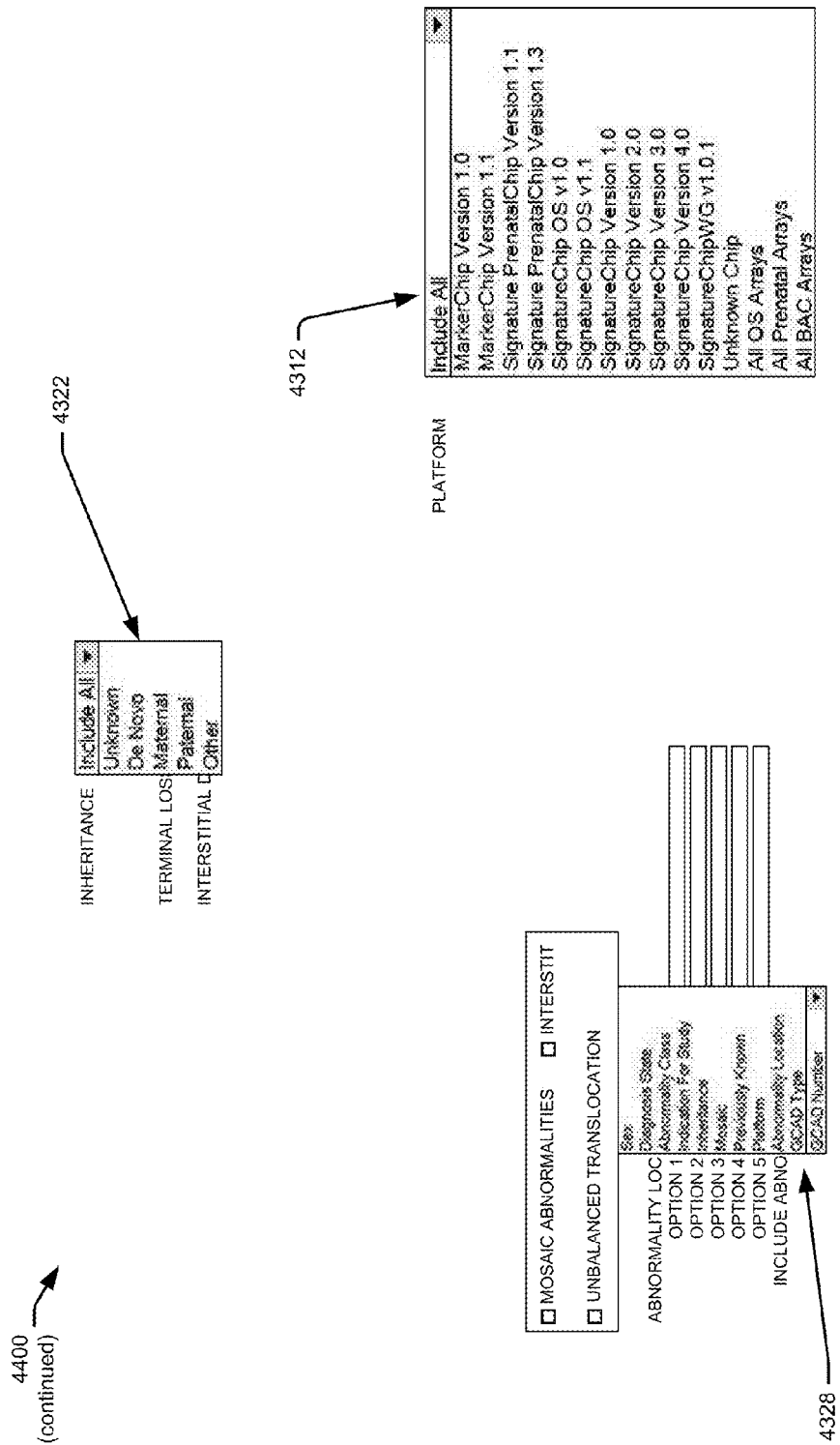
FIG. 44 illustrates additional search options available in the search of FIG. 43.

FIG. 44 illustrates additional search options available in the search of FIG. 43. Platform 4312 may comprise a list of available testing platforms and groupings of those platforms, for example, all BAC arrays, or include all Inheritance 4322 may comprise unknown, de novo, maternal, paternal, other, or include all. Sorting of results 4328 may comprise fields like GCAD number, sex, diagnosis state, abnormality class, indication for study, inheritance, mosaic, previously known, platform, abnormality location, GCAD type, etc.

Figure 45:
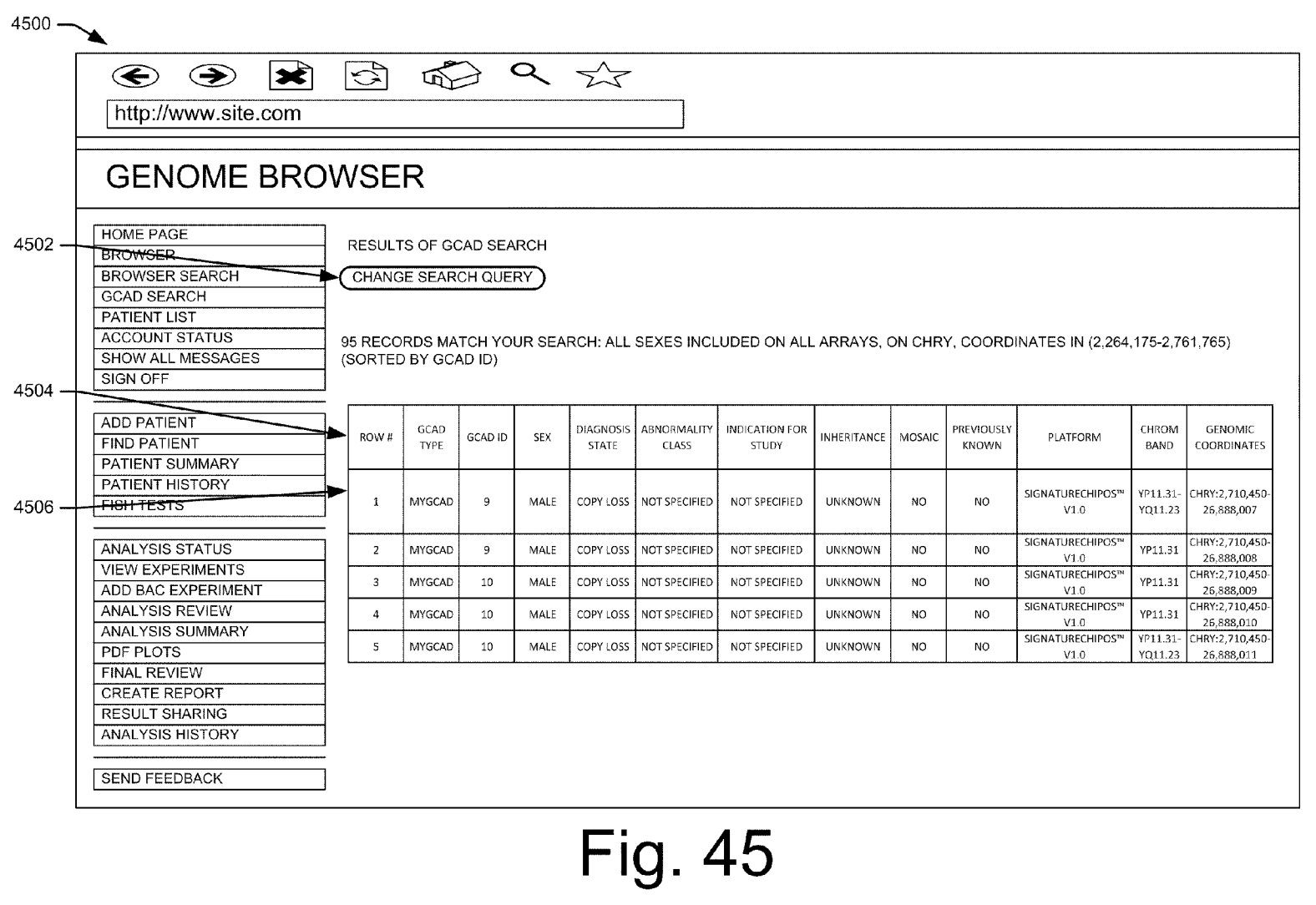

FIG. 45 illustrates a partial listing of results from the search of FIG. 43. A change search query button 4502 may be displayed to permit changing parameters of the search. A listing of search results 4504 may be displayed. A user may select a search result for additional details, for example result 4506.

Figure 46:
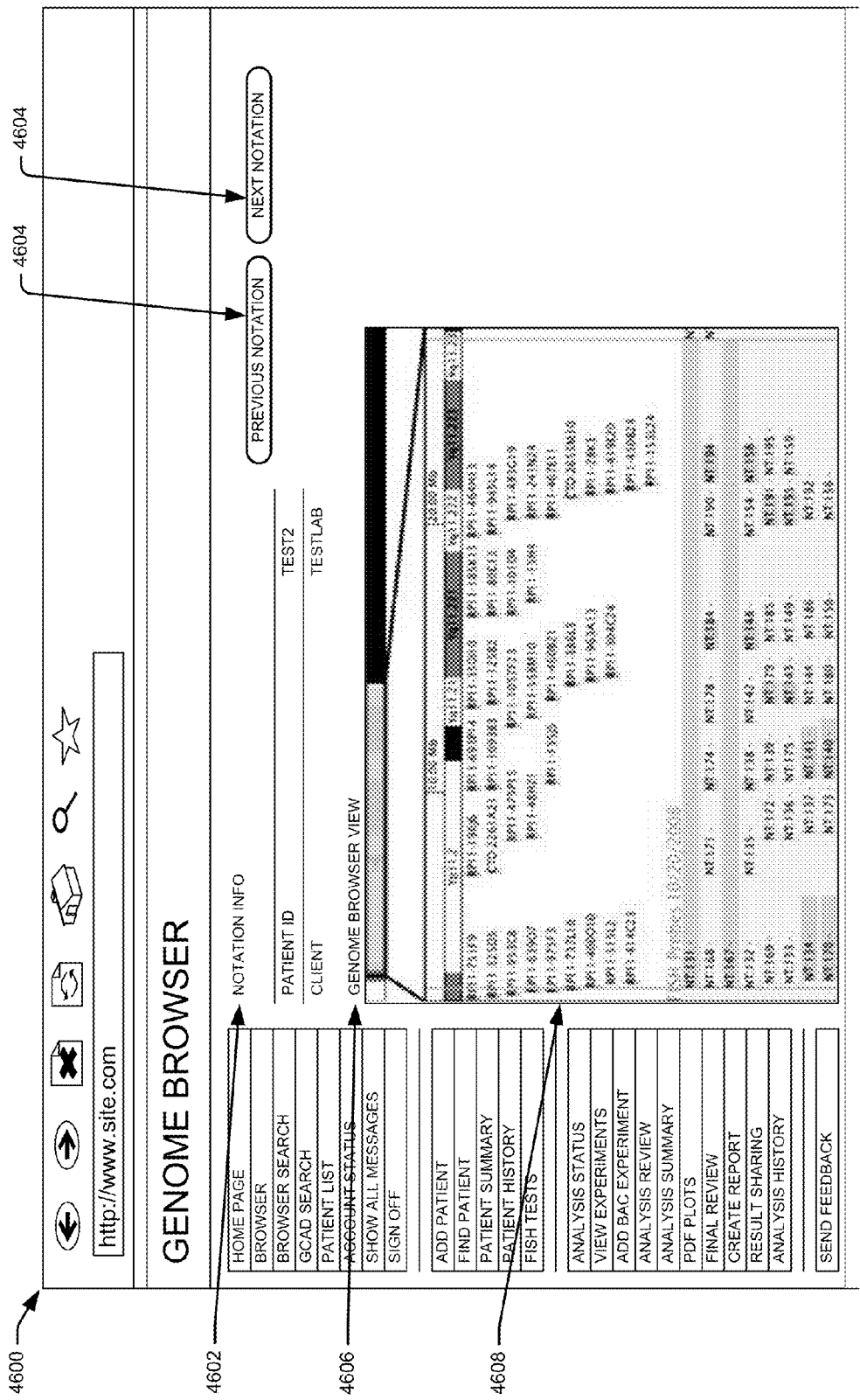
FIG. 46 illustrates detailed information available upon selection of one of the search results of FIG. 45.

FIG. 46 illustrates detailed information 4600 available upon selection of search result 4506 of FIG. 46. Notation information 4602 is presented, along with navigation buttons 4604 to permit moving to a previous notation or a next notation. A genomics browser view 4606 is presented. The genomics browser view includes a large scale chromosome ideogram with a box indicating the displayed area, as previously described. A base pair ruler may also be displayed. Available FISH probes 4608 are displayed.

Figure 47:
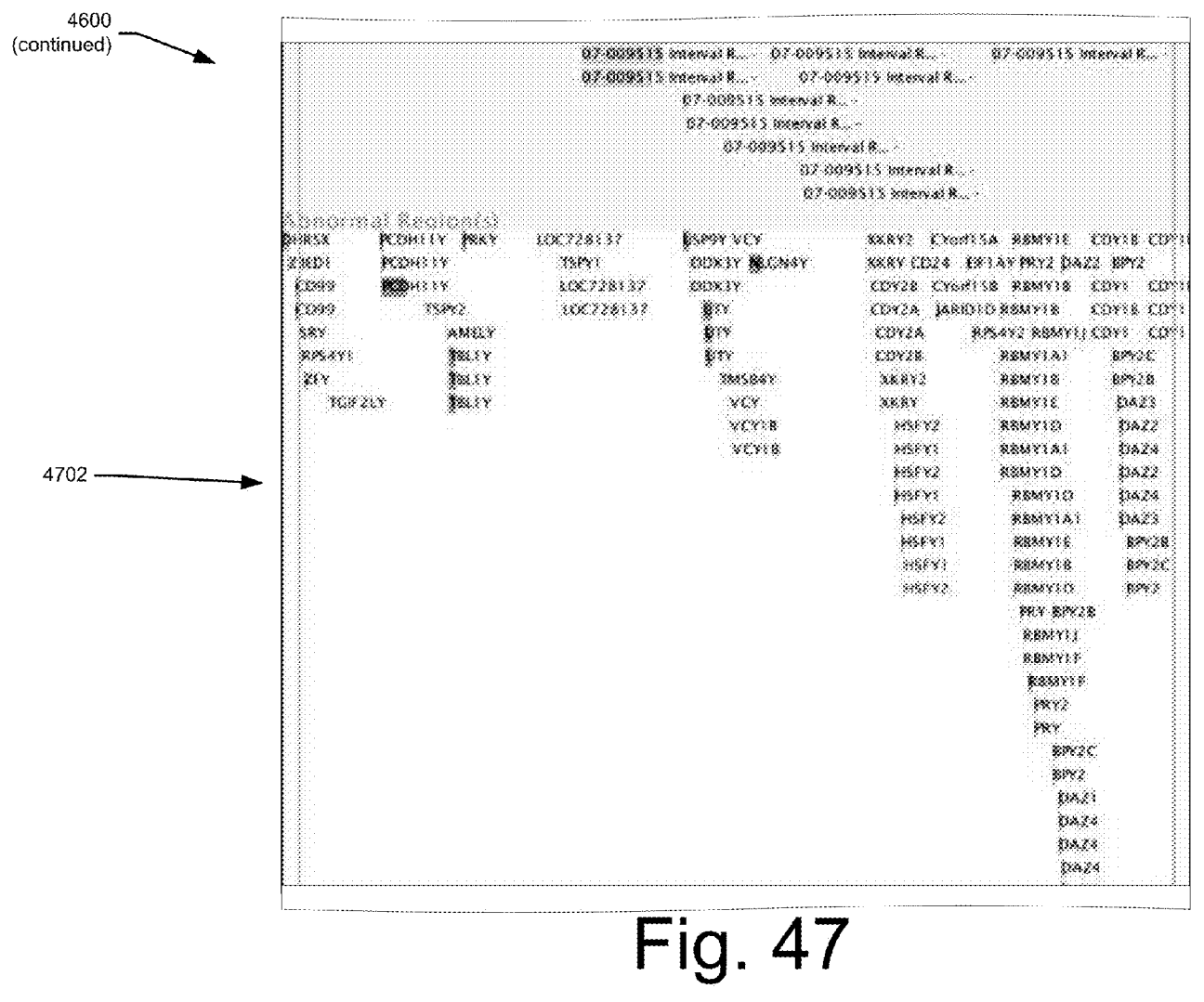

FIG. 47 illustrates the additional detailed information 4600 from FIG. 46 including an additional genetic data tracks for abnormal regions 4702.

Figure 48:
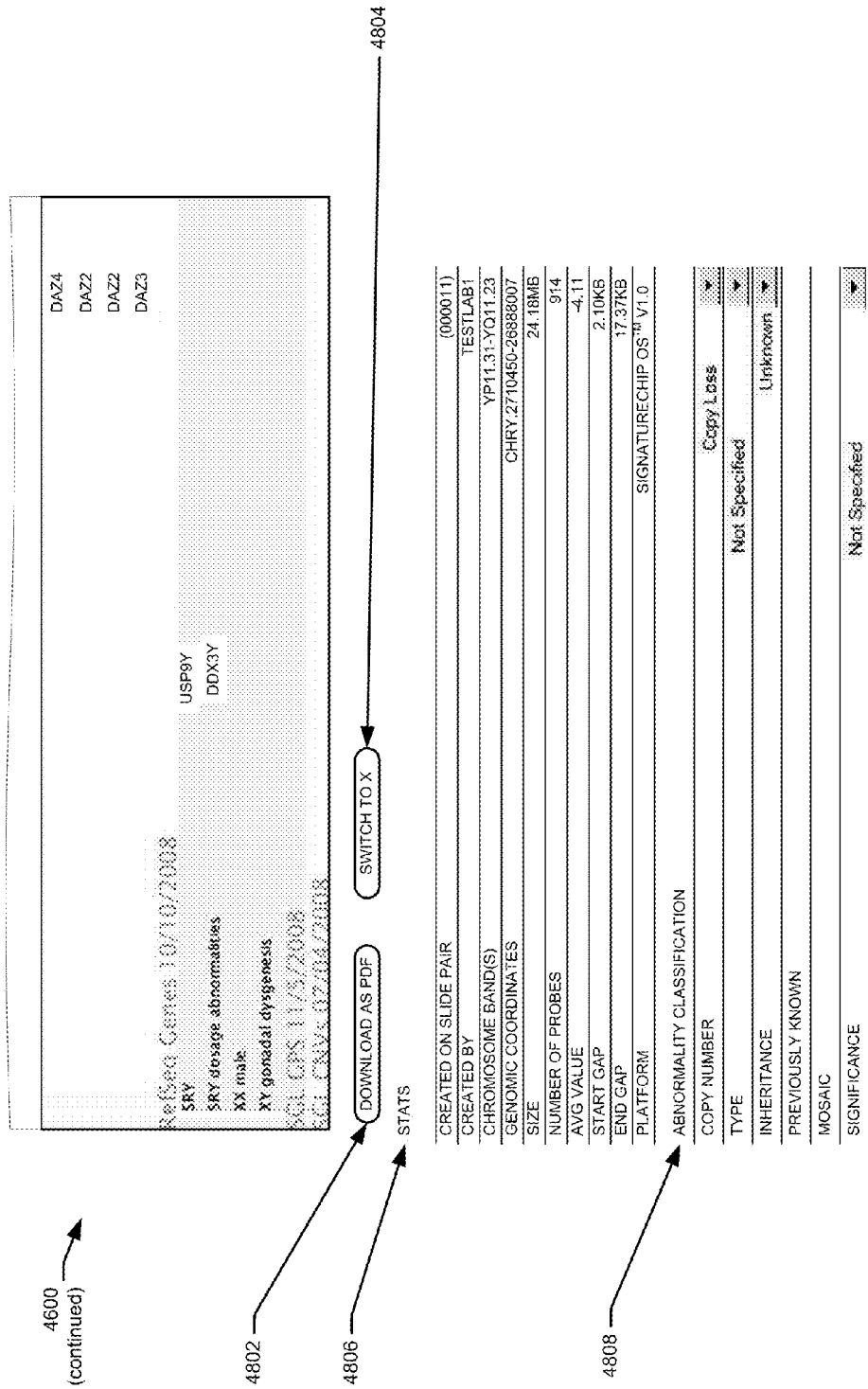
FIG. 48 illustrates the additional detailed information from FIG. 46 including statistics and abnormality classification information.

FIG. 48 illustrates the additional detailed information 4600 from FIG. 46. A button to download the information as a PDF may be presented 4802. Downloads to other formats such as TIFF, JPEG, etc., may also be presented. A switch display to the X chromosome button 4804 may be displayed. As described earlier, when an X chromosome is being displayed, this button may present a "switch to the Y chromosome" button.

Statistics 4806 may also be displayed. These statistics 4806 may comprise the slide pair created on, who created the statistics, chromosome band(s), genomic coordinates, size, number of probes, average value, start gap, end gap, and platform of the test. Abnormality classification 4808 may also be entered. Abnormality classification 4808 may comprise copy number, type, inheritance, whether previously known, mosaic, and significance.

Figure 49:
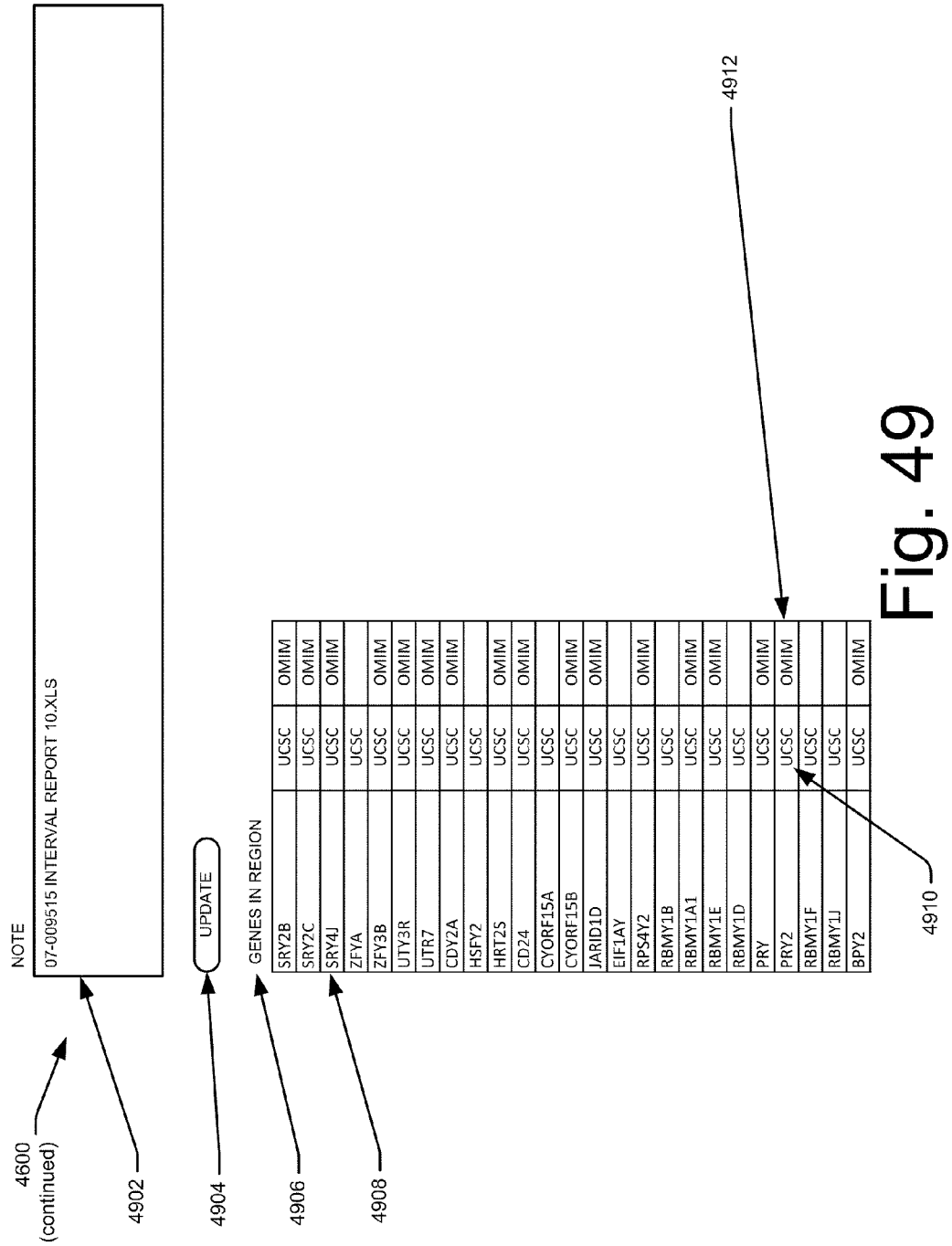
FIG. 49 illustrates additional details available in the detailed view of FIG. 46, including an area for a user to enter notes, and a display of genes in the region displayed and links for those genes to external databases.

FIG. 49 illustrates additional details available in the detailed view 4600 of FIG. 46. An area for a user to enter notes 4902 may be displayed, along with an update button 4904 to incorporate changes. A list of genes in the region 4906 may be displayed. The list of genes in the region 4906 may comprise a gene identifier 4908, and a link to external databases such as the genetic database at University of California at Santa Cruz (UCSC) 4910 and/or the Online Mendelian Inheritance in Man (OMIM) genetic database 4912.

FIG. 50 illustrates additional details available in the detailed view 4600 of FIG. 46. A listing of FISH probes in the region 5002 are shown.

Conclusion

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. One or more computing devices, comprising:
one or more processors;
memory; and
a web browser application configured to execute an interactive genome browser script, stored in the memory and executable on the one or more processors, the interactive genome browser script configured to:
receive, from a user, a set of genetic data associated with a patient undergoing analysis from one or more servers,
remove certain genetic data from the set of patient genetic data to generate filtered genetic data of the patient indicating chromosomal segment gain or loss that is associated with one or more genetic disorders that include at least one of Down syndrome, Cri du chat, Wolf-Hirschhorn syndrome, Edward's syndrome, Jacobsen syndrome or Turner syndrome, and
receive genetic data associated with multiple patients from the one or more servers, and statistically analyze the multiple patients data to determine how often the multiple patients exhibit chromosomal gain or loss across an autosomal region associated with the one or more genetic disorders, and through comparison of the filtered genetic data to the statistically analyzed multiple patients data to determine whether the chromosomal segment gain or loss of the patient undergoing analysis is clinically significant.

2. One or more computing devices as recited in claim 1, wherein the interactive genome browser script is further configured to:
build a first genetic data track based on the filtered genetic data,
build a second genetic data track based on genetic data associated with multiple patients,
align the first genetic data track and the second genetic data track by base pairs,
display the first genetic data track and the second genetic data track, and
transmit to the one or more servers an interpretive comment of the patient undergoing analysis, the interpretive comment being accessible by a community of users when a user of the users are analyzing the set of genetic data associated with the patient undergoing analysis.

3. One or more computing devices as recited in claim 2, wherein the interactive genome browser script is further configured to present to the user an additional track of genetic data published to the community of the users, the additional track being aligned by base pairs with the first genetic data track.

4. One or more computing devices as recited in claim 2, wherein the interactive genome browser script is further configured to display an automatically generated International Standard Cytogenetic Nomenclature (ISCN) string describing a region designated by the user.

5. One or more computing devices as recited in claim 1, wherein the interactive genome browser script is further configured to:
facilitate communications associated with the determining between the user and at least one of a researcher, a clinician and a doctor.

6. One or more computing devices as recited in claim 1, wherein the interactive genome browser script is further configured to:
provide a visual representation of the chromosomal gain or loss of the patient, and the statistical results depicting how often the chromosomal gain or loss is found in the multiple patients data.

7. One or more computing devices, comprising:
one or more processors;
memory; and
a web browser application configured to execute an interactive genome browser script, stored in the memory and executable on the one or more processors, the interactive genome browser script configured to:
receive, over a network, first genetic data associated with a patient undergoing analysis and receive second genetic data associated with multiple patients from a server,
wherein the first genetic data indicating chromosomal segment gain or loss that is associated with one or more genetic disorders that include at least one of Down syndrome, Cri du chat, Wolf-Hirschhorn syndrome, Edward's syndrome, Jacobsen syndrome or Turner syndrome, and the second genetic data is a statistical analysis of the multiple patients data,
build a first genetic data track comprising the first genetic data
build a second genetic data track comprising the second genetic data associated with the multiple patients,
align the first genetic data track and the second genetic data track by base pairs,
display the first genetic data track and second genetic data track,
statistically determine how often the multiple patients exhibit chromosomal gain or loss across an autosomal region associated with the one or more genetic disorders, and through comparison of the first genetic data to the second genetic data determine whether the chromosomal segment gain or loss of the patient undergoing analysis is clinically significant, and
transmit interpretive comments of a particular patient that are derived from the first genetic data track and second genetic data track to the server.

8. One or more computing devices as recited in claim 7, wherein the interactive genome browser script is configured to display an automatically-generated genetic information report based on clinician input during review and/or analysis of data in the interactive genome browser script.

9. One or more computing devices as recited in claim 8, wherein the genetic information report shows benign chromosome segment gains or losses.

10. One or more computing devices as recited in claim 8, wherein the genetic information report further comprises a template for commonly used text which may be modified.

11. One or more computing devices as recited in claim 7, wherein the interactive genome browser script presents clinically significant data affecting patients assigned to a user, wherein the clinically significant data were added after the user analyzed the patient.

12. One or more computing devices as recited in claim 7, wherein the interactive genome browser script is further configured to:
provide a visual representation of the chromosomal gain or loss of the patient, and the statistical results depicting how often the chromosomal gain or loss is found in the multiple patients data.

13. One or more computing devices as recited in claim 7, wherein the interactive genome browser script is further configured to:
enable anonymous exchange of patient information associated with the interpretive comments among users.

14. One or more computing devices, comprising:
one or more processors;
memory; and
a web browser application configured to execute an interactive genome browser script, stored in the memory and executable on the one or more processors, the interactive genome browser script configured to:
receive, over a network, first genetic data associated with a patient undergoing analysis and second genetic data associated with multiple patients from a server, the first genetic data indicating chromosomal segment gain or loss that is associated with one or more genetic abnormalities,
build a first genetic data track based on the first genetic data associated with the patient undergoing analysis,
build a second genetic data track based on the second genetic data associated with the multiple patients,
calculate a frequency of occurrence of the chromosomal segment gain or loss associated with a chromosomal region of the patient using the second genetic data associated with multiple patients,
analyze the genetic data associated with the patient for the chromosomal region using the frequency of the occurrence of the chromosomal segment gain or loss to enable a user to determine a degree that the patient has the one or more genetic abnormalities, and
display the first genetic track and the second genetic track by indicating the chromosomal segment gain or loss associated with the chromosomal region of the patient undergoing analysis, and one or more corresponding frequencies associated with the chromosomal region of the multiple patients.

15. One or more computing devices as recited in claim 14, wherein the interactive genome browser script is further configured to initiate a search of genetic data.

16. One or more computing devices as recited in claim 15, wherein the search is configured to filter on a range of base pairs selected within the interactive genome browser script.

17. One or more computing devices as recited in claim 15, wherein the search is configured to filter by chromosomal location.

18. One or more computing devices as recited in claim 15, wherein the search is configured to filter by a search term.

19. One or more computing devices as recited in claim 18, wherein the search term is a symptom.

20. One or more computing devices as recited in claim 18, wherein the search term is a clinical sign.

21. One or more computing devices as recited in claim 15, wherein the search is configured to filter to display patients assigned to a user.

22. One or more computing devices as recited in claim 15, wherein the search is configured to display a summarized set of search results.

23. One or more computing devices as recited in claim 22, wherein selection of the summarized set of search results displays a detailed version of the search results.

24. One or more computing devices as recited in claim 14, wherein the interactive genome browser script is further configured to search genetic data published to a community of users.

25. A system comprising:
one or more processors;
memory; and
an application, stored in the memory and executable on the one or more processors, configured to:
retrieve and display a patient genetic data track comprising genetic data associated with a patient,
load an additional genetic data track comprising genetic data associated with multiple other patients, the patient genetic data track and the additional genetic data track including indications of chromosomal segment gain or loss for at least one of the patient or a particular patient of the multiple other patients, the chromosomal segment gain or loss being associated with one or more genetic disorders that include at least one of Down syndrome, Cri du chat, Wolf-Hirschhorn syndrome, Edward's syndrome, Jacobsen syndrome or Turner syndrome,
display the additional genetic data track in alignment with the patient genetic data track,
calculate a frequency of occurrence of the chromosomal segment gain or loss associated with a chromosomal region among the multiple other patients; and
analyze the genetic data associated with the patient for the chromosomal region using the frequency of the occurrence of the chromosomal segment gain or loss to enable a user to determine a degree that the patient has the one or more genetic disorders.

26. The system as recited in claim 25, wherein the application is further configured to:
allow a user to annotate the genetic data, and
publish the annotations or clinical patient information to a community of the user.

27. The system as recited in claim 25, wherein the displaying the additional genetic data track in alignment with the patient genetic data track comprises display the additional genetic data track in alignment with the patient genetic data track for comparison, and the application is further configured to facilitate a physician to order one or more additional genetic tests based on the comparison.

28. The system as recited in claim 25, wherein the application is further configured to compare chromosomal segment gain or loss of one patient against one or more relatives of the one patient to determine whether the chromosomal segment gain or loss of the one patient is clinically significant, wherein the relative(s) is selected from the group consisting of parent, child, sibling, maternal half sibling, maternal uncle, maternal aunt, maternal grandparent, paternal half sibling, paternal uncle, paternal aunt, paternal grandparent, spouse or partner, sperm donor, egg donor, and surrogate.

* * * * *